US012655753B2

(12) United States Patent
Jain

(10) Patent No.: US 12,655,753 B2
(45) Date of Patent: Jun. 16, 2026

(54) SURVEILLANCE USING PARTICULATE TRACERS

(71) Applicant: CHEVRON U.S.A. INC., San Ramon, CA (US)

(72) Inventor: Lokendra Jain, Pearland, TX (US)

(73) Assignee: CHEVRON U.S.A. INC., San Ramon, CA (US)

( * ) Notice: Subject to any disclaimer, the term of this patent is extended or adjusted under 35 U.S.C. 154(b) by 776 days.

(21) Appl. No.: 18/079,068

(22) Filed: Dec. 12, 2022

(65) Prior Publication Data

US 2023/0184098 A1 Jun. 15, 2023

Related U.S. Application Data

(60) Provisional application No. 63/288,447, filed on Dec. 10, 2021.

(51) Int. Cl.
*E21B 47/11* (2012.01)
*G01N 33/24* (2006.01)
*G01N 33/28* (2006.01)

(52) U.S. Cl.
CPC ............ *E21B 47/11* (2020.05); *G01N 33/241* (2013.01); *G01N 33/2823* (2013.01)

(58) Field of Classification Search
CPC ........ E21B 47/11; E21B 47/00; E21B 47/003; E21B 47/007; E21B 47/111; E21B 43/267; E21B 43/00; E21B 43/20; E21B 43/12; E21B 43/121; G01N 33/241; G01N 33/2823; G01N 2030/8854; G01N 11/04; G01V 11/00; G01V 1/30; G01V 2210/671; G01V 2210/57; G01V 2210/20; G01V 5/00

USPC ........... 73/152.44, 152.04, 1.02; 166/250.12, 166/250.01; 702/12, 6, 11, 17, 13, 7, 9, 702/22, 30, 187, 104, 100, 1, 189; 703/10, 2, 9, 6, 12
See application file for complete search history.

(56) References Cited

U.S. PATENT DOCUMENTS 8,949,029 B2 * 2/2015 Nyhavn .................. E21B 47/11
702/6
2010/0258309 A1 * 10/2010 Ayodele .................. E21B 36/04
166/272.3

(Continued)

FOREIGN PATENT DOCUMENTS

CA 2854989 A1 * 5/2013 ............. G06T 17/05
CN 108825226 11/2018

(Continued)

OTHER PUBLICATIONS

Hogg Michael "CA-2854989-A1", pp. 1-57, May 23, 2013 (Year: 2013).*

(Continued)

*Primary Examiner* — Michael J Dalbo
*Assistant Examiner* — Kaleria Knox
(74) *Attorney, Agent, or Firm* — Ana C. Jaquez

(57) ABSTRACT

In accordance with some embodiments, a method of determining a flow profile for a wellbore using unique particulate tracers is disclosed. At least one unique particulate tracer is pumped throughout each stage, each stage group, or any combination thereof during a hydraulic fracturing operation performed in the subterranean formation.

31 Claims, 63 Drawing Sheets

(56) References Cited

U.S. PATENT DOCUMENTS

| | | | |
|---|---|---|---|
| 2010/0307744 A1* | 12/2010 | Cochet | C09K 8/706 |
| | | | 166/308.1 |
| 2011/0239754 A1 | 10/2011 | Dyer | |
| 2014/0260694 A1* | 9/2014 | Szlendak | E21B 49/08 |
| | | | 73/863.51 |
| 2016/0097750 A1* | 4/2016 | Van Herzen | C09K 11/62 |
| | | | 427/127 |
| 2018/0155597 A1* | 6/2018 | Burns | C09K 8/03 |
| 2018/0238147 A1 | 8/2018 | Shahri | |
| 2018/0298274 A1 | 10/2018 | Zhao | |
| 2020/0123889 A1* | 4/2020 | Subrahmanyan | C09K 8/032 |
| 2020/0283678 A1 | 9/2020 | Ogle | |
| 2023/0184096 A1 | 6/2023 | Jain | |
| 2023/0184097 A1 | 6/2023 | Jain | |

FOREIGN PATENT DOCUMENTS

| | | | | |
|---|---|---|---|---|
| CN | 110735632 | | 1/2020 | |
| EP | 4194663 B1 | | 9/2025 | |
| WO | 2012057634 | | 5/2012 | |
| WO | WO-2012057634 A1 * | | 5/2012 | E21B 27/02 |
| WO | 2015097116 | | 7/2015 | |
| WO | WO-2015097116 A1 * | | 7/2015 | G01N 33/2882 |
| WO | 2021194373 | | 9/2021 | |
| WO | 2021194373 A1 | | 9/2021 | |

OTHER PUBLICATIONS

Extended European Search Report, issued on Jul. 28, 2023, during the prosecution of European Application No. 22212927.2.

Izgec, B., et al; "Flow-Rate Estimation From Wellhead-Pressure and Temperature Data"; (Feb. 2010), SPE 115790, SPE Production & Operations, pp. 31-39.

Jain, Lokendra, et al.; "Analytical Tracer Interpretation Model for Fracture Flow Characterization and Swept Volume Estimation in Unconventional Wells"; (2021), Proceedings of the 9th Unconventional Resources Technology Conference (URTeC:5357), pp. 3384-3403.

Li, Haitao, et al.; "Evaluation of the Release Mechanism of Sustained-Release Tracers and its Application in Horizontal Well Inflow Profile Monitoring"; (2021), ACS Omega, vol. 6 (29), pp. 19269-19280.

Flow loop testing to validate Tracerco's solid chemical inflow tracer technology, Tracerco Limited, 2021, available at. https://www.tracerco.com/downloads/case-studies/flow-loop-testing-to-validate-tracercos-solid-chemical-inflow-tracer-technology/, 3 pages.

* cited by examiner

Flowing fluid with diffused tracer

Particle with tracer

Flowing fluid

Tracer recovery curves indicative of binary response of flow vs no-flow

StageN

StageM

Tracer Con.

Time, t

Stages  StageM  StageN

FIG. 3B

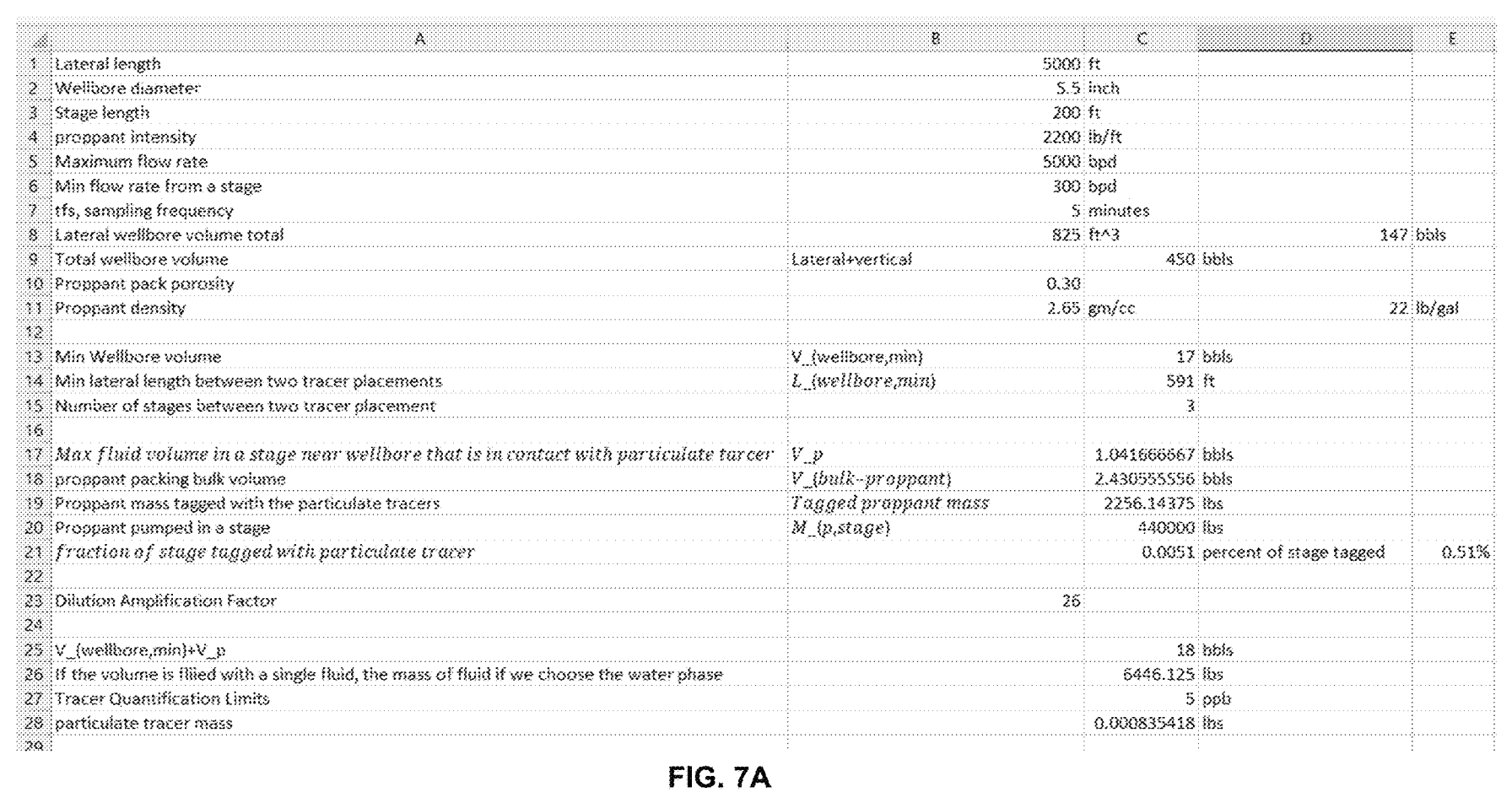

| | A | B | C | D | E |
|---|---|---|---|---|---|
| 1 | Lateral length | | 5000 ft | | |
| 2 | Wellbore diameter | | 5.5 inch | | |
| 3 | Stage length | | 200 ft | | |
| 4 | proppant intensity | | 2200 lb/ft | | |
| 5 | Maximum flow rate | | 5000 bpd | | |
| 6 | Min flow rate from a stage | | 300 bpd | | |
| 7 | tfs, sampling frequency | | 5 minutes | | |
| 8 | Lateral wellbore volume total | | 825 ft^3 | | 147 bbls |
| 9 | Total wellbore volume | Lateral+vertical | 450 bbls | | |
| 10 | Proppant pack porosity | | 0.30 | | |
| 11 | Proppant density | | 2.65 gm/cc | | 22 lb/gal |
| 12 | | | | | |
| 13 | Min Wellbore volume | $V\_\{wellbore,min\}$ | 17 bbls | | |
| 14 | Min lateral length between two tracer placements | $L\_\{wellbore,min\}$ | 591 ft | | |
| 15 | Number of stages between two tracer placement | | 3 | | |
| 16 | | | | | |
| 17 | *Max fluid volume in a stage near wellbore that is in contact with particulate tracer* | $V\_p$ | 1.041666667 bbls | | |
| 18 | proppant packing bulk volume | $V\_\{bulk-proppant\}$ | 2.430555556 bbls | | |
| 19 | Proppant mass tagged with the particulate tracers | *Tagged proppant mass* | 2256.14375 lbs | | |
| 20 | Proppant pumped in a stage | $M\_\{p,stage\}$ | 440000 lbs | | |
| 21 | *Fraction of stage tagged with particulate tracer* | | 0.0051 percent of stage tagged | | 0.51% |
| 22 | | | | | |
| 23 | Dilution Amplification Factor | | 26 | | |
| 24 | | | | | |
| 25 | $V\_\{wellbore,min\}+V\_p$ | | 18 bbls | | |
| 26 | If the volume is filled with a single fluid, the mass of fluid if we choose the water phase | | 6446.125 lbs | | |
| 27 | Tracer Quantification Limits | | 5 ppb | | |
| 28 | particulate tracer mass | | 0.000835418 lbs | | |
| 29 | | | | | |

FIG. 7A

| Label | | Value | Unit |
|---|---|---|---|
| Dilution Amplification factor | 20 | | |
| V_{wellbore,inj}÷V_p | | | |
| If the volume is filled with a single fluid, the mass of fluid if we choose the water phase | | 18 | bbls |
| Tracer Quantification Limits | | 6446.125 | lbs |
| particulate tracer mass | | 5 | ppb |
| | | 0.000835419 | lbs |
| shut-in | | 24 | hours |
| min tracer release rate | | 3.79735E-05 | lbs/lbs/day |
| Design particulate total mass | | 22 | lbs |
| Design particulate tracer mass to tagged proppant mass | | 0.029751152 | |
| Example total tracer used | if the release rate is linear | 3.79735E-05 | |
| Tracer life time from lab, days | | 180 | days |
| Total particulate place | | 22 | lbs |
| Total tracer mass released without the dead tracer fraction lost in the beginning | lbs | 0.15037304 | lbs |
| | gms | 68.35236345 | gms |
| Dead tracer mass proportion | % | 30 | |
| Total loaded tracer mass greater than equal to | | 0.21482172 | lbs |
| | | 97.64623636 | grams |
| Tracer mass per unit of particulate | | 0.009764624 | grams |

FIG. 7B

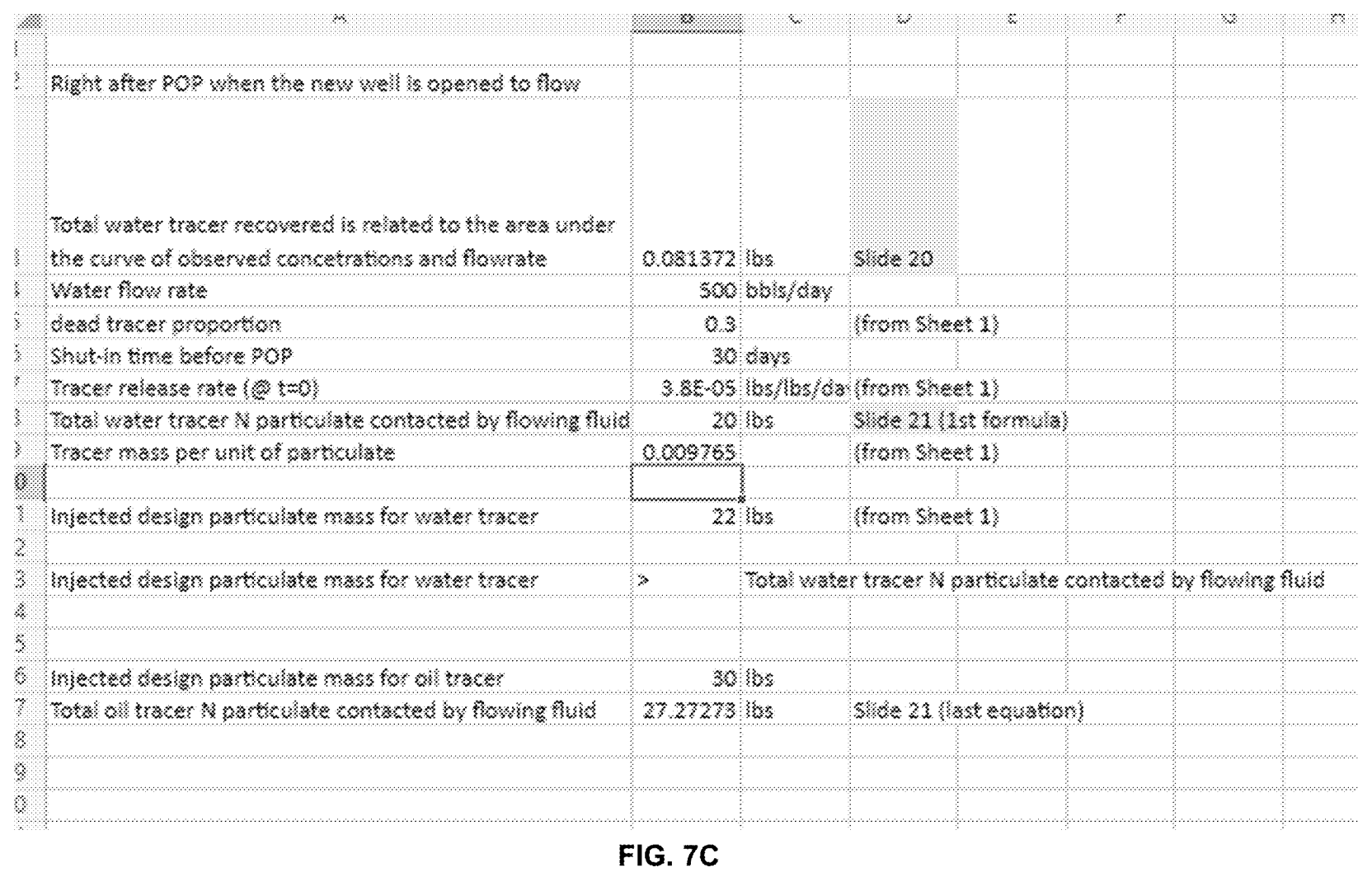

| | | | |
|---|---|---|---|
| Right after POP when the new well is opened to flow | | | |
| Total water tracer recovered is related to the area under | | | |
| the curve of observed concentrations and flowrate | 0.081372 | lbs | Side 20 |
| Water flow rate | 500 | bbls/day | |
| dead tracer proportion | 0.3 | | |
| Shut-in time before POP | 30 | days | |
| Tracer release rate (@ t=0) | 3.8E-05 | lbs/lbs/day | (from Sheet 1) |
| Total water tracer N particulate contacted by flowing fluid | 20 | lbs | (from Sheet 1) |
| Tracer mass per unit of particulate | 0.009765 | | Slide 21 (1st formula) |
| | | | (from Sheet 1) |
| Injected design particulate mass for water tracer | 22 | lbs | (from Sheet 1) |
| Injected design particulate mass for water tracer | > | | Total water tracer N particulate contacted by flowing fluid |
| Injected design particulate mass for oil tracer | 30 | lbs | |
| Total oil tracer N particulate contacted by flowing fluid | 27.27273 | lbs | Slide 21 (last equation) |

FIG. 7C

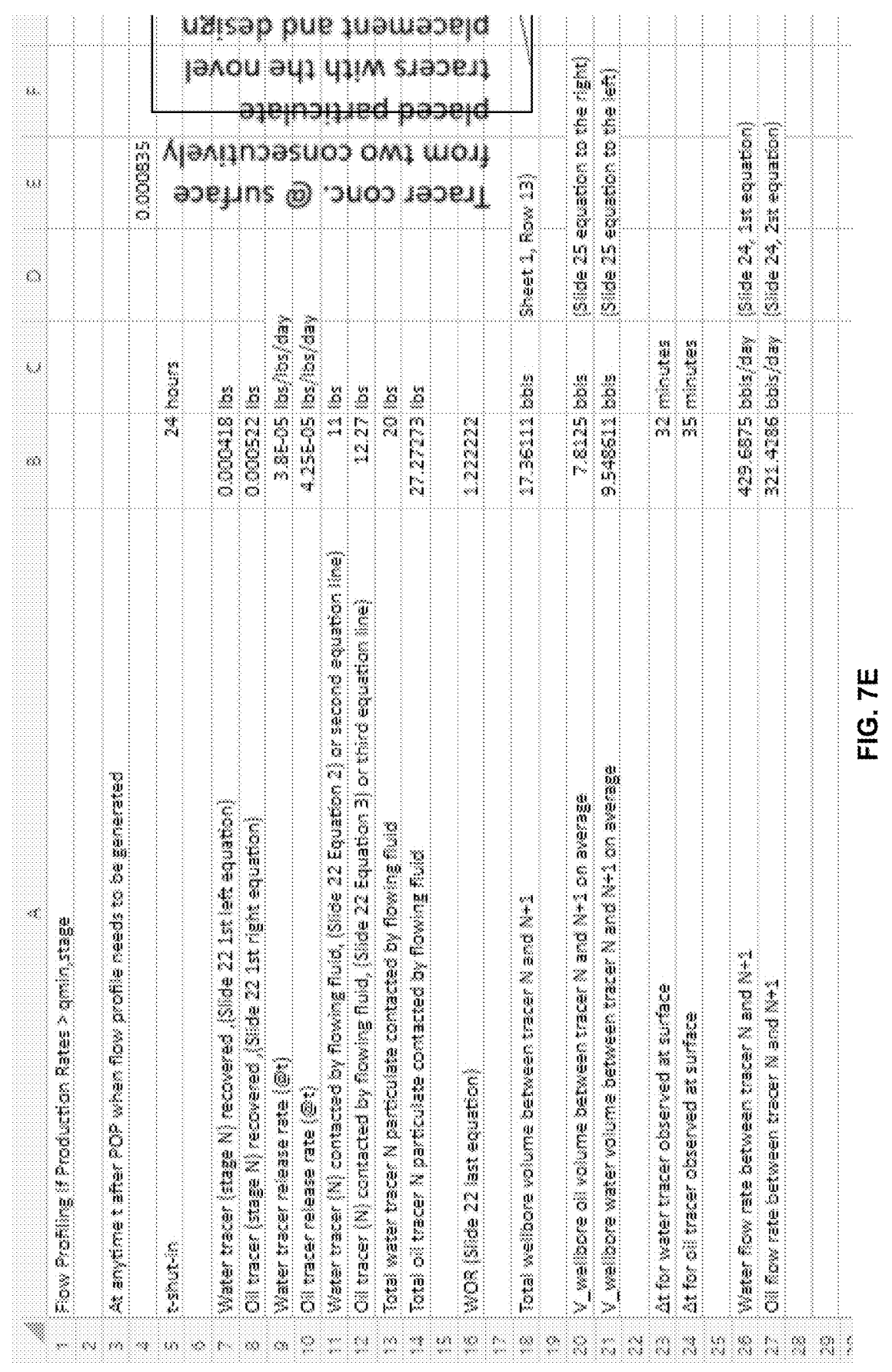

Tracer conc. @ surface from two consecutively placed particulate tracers with the novel placement and design 0.000835

| | A | B | C | D |
|---|---|---|---|---|
| 1 | Flow Profiling (if Production Rates > gmin.stage) | | | |
| 2 | | | | |
| 3 | At anytime t after POP when flow profile needs to be generated | | | |
| 4 | | | | |
| 5 | t-shut-in | 24 | hours | |
| 6 | | | | |
| 7 | Water tracer (stage N) recovered, (Slide 22 1st left equation) | 0.000418 | lbs | |
| 8 | Oil tracer (stage N) recovered, (Slide 22 1st right equation) | 0.000522 | lbs | |
| 9 | Water tracer release rate (@t) | 3.8E-05 | lbs/lbs/day | |
| 10 | Oil tracer release rate (@t) | 4.25E-05 | lbs/lbs/day | |
| 11 | Water tracer (N) contacted by flowing fluid, (Slide 22 Equation 2) or second equation line) | 11 | lbs | |
| 12 | Oil tracer (N) contacted by flowing fluid, (Slide 22 Equation 3) or third equation line) | 12.27 | lbs | |
| 13 | Total water tracer N particulate contacted by flowing fluid | 20 | lbs | |
| 14 | Total oil tracer N particulate contacted by flowing fluid | 27.27273 | lbs | |
| 15 | | | | |
| 16 | WOR (Slide 22 last equation) | 1.222222 | | |
| 17 | | | | |
| 18 | Total wellbore volume between tracer N and N+1 | 17.36111 | bbls | Sheet 1, Row 13 |
| 19 | | | | |
| 20 | V_wellbore oil volume between tracer N and N+1 on average | 7.8125 | bbls | (Slide 25 equation to the right) |
| 21 | V_wellbore water volume between tracer N and N+1 on average | 9.548611 | bbls | (Slide 25 equation to the left) |
| 22 | | | | |
| 23 | Δt for water tracer observed at surface | 32 | minutes | |
| 24 | Δt for oil tracer observed at surface | 35 | minutes | |
| 25 | | | | |
| 26 | Water flow rate between tracer N and N+1 | 429.6875 | bbls/day | (Slide 24, 1st equation) |
| 27 | Oil flow rate between tracer N and N+1 | 321.4286 | bbls/day | (Slide 24, 2st equation) |
| 28 | | | | |

FIG. 7E

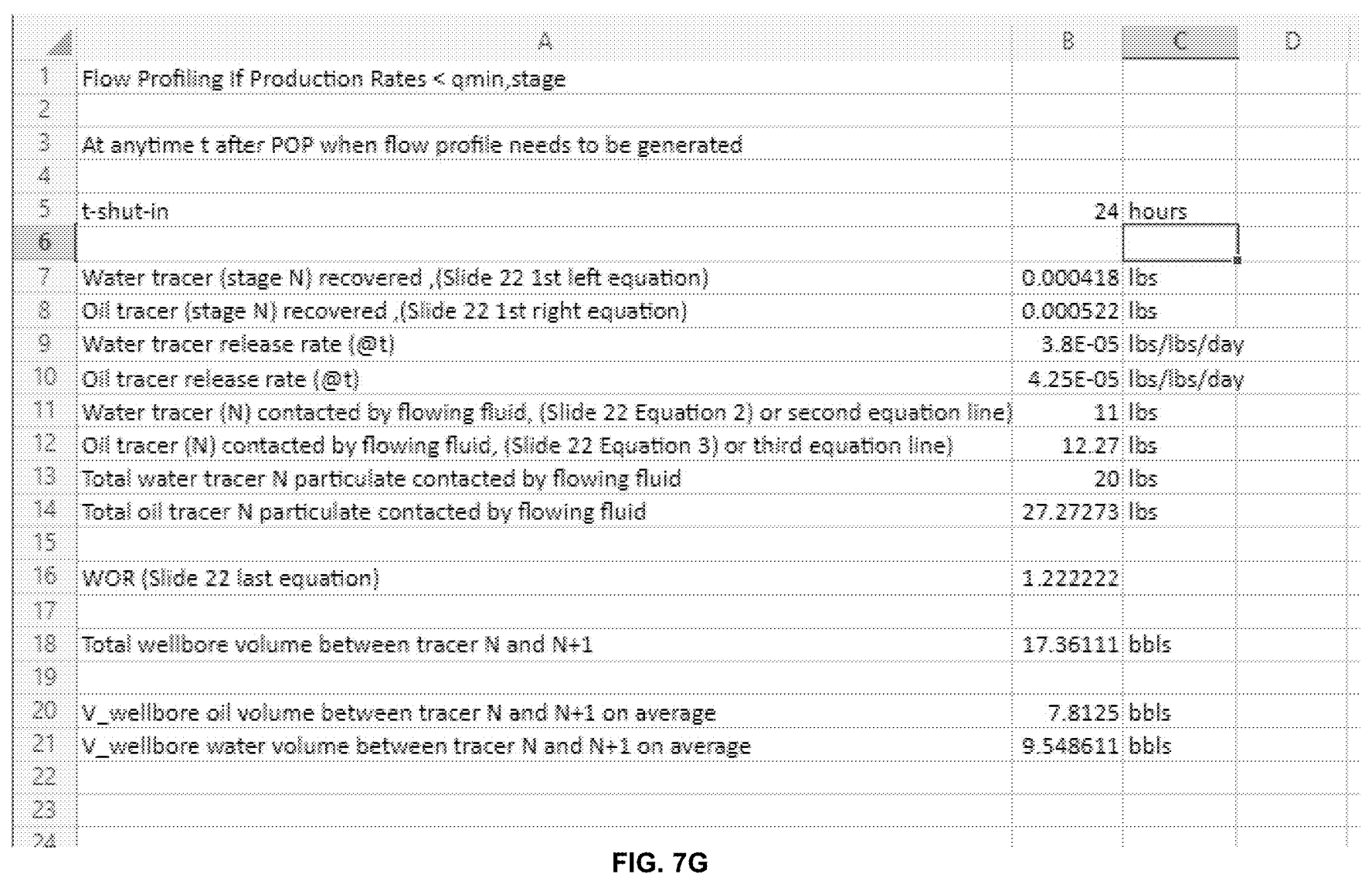

|   | A | B | C | D |
|---|---|---|---|---|
| 1 | Flow Profiling if Production Rates < qmin,stage | | | |
| 2 | | | | |
| 3 | At anytime t after POP when flow profile needs to be generated | | | |
| 4 | | | | |
| 5 | t-shut-in | 24 | hours | |
| 6 | | | | |
| 7 | Water tracer (stage N) recovered ,(Slide 22 1st left equation) | 0.000418 | lbs | |
| 8 | Oil tracer (stage N) recovered ,(Slide 22 1st right equation) | 0.000522 | lbs | |
| 9 | Water tracer release rate (@t) | 3.8E-05 | lbs/lbs/day | |
| 10 | Oil tracer release rate (@t) | 4.25E-05 | lbs/lbs/day | |
| 11 | Water tracer (N) contacted by flowing fluid, (Slide 22 Equation 2) or second equation line) | 11 | lbs | |
| 12 | Oil tracer (N) contacted by flowing fluid, (Slide 22 Equation 3) or third equation line) | 12.27 | lbs | |
| 13 | Total water tracer N particulate contacted by flowing fluid | 20 | lbs | |
| 14 | Total oil tracer N particulate contacted by flowing fluid | 27.27273 | lbs | |
| 15 | | | | |
| 16 | WOR (Slide 22 last equation) | 1.222222 | | |
| 17 | | | | |
| 18 | Total wellbore volume between tracer N and N+1 | 17.36111 | bbls | |
| 19 | | | | |
| 20 | V_wellbore oil volume between tracer N and N+1 on average | 7.8125 | bbls | |
| 21 | V_wellbore water volume between tracer N and N+1 on average | 9.548611 | bbls | |
| 22 | | | | |
| 23 | | | | |
| 24 | | | | |

FIG. 7G

900 obtain produced fluid samples comprising unique particulate tracers from a wellbore drilled into a subterranean formation, wherein the unique particulate tracers are pumped in at least one stage pair during a hydraulic fracturing operation performed in the subterranean formation, and wherein the unique particulate tracers are pumped only in a fraction of each stage such that a substantial portion of the unique particulate tracers are placed in a near wellbore region of the subterranean formation proximate to the wellbore, and wherein at least one unique particulate tracer is pumped in the fraction of each stage, and wherein each unique particulate tracer corresponds to an oil phase, a water phase, or a gas phase 901 obtain a tracer concentration history for each unique particulate tracer 905 determine a wellbore volume for the stage pair 910 determine a flow profile for the wellbore for each phase indicative of flow contribution for each stage pair and stages in between each stage pair using the wellbore volume and the corresponding tracer concentration histories 915 check by obtaining a production history for the wellbore; summing all flow contributions for each stage pair for each phase; and comparing the sums and the production history to constraint total flow contribution for each phase 920 smooth a tracer concentration history for a specific unique particulate tracer before c) of step 915 to reduce noise (e.g., reduce points that show large variations ups and/or downs); and utilize the smoothed tracer concentration history for the specific unique particulate tracer in c) of step 915 925 generate, on the graphical user interface, a representation of the flow profile for the wellbore for each phase indicative of the flow contribution for each stage pair and stages within each stage pair; and display, via the graphical user interface, the representation 930

FIG. 9

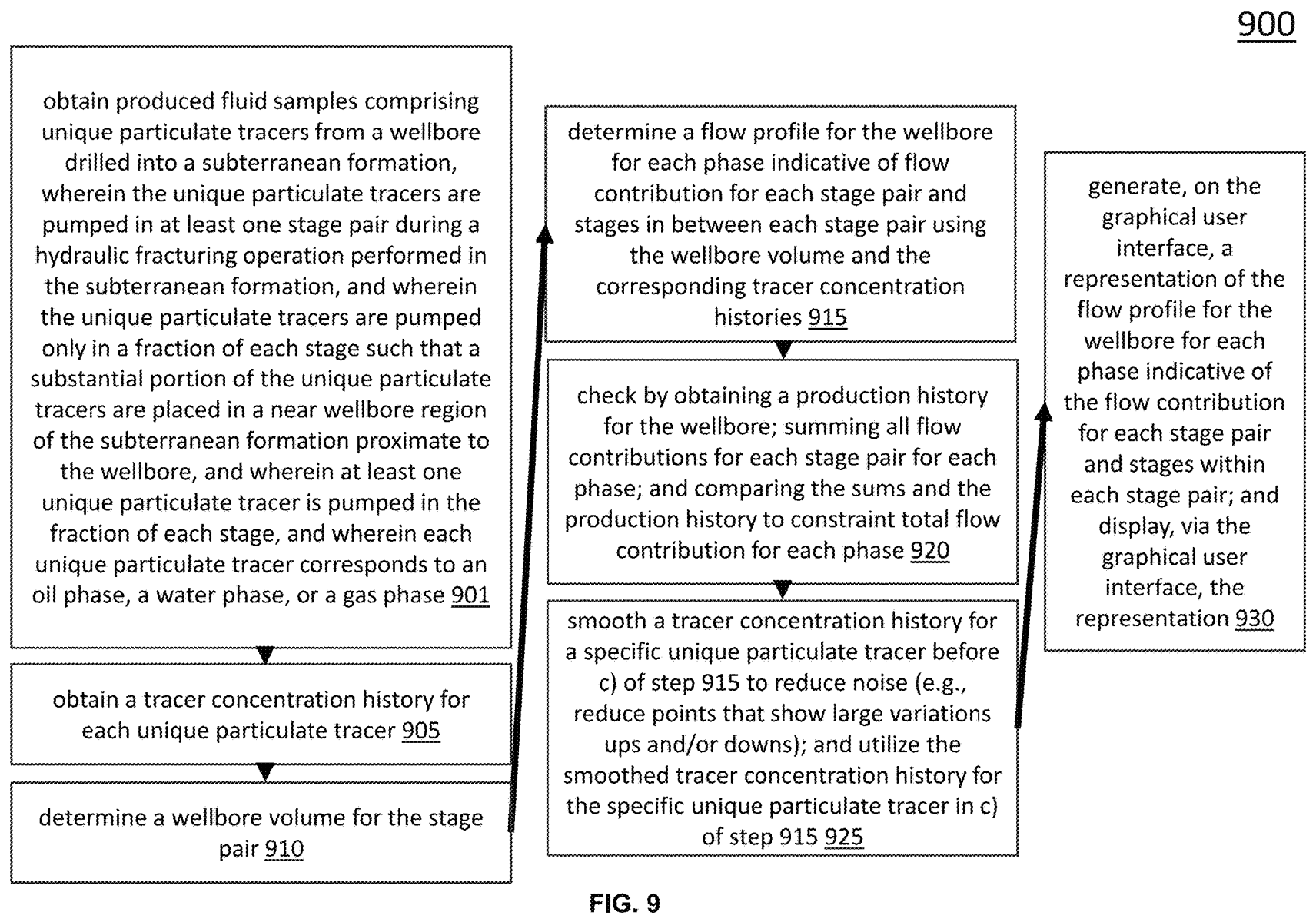

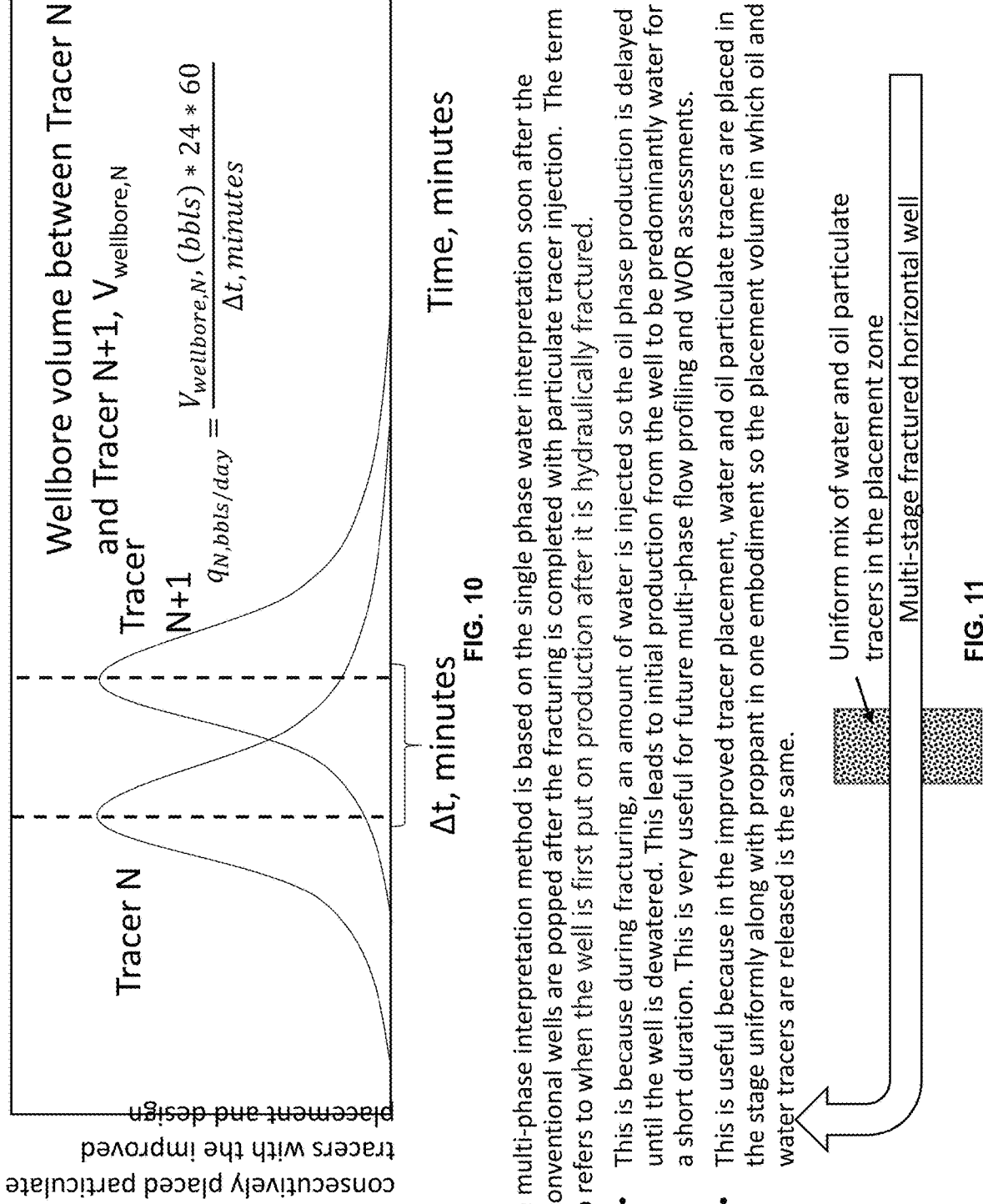

Wellbore volume between Tracer N and Tracer N+1, $V_{wellbore,N}$

$$q_{N,bbls/day} = \frac{V_{wellbore,N}\,(bbls) * 24 * 60}{\Delta t,\, minutes}$$

Tracer N+1

Tracer N

Tracer conc. @ surface from two consecutively placed particulate tracers with the improved placement and design $\Delta t$, minutes Time, minutes

FIG. 10

The multi-phase interpretation method is based on the single phase water interpretation soon after the unconventional wells are popped after the fracturing is completed with particulate tracer injection. The term pop refers to when the well is first put on production after it is hydraulically fractured.

- This is because during fracturing, an amount of water is injected so the oil phase production is delayed until the well is dewatered. This leads to initial production from the well to be predominantly water for a short duration. This is very useful for future multi-phase flow profiling and WOR assessments.

- This is useful because in the improved tracer placement, water and oil particulate tracers are placed in the stage uniformly along with proppant in one embodiment so the placement volume in which oil and water tracers are released is the same.

•

Uniform mix of water and oil particulate tracers in the placement zone

Multi-stage fractured horizontal well

FIG. 11

- Right after POP: The entire placement volume for each tracer is predominantly occupied by single phase water. The total water tracer mass recovered is a function of the amount of tracer placed in contact with water close to the wellbore affecting the flow profiling.

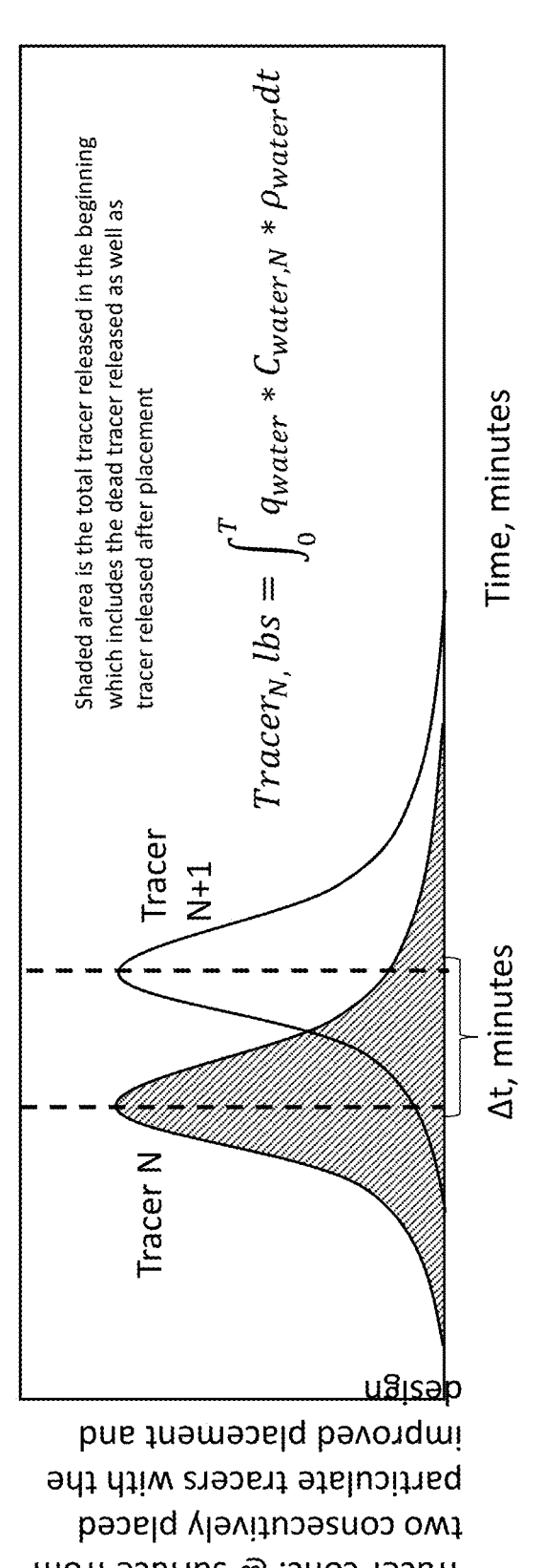

Shaded area is the total tracer released in the beginning which includes the dead tracer released as well as tracer released after placement $$Tracer_N, lbs = \int_0^T q_{water} * C_{water,N} * \rho_{water} \cdot dt$$

Tracer N+1

Tracer N $\Delta t$, minutes

Time, minutes

Tracer conc. @ surface from two consecutively placed particulate tracers with the improved placement and design

FIG. 12

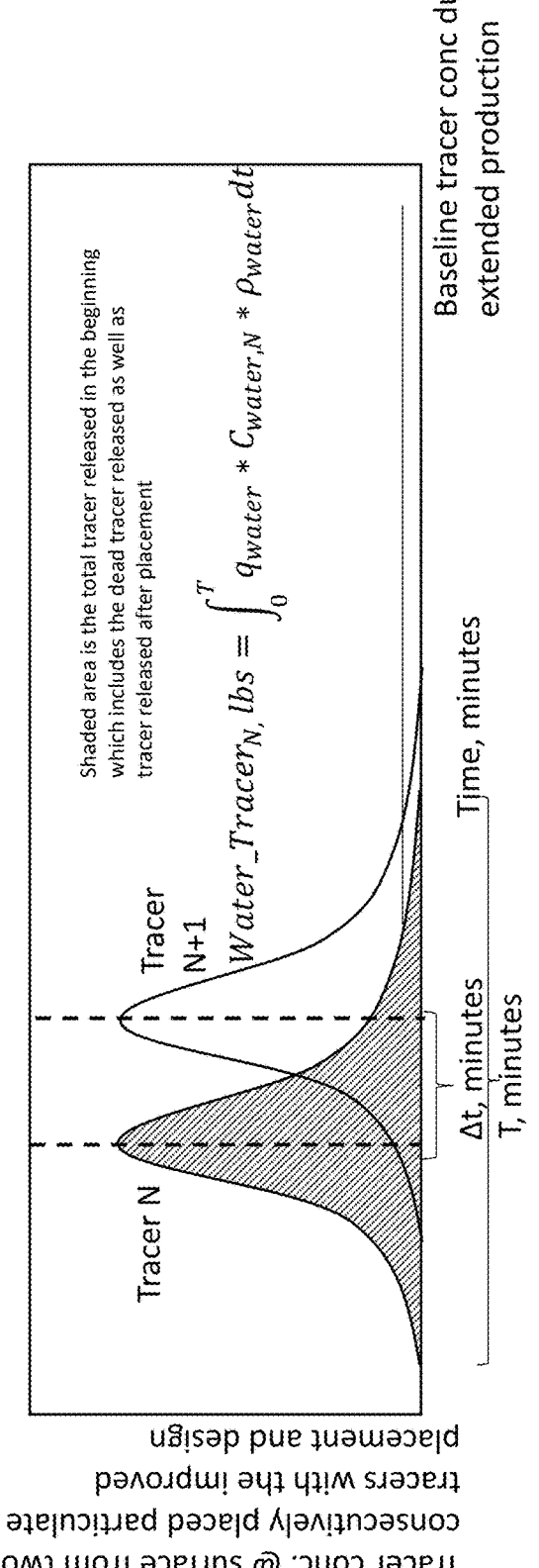

The below relationships also help verify that tracer mass placed and determined from flowback data agrees.

Shaded area is the total tracer released in the beginning which includes the dead tracer released as well as tracer released after placement $$Water\_Tracer_N, lbs = \int_0^T q_{water} * c_{water,N} * \rho_{water} dt$$

Baseline tracer conc during extended production

Tracer N+1

Tracer N $\Delta t$, minutes
$T$, minutes

Time, minutes

Tracer conc. @ surface from two consecutively placed particulate tracers with the improved placement and design $Water\_Tracer_N, lbs$ $Total\ Water\ tracer\ N\ particulate, contacted\ by\ flowing\ fluid, lbs@(t=0) = \dfrac{Water\_Tracer_N, lbs}{(dead\ tracer\ portion + tracer\ release\ rate(t=0) * Shutin\ time\ before\ POP)}$ $Total\ Water\ tracer\ N\ particulate, contacted\ by\ flowing\ fluid, lbs@(t=0) \leq Design\ water\ particulate\ tracer\ mass\ N, /injected\ lbs$ $Total\ Oil\ tracer\ N\ particulate, contacted\ by\ flowing\ fluid, lbs@(t=0) =$
$Design\ oil\ particulate\ tracer\ mass\ N, /injected\ lbs$ $Total\ Water\ tracer\ N\ particulate, contacted\ by\ flowing\ fluid, lbs@(t=0) * Design\ water\ particulate\ tracer\ mass\ N, /injected\ lbs$
$Design\ water\ particulate\ tracer\ mass\ N, /injected\ lbs$

FIG. 13

- At any time (t) after the well is popped, if the well is shut, the tracer mass for water and oil from stage N is calculated $$Water\_Tracer_N, lbs = \int_{t}^{t+T} q_{water} * C_{water,N} * \rho_{water} dt \quad Oil\_Tracer_N, lbs = \int_{t}^{t+T} q_{oil} * C_{oil,N} * \rho_{oil} dt$$

$$Water\ tracer\ N, contacted\ by\ flowing\ fluid, lbs = \frac{Water\_Tracer_N, lbs}{(tracer\ release\ rate(t) * Shutin\ time)}$$

$$Oil\ tracer\ N, contacted\ by\ flowing\ fluid, lbs = \frac{Oil\_Tracer_N, lbs}{(tracer\ release\ rate(t) * Shutin\ time)}$$

For stage with oil and water particulate tracers N placed in the improved configuration, the pressure drop across the stage is the same for both oil and water phase as well as the same fracture properties and for oil and water flowing through fractures a straight line relative permeability is also a valid assumption which allows us to make the following deduction:

$$WOR, (Nth\ stage) = \frac{Water\ tracer\ N, contacted\ by\ flowing\ fluid, lbs * Total\ Oil\ tracer\ N, contacted\ by\ flowing\ fluid, lbs}{Total\ Water\ tracer\ N, contacted\ by\ flowing\ fluid, lbs * Oil\ tracer\ N, contacted\ by\ flowing\ fluid, lbs}$$

FIG. 14

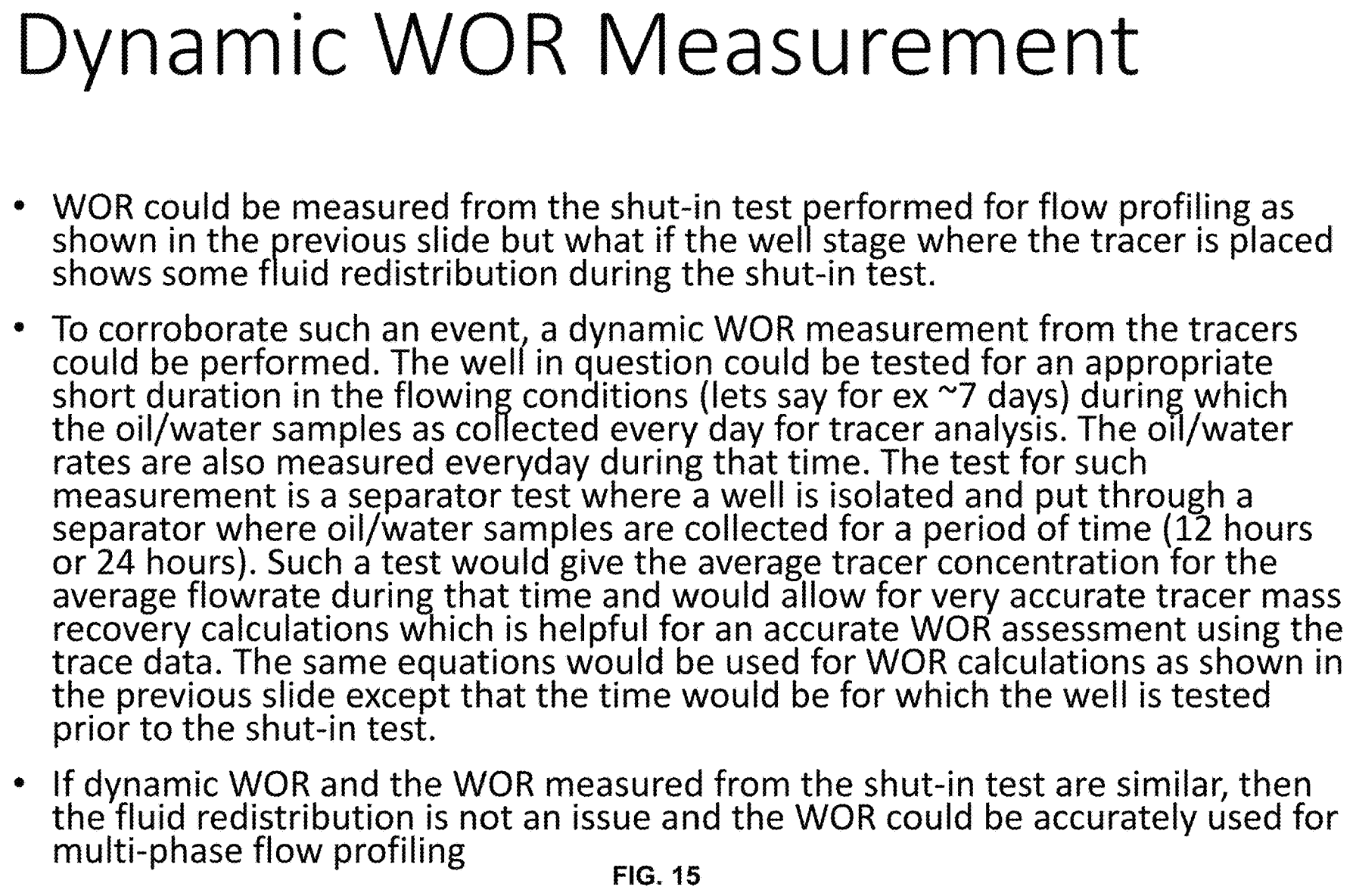

Dynamic WOR Measurement

- WOR could be measured from from the shut-in test performed for flow profiling as shown in the previous slide but what if the well stage where the tracer is placed shows some fluid redistribution during the shut-in test.

- To corroborate such an event, a dynamic WOR measurement from the tracers could be performed. The well in question could be tested for an appropriate short duration in the flowing conditions (lets say for ex ~7 days) during which the oil/water samples as collected every day for tracer analysis. The oil/water rates are also measured everyday during that time. The test for such measurement is a separator test where a well is isolated and put through a separator where oil/water samples are collected for a period of time (12 hours or 24 hours). Such a test would give the average tracer concentration for the average flowrate during that time and would allow for very accurate tracer mass recovery calculations which is helpful for an accurate WOR assessment using the trace data. The same equations would be used for WOR calculations as shown in the previous slide except that the time would be for which the well is tested prior to the shut-in test.

- If dynamic WOR and the WOR measured from the shut-in test are similar, then the fluid redistribution is not an issue and the WOR could be accurately used for multi-phase flow profiling

FIG. 15

Multi-phase Flow Profiling Interpretation

- With the improved placement and design, the tracer response at the surface could be interpreted like wellbore solid tracers for flow profiling

Multi-phase Flow Profiling Interpretation

- $V_{wellbore\_water,N}$, $(bbls)$ and $V_{wellbore\_oil\ N}$, $(bbls)$ is used and would be a function of the WOR in the wellbore and WOR for a stage in which tracers are placed is calculated as shown previously.

- We have to assume that the WOR calculated for stage N is on average the same for the section between tracer (N) and tracer (N+1) placement and thus the it gives $$\frac{V_{wellbore\_water,N}}{V_{wellbore\_oil\ N}} = WOR$$

- And combining it with the flowrate equations previously gives you the phase flowrates per lateral section

FIG. 16B

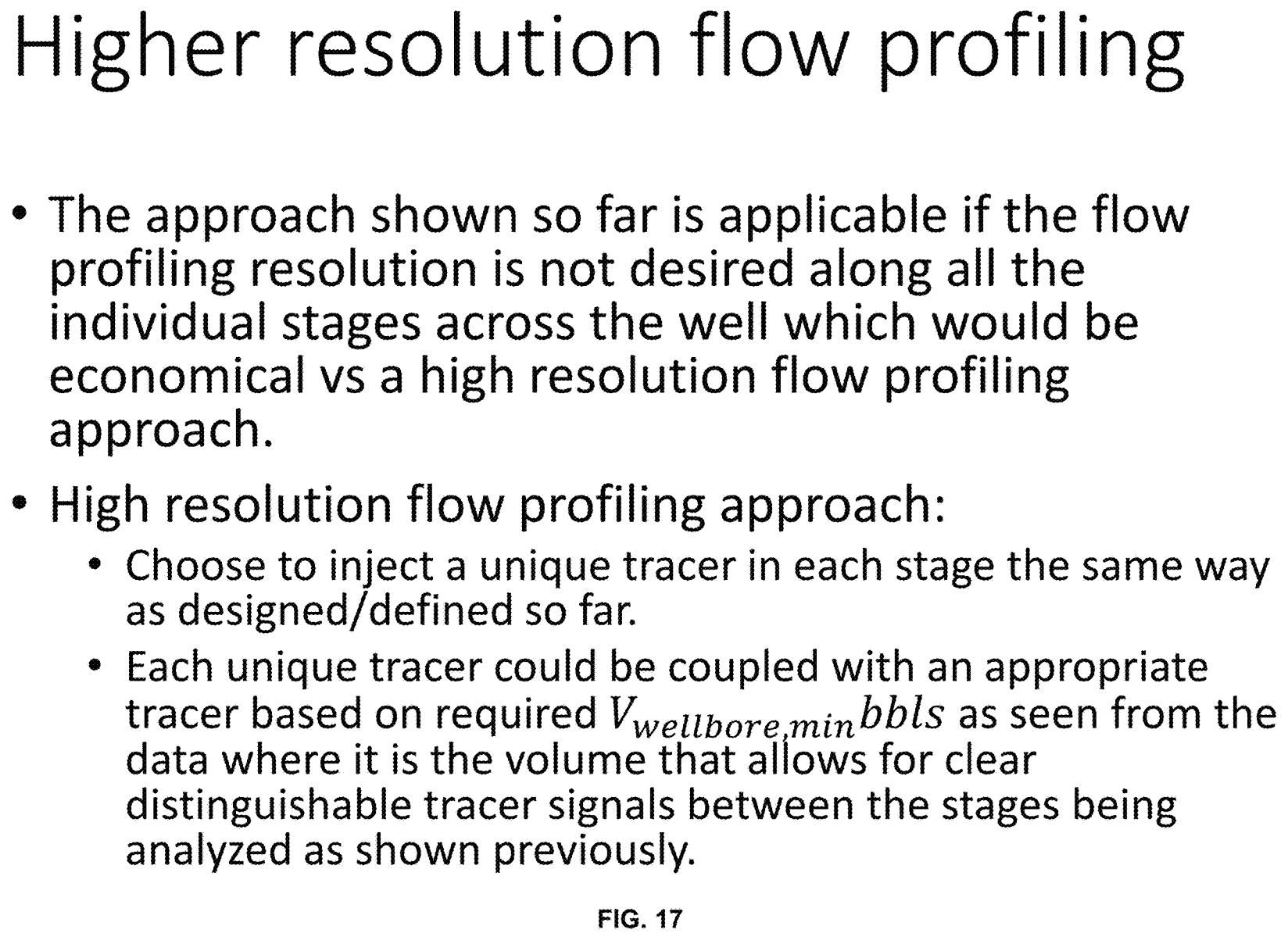

Higher resolution flow profiling

- The approach shown so far is applicable if the flow profiling resolution is not desired along all the individual stages across the well which would be economical vs a high resolution flow profiling approach.

- High resolution flow profiling approach:

- Choose to inject a unique tracer in each stage the same way as designed/defined so far.

- Each unique tracer could be coupled with an appropriate tracer based on required $V_{wellbore,min}bbls$ as seen from the data where it is the volume that allows for clear distinguishable tracer signals between the stages being analyzed as shown previously.

FIG. 17

Flow Profiling If Production Rates < $q_{min,stage}$

- In such a case, the tracer signals seen at the surface are not separated as expected and more dispersed as shown below and the signals might overlap and intersect as well, so the flow profiling method presented before may be adjusted.

Flow Profiling If Production Rates $< q_{min,stage}$

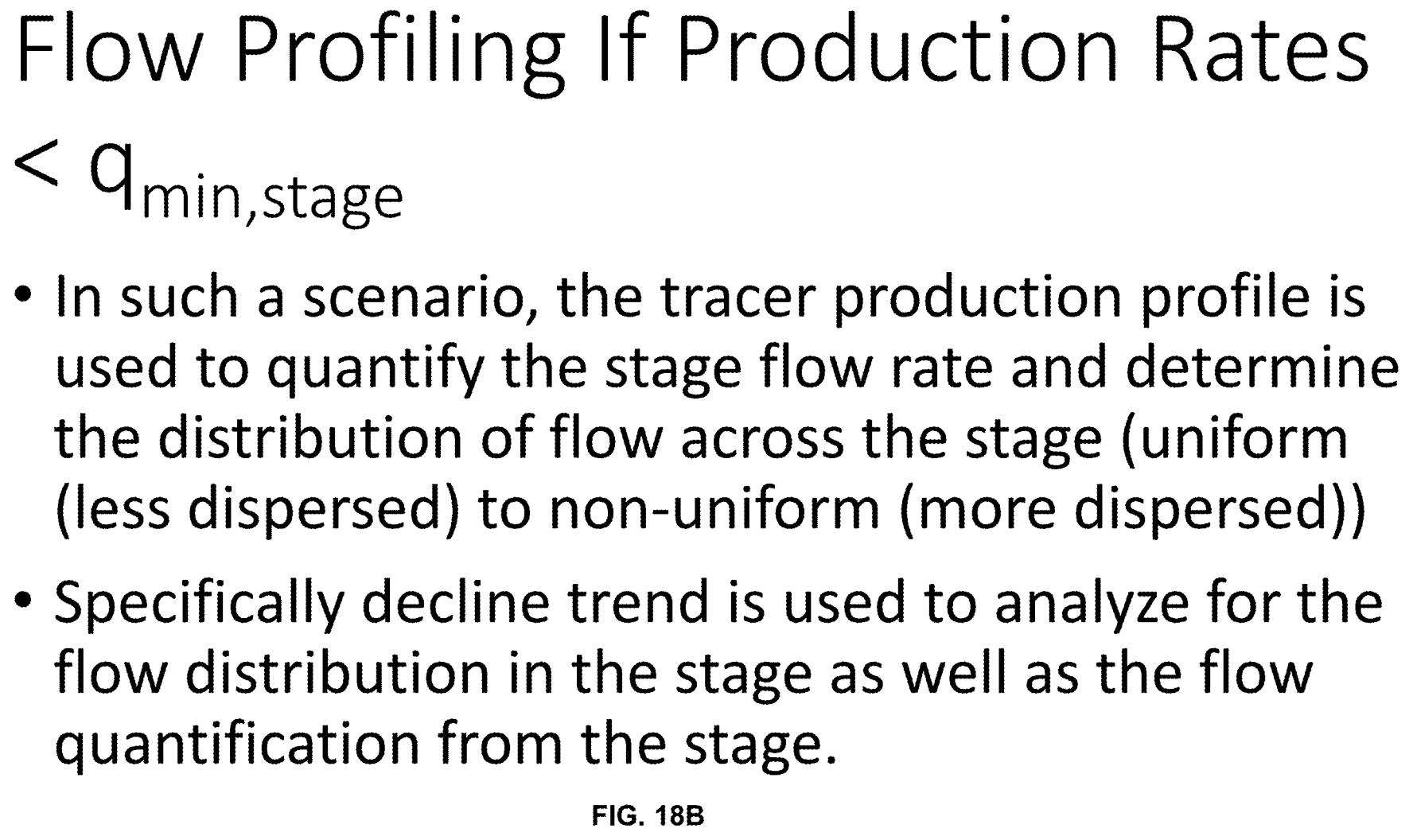

- In such a scenario, the tracer production profile is used to quantify the stage flow rate and determine the distribution of flow across the stage (uniform (less dispersed) to non-uniform (more dispersed))

- Specifically decline trend is used to analyze for the flow distribution in the stage as well as the flow quantification from the stage.

FIG. 18B

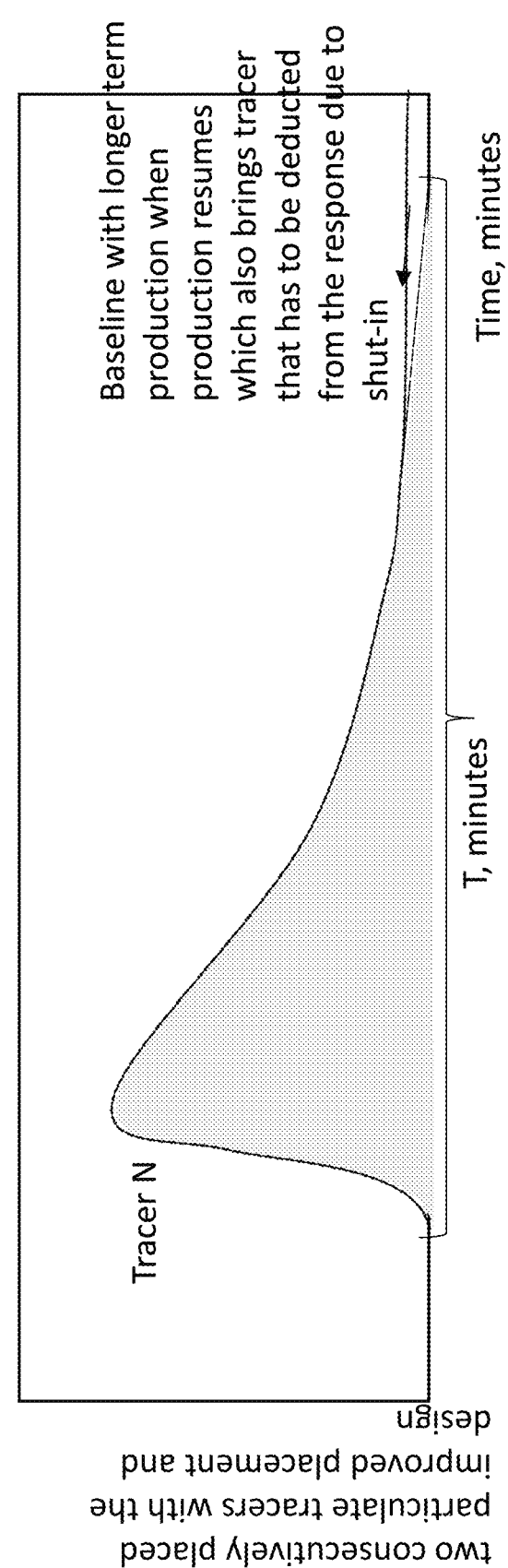

Flow Profiling If Production Rates < $q_{min,stage}$

Tracer N

Baseline with longer term production when production resumes which also brings tracer that has to be deducted from the response due to shut-in T, minutes Time, minutes Tracer conc. @ surface from two consecutively placed particulate tracers with the improved placement and design

- The shaded area is the built tracer cloud produced due to shut-in and the tracer mass recovered highlighted under the shaded area is a function of
  - Amount of tracer in contact with the fluid vs injected/original tracer in contact
  - Tracer release rate at the time of the test
  - The duration of the shut-in
- This is done for both oil and water phases

FIG. 18C

Effective Tracer Occupied Volume @ time t

- At any time (t) after the well is popped, if the well is shut, the tracer mass for water and oil from stage N is calculated $$Water\_Tracer_N, lbs = \int_t^{t+T} q_{water} * C_{water,N} * \rho_{water} dt \quad Oil\_Tracer_N, lbs = \int_t^{t+T} q_{oil} * C_{oil,N} * \rho_{oil} dt$$

$$Water\ tracer\ particulate\ N, contacted\ by\ flowing\ fluid, lbs = \frac{Water\_Tracer_N, lbs}{(tracer\ release\ rate(t) * Shutin\ time)}$$

$$Oil\ tracer\ N\ particulate, contacted\ by\ flowing\ fluid, lbs = \frac{Oil\_Tracer_N, lbs}{(tracer\ release\ rate(t) * Shutin\ time)}$$

Effective tracer occupied volume fraction contributing to the tracer flow @ time t. We use water tracer because the baseline contacted volume occupied by tracer is calculated based right after frac completion where most of the frac is occupied by injected completion fluid which is water $$Effective\ water\ tracer\ occupied\ pore\ volume\ fraction = \frac{Water\ tracer\ particulte\ N, contacted\ by\ flowing\ fluid, lbs}{Total\ Water\ tracer\ particulate\ N, contacted\ by\ flowing\ fluid, lbs}$$

FIG. 19A

Effective Tracer Occupied Volume @ time t

- Original tracer occupied volume is based in the original proppant mass tagged (*Tagged proppant mass, lbs*) with tracers which is by design. That proppant mass tagged with tracer holds the pore volume which is equal to $V_p$, *bbls*. The effective tracer occupied pore volume at time t =0 is what the baseline volume for all future flow profiling calculations.

$$Effective\ water\ V_p, bbls\ @(t=0) = \frac{Total\ Water\ particulate\ tracer\ N, contacted\ by\ flowing\ fluid, lbs\ @\ (t=0)}{Design\ water\ particulate\ tracer\ mass\ N\ required./injected\ lbs} * V_p, bbls$$

$$Effective\ oil\ V_p, bbls\ @(t=0) = \frac{Total\ oil\ tracer\ N, contacted\ by\ flowing\ fluid, lbs\ @\ (t=0)}{Design\ oil\ particulate\ tracer\ mass\ N\ required./injected\ lbs} * V_p, bbls$$

- Effective tracer occupied pore volume @ time t $$Effective\ water\ V_p, bbls\ @(t) = \frac{Water\ tracer\ particulate\ N, contacted\ by\ flowing\ fluid, lbs\ @\ (t)}{Total\ Water\ particulate\ tracer\ N, contacted\ by\ flowing\ fluid, lbs\ @(t=0)} * Effective\ water\ V_p, bbls\ @(t=0)$$

$$Effective\ oil\ V_p, bbls\ @(t) = \frac{oil\ tracer\ particulate\ N, contacted\ by\ flowing\ fluid, lbs\ @\ (t)}{Total\ oil\ particulate\ tracer\ N, contacted\ by\ flowing\ fluid, lbs\ @(t=0)} * Effective\ oil\ V_p, bbls\ @(t=0)$$

FIG. 19B

Effective Tracer Swept Volume

- The effective tracer occupied volume at time t should be equal to the tracer swept volume which is calculated from the tracer decline trend using the following equation $$V_{Tracer_{swept_{water_{stage}},N}}(t) = \int_0^T q_{water_{stage},N}(t)\left(1 - F_{water_{Tracer_{stage}},N}(t)\right)dt$$

$$F_{water_{Tracer_{stage}},N}(t) = 1 - \frac{C_{water_{stage},N}(t)}{f_{stage,N_{proportion_{water}}}(t)\,C_{initial_{water_{stage}},N}\,@t}$$

$$f_{stage,N_{proportion_{water}}}(t) = \frac{q_{water_{stageN}}}{q_{water\_total}}$$

$$V_{Tracer_{swept_{oil_{stage}},N}}(t) = \int_0^T q_{oil_{\ stage},N}(t)\left(1 - F_{oil_{Tracer_{stage}},N}(t)\right)dt$$

$$F_{oil_{Tracer_{stage}},N}(t) = 1 - \frac{C_{oil_{stage},N}(t)}{f_{stage,N_{proportion_{oil}}}(t)\,C_{initial_{oil_{stage}},N}\,@t}$$

$$f_{stage,N_{proportion_{oil}}}(t) = \frac{q_{oil\ stageN}}{q_{oil\_total}}$$

FIG. 20A

Effective Tracer Swept Volume

- Simplifying the previous equations gives $$V_{Tracerswept_{waterstage},N}(t) = \int_0^t q_{water\_total}(t) \left( \frac{C_{water_{stage},N}(t)}{C_{initialwater_{stage},N} @t} \right) dt$$

$$V_{Tracerswept_{oilstage},N}(t) = \int_0^t q_{oil\_total}(t) \left( \frac{C_{oil_{stage},N}(t)}{C_{initialoil_{stage},N} @t} \right) dt$$

- These tracer swept volumes are equal to the effective tracer particulate volumes calculated previously. We use these to calculate $C_{initialwater_{stage},N} @t$ and $C_{initialoil_{stage},N} @t$ which is used to calculate the flow coming from stage N or flow profiling

FIG. 20B

$$C_{initial_{water_{stage}},N} @t \text{ and}$$

$$C_{initial_{oil\ stage},N} @t$$

$$C_{initial_{water_{stage}},N} @t = \frac{\int_0^t q_{water\_total}(t) C_{water_{stage},N}(t)\, dt}{Effective\ water\ V_p,\ bbls\ @(t)}$$

$$C_{initial_{oil\ stage},N} @t = \frac{\int_0^t q_{oil\_total}(t) C_{oil_{stage},N}(t)\, dt}{Effective\ oil\ V_p,\ bbls\ @(t)}$$

FIG. 20C

Flow Quantification from Stage N $$F_{water_{Tracer_{stage},N}}(t) = 1 - \frac{C_{water_{stage},N}(t)}{f_{stage,N_{proportion\_water}}(t) C_{initial_{water_{stage},N}} @t}$$

$$F_{oil_{Tracer_{stage},N}}(t) = 1 - \frac{C_{oil_{stage},N}(t)}{f_{stage,N_{proportion\_oil}}(t) C_{initial_{oil_{stage},N}} @t}$$

- Right at the time after the intermittent shut-in ends at time t and production begins again, the above equation is equal to zero which allows for estimation of $f_{stage,N_{fraction\_water}}$ and $f_{stage,N_{fraction\_oil}}$ $$f_{stage,N_{proportion_{water}}}(t) = \frac{q_{water_{stageN}}}{q_{water\_total}} = \frac{C_{water_{stage},N}(@start\ of\ prod\ after\ shutin)}{C_{initial_{water_{stage},N}} @t}$$

$$f_{stage,N_{proportion_{oil}}}(t) = \frac{q_{oil\ \ stageN}}{q_{oil\_total}} = \frac{C_{oil_{stage},N}(@start\ of\ prod\ after\ shutin)}{C_{initial_{oil_{stage},N}} @t}$$

FIG. 21

$$C_{water_{stage},N}\,(@start\ of\ prod\ after\ shutin)$$

$$C_{oil_{stage},N}\,(@start\ of\ prod\ after\ shutin)$$

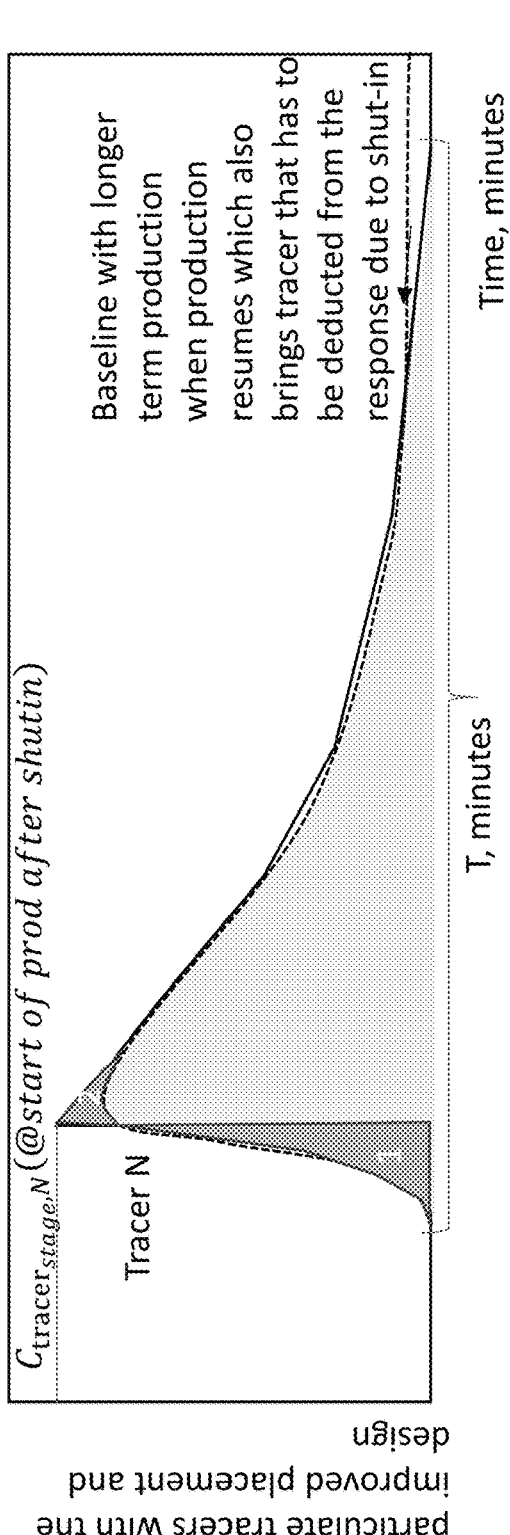

FIG. 22

- Due to dispersion in the wellbore the initial signal might start from zero as shown above and get to a peak and then decline which without wellbore dispersion would start at a peak value and the decline

- The $C_{water_{stage},N}\,(@start\ of\ prod\ after\ shutin)$ and $C_{oil_{stage},N}\,(@start\ of\ prod\ after\ shutin)$ is determined by extrapolating the tracer concentration back to a point such that the two grey areas marked 1 and 2 are equal.

2500 obtain a tracer concentration history for each unique particulate tracer in produced fluid samples from a wellbore drilled into a subterranean formation 2505 obtain a production history for the wellbore 2510 smooth a tracer concentration history for a specific unique particulate tracer before c) of step 2515 and d) of step 2520 to reduce noise; and utilize the smoothed tracer concentration history for the specific unique particulate tracer in c) of step 2515 and d) of step 2520 2535 determine a mean residence time for each unique particulate tracer using the corresponding tracer concentration history 2515 determine a contact volume proxy for each unique particulate tracer using the production history and the corresponding tracer concentration history 2520 determine a flow profile for the wellbore for each phase indicative of flow contribution of each stage, each stage group, or any combination thereof by using the corresponding mean residence times and the corresponding contact volume proxies 2525 generate a representation of the flow profile for the wellbore for each phase indicative of the flow contribution of each stage, each stage group, or any combination thereof, and display the representation 2530

FIG. 25

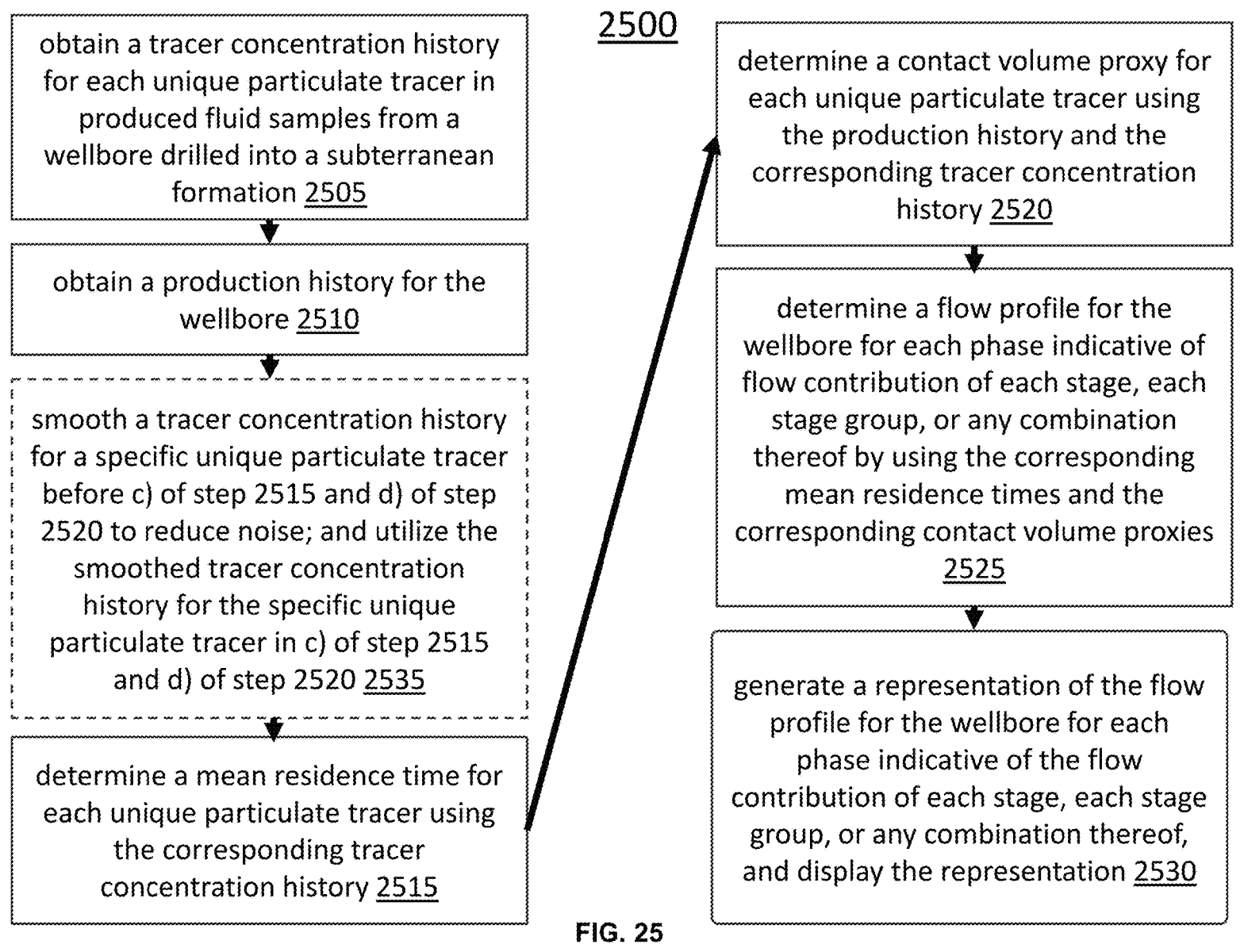

2700 determine a contact volume proxy for each unique particulate tracer using the production history and the corresponding tracer concentration history 2520 determine a flow profile for the wellbore for each phase indicative of flow contribution of each stage, each stage group, or any combination thereof by using the corresponding mean residence times and the corresponding contact volume proxies 2525 generate a representation of the flow profile for the wellbore for each phase indicative of the flow contribution of each stage, each stage group, or any combination thereof, and display the representation 2530 obtain a tracer concentration history for each unique particulate tracer in produced fluid samples from a wellbore drilled into a subterranean formation 2505 obtain a production history for the wellbore 2510 smooth a tracer concentration history for a specific unique particulate tracer before c) of step 2515 and d) of step 2520 to reduce noise; and utilize the smoothed tracer concentration history for the specific unique particulate tracer in c) of step 2515 and d) of step 2520 2535 determine a mean residence time for each unique particulate tracer using the corresponding tracer concentration history 2515 pump at least one unique particulate tracer throughout each stage, each stage group, or any combination thereof during a hydraulic fracturing operation performed in the subterranean formation 2705 shut-in the wellbore for a period of time to cause tracer clouds to form in the subterranean formation for at least a portion of the unique particulate tracers that were pumped throughout the stages, the stage groups, or any combination thereof 2710 flow back the wellbore to cause produced fluid from the wellbore after the shut-in period 2715 obtain produced fluid samples comprising unique particulate tracers from a wellbore drilled into a subterranean formation 2720 analyze the produced fluid samples obtained from the produced fluid to generate the tracer concentration history for each unique particulate tracer (e.g., lab) 2725 obtain a production history for the wellbore (e.g., field) 2730

FIG. 27

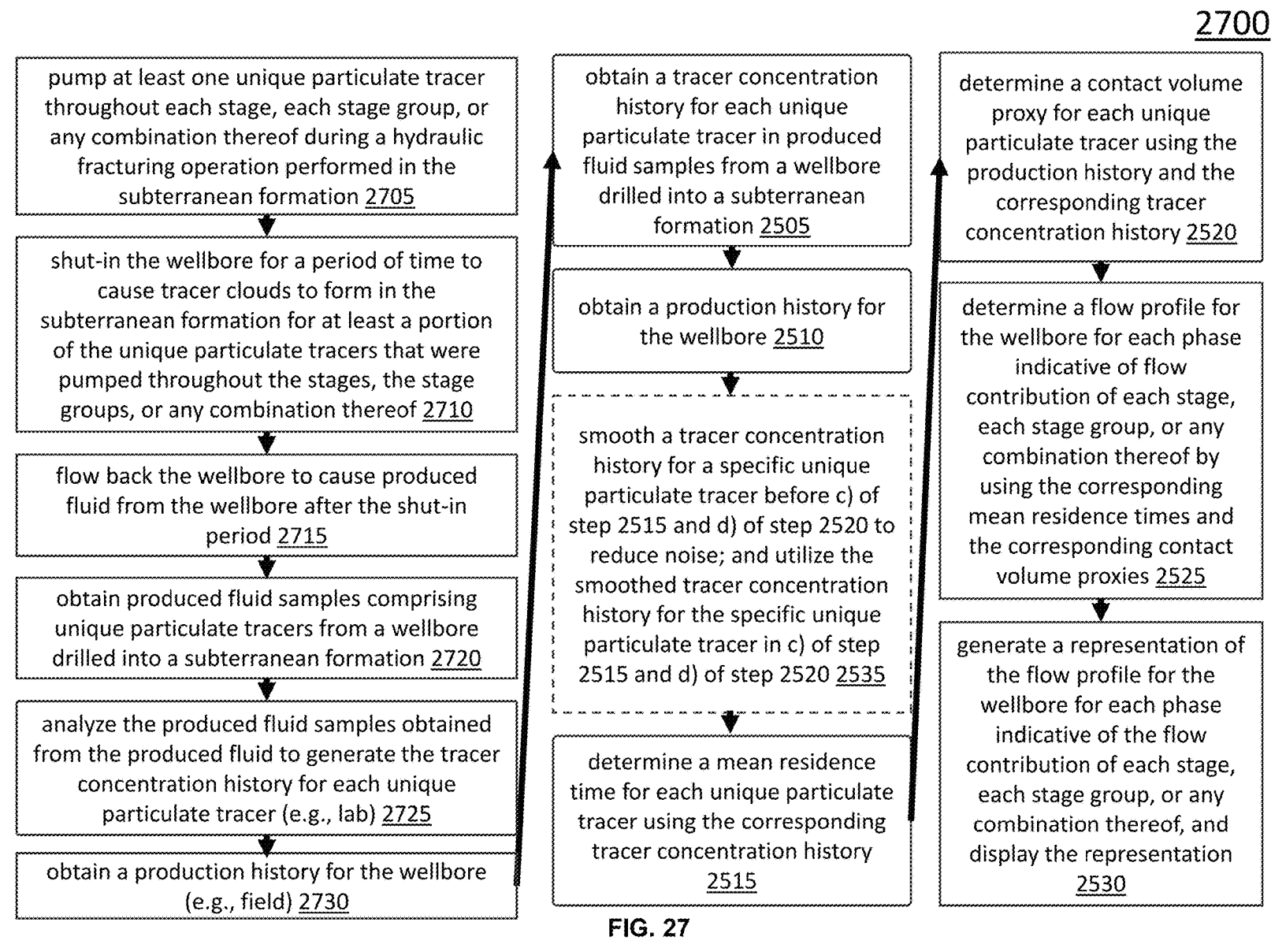

Shut-in builds a tracer cloud in the subterranean formation, which gets produced on the flowback

3000 determine a normalization factor for each unique particulate tracer using the corresponding tracer concentration history and optionally the production history 3020 determine a normalized decline rate for each unique particulate tracer using the corresponding decline rate and the corresponding normalization factor 3025 determine a flow profile for the wellbore for each phase indicative of flow contribution of each stage, each stage group, or any combination thereof by using the corresponding normalized decline rates 3030 generate a representation of the flow profile for the wellbore for each phase indicative of the flow contribution of each stage, each stage group, or any combination thereof, and display the representation 3035 obtain a tracer concentration history for each unique particulate tracer in produced fluid samples from a wellbore drilled into a subterranean formation 3005 obtain a production history for the wellbore 3010 smooth a tracer concentration history for a specific unique particulate tracer before c) of step 3015 and d) of step 3020 to reduce noise; and utilize the smoothed tracer concentration history for the specific unique particulate tracer in c) of step 3015 and d) of step 3020 3040 determine a decline rate for each unique particulate tracer using the corresponding tracer concentration history 3015

FIG. 30

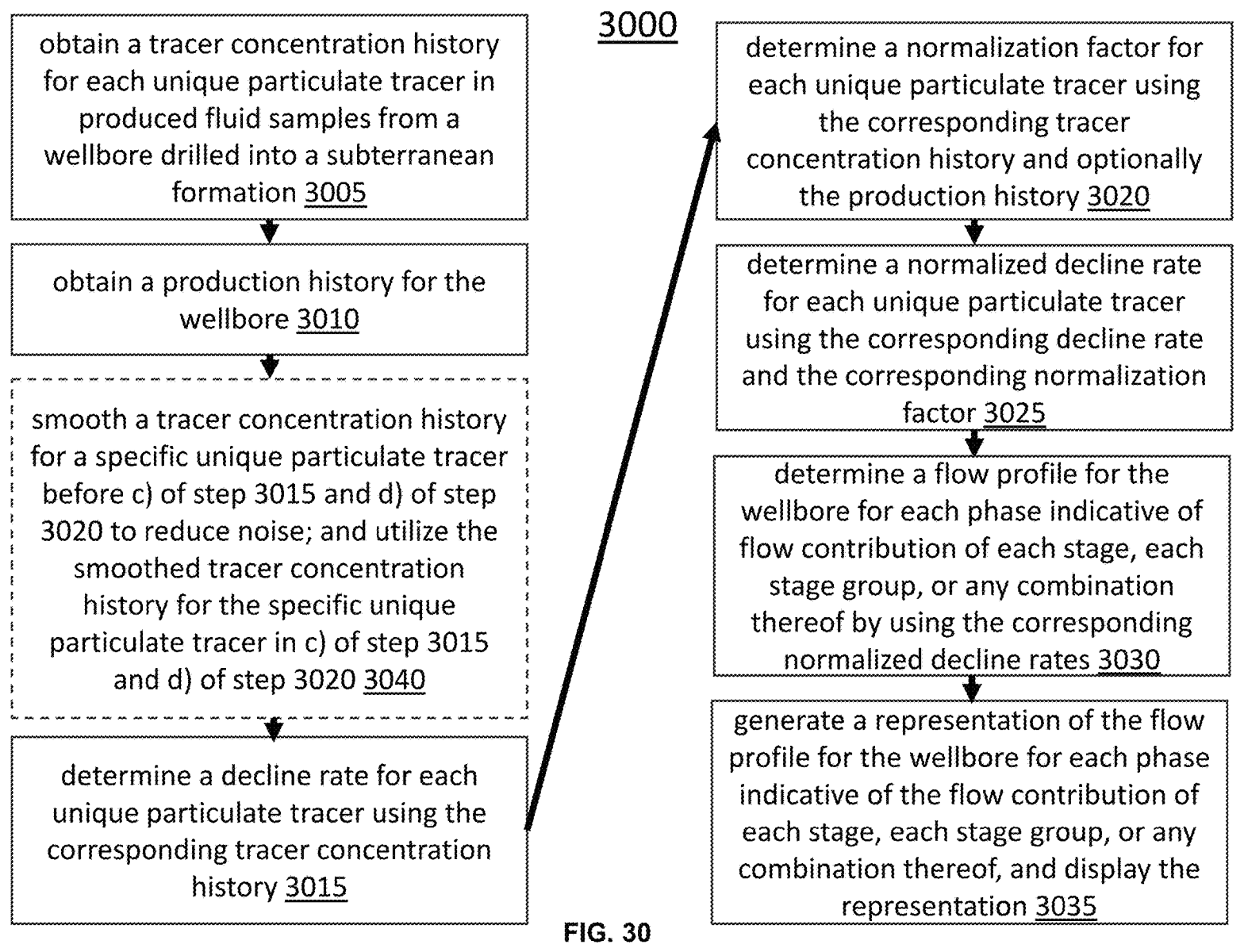

3200 determine a normalization factor for each unique particulate tracer using the corresponding tracer concentration history and optionally the production history 3020 determine a normalized decline rate for each unique particulate tracer using the corresponding decline rate and the corresponding normalization factor 3025 determine a flow profile for the wellbore for each phase indicative of flow contribution of each stage, each stage group, or any combination thereof by using the corresponding normalized decline rates 3030 generate a representation of the flow profile for the wellbore for each phase indicative of the flow contribution of each stage, each stage group, or any combination thereof, and display the representation 3035 obtain a tracer concentration history for each unique particulate tracer in produced fluid samples from a wellbore drilled into a subterranean formation 3005 obtain a production history for the wellbore 3010 smooth a tracer concentration history for a specific unique particulate tracer before c) of step 3015 and d) of step 3020 to reduce noise; and utilize the smoothed tracer concentration history for the specific unique particulate tracer in c) of step 3015 and d) of step 3020 3040 determine a decline rate for each unique particulate tracer using the corresponding tracer concentration history 3015 pump at least one unique particulate tracer throughout each stage, each stage group, or any combination thereof during a hydraulic fracturing operation performed in the subterranean formation 2705 shut-in the wellbore for a period of time to cause tracer clouds to form in the subterranean formation for at least a portion of the unique particulate tracers that were pumped throughout the stages, the stage groups, or any combination thereof 2710 flow back the wellbore to cause produced fluid from the wellbore after the shut-in period 2715 obtain produced fluid samples comprising unique particulate tracers from a wellbore drilled into a subterranean formation 2720 analyze the produced fluid samples obtained from the produced fluid to generate the tracer concentration history for each unique particulate tracer (e.g., lab) 2725 obtain a production history for the wellbore (e.g., field) 2730

SURVEILLANCE USING PARTICULATE TRACERS

CROSS-REFERENCE TO RELATED APPLICATIONS

This application claims priority to U.S. Provisional Patent Application Ser. No. 63/288,447 titled "Surveillance Using Particulate Tracers" and filed on Dec. 10, 2021, the entire contents of which are hereby incorporated by reference. This application is related to two other co-pending applications, filed on even date herewith, and identified by Ser. No. 18/079,045, title: "Surveillance Using Particulate Tracers", and U.S. Pat. No. 12,196,075 and Ser. No. 18/079,052, title: "Surveillance Using Particulate Tracers", and U.S. Publication No. US 2023-0184097, all of which are incorporated by reference.

STATEMENT REGARDING FEDERALLY SPONSORED RESEARCH OR DEVELOPMENT

Not applicable.

TECHNICAL FIELD

The disclosed embodiments relate generally to techniques for surveillance using particulate tracers.

BACKGROUND

Tracers are used in the hydrocarbon industry to track flow patterns and rates of the particular fluid to which it is introduced. Tracers are also used to study properties of the subterranean formation in which the fluid resides. Tracers commonly are chemical compounds that have negligible effects on the fluid. In operation, tracers are injected into the subterranean formation, and thereafter produced and sampled to measure for tracer concentration. There exists a need for surveillance using particulate tracers.

SUMMARY

In accordance with some embodiments, a method of determining a flow profile for a wellbore using unique particulate tracers is disclosed. The method comprises obtaining produced fluid samples comprising unique particulate tracers from a wellbore drilled into a subterranean formation, wherein at least one unique particulate tracer is pumped throughout each stage, each stage group, or any combination thereof during a hydraulic fracturing operation performed in the subterranean formation, and wherein each unique particulate tracer corresponds to an oil phase, a water phase, or a gas phase, and wherein the produced fluid samples comprise at least a portion of the unique particulate tracers that were pumped throughout the stages, the stage groups, or any combination thereof. The method further comprises determining a flow profile for the wellbore for each phase using the produced fluid samples comprising the unique particulate tracers by: a) obtaining a tracer concentration history for each unique particulate tracer; b) obtaining a production history for the wellbore; c) determining a mean residence time for each unique particulate tracer using the corresponding tracer concentration history; d) determining a contact volume proxy for each unique particulate tracer using the production history and the corresponding tracer concentration history; and e) determining the flow profile for the wellbore for each phase indicative of flow contribution of each stage, each stage group, or any combination thereof by using the corresponding mean residence times and the corresponding contact volume proxies.

In accordance with some embodiments, a method of determining a flow profile for a wellbore using unique particulate tracers, the method being implemented in a computer system that includes a physical computer processor and non-transitory storage medium. The method comprises: a) obtaining, from a non-transitory storage medium, a tracer concentration history for each unique particulate tracer in produced fluid samples from a wellbore drilled into a subterranean formation, wherein at least one unique particulate tracer is pumped throughout each stage, each stage group, or any combination thereof during a hydraulic fracturing operation performed in the subterranean formation, and wherein each unique particulate tracer corresponds to an oil phase, a water phase, or a gas phase, and wherein the produced fluid samples comprise at least a portion of the unique particulate tracers that were pumped throughout the stages, the stage groups, or any combination thereof. The method further comprises b) obtaining, from the non-transitory storage medium, a production history for the wellbore; c) determining, with a physical computer processor, a mean residence time for each unique particulate tracer using the corresponding tracer concentration history; d) determining, with the physical computer processor, a contact volume proxy for each unique particulate tracer using the production history and the corresponding tracer concentration history; and e) determining, with the physical computer processor, a flow profile for the wellbore for each phase indicative of flow contribution of each stage, each stage group, or any combination thereof by using the corresponding mean residence times and the corresponding contact volume proxies.

In accordance with some embodiments, a method of determining a flow profile for a wellbore using unique particulate tracers. The method comprises obtaining produced fluid samples comprising unique particulate tracers from a wellbore drilled into a subterranean formation, wherein at least one unique particulate tracer is pumped throughout each stage, each stage group, or any combination thereof during a hydraulic fracturing operation performed in the subterranean formation, and wherein each unique particulate tracer corresponds to an oil phase, a water phase, or a gas phase, and wherein the produced fluid samples comprise at least a portion of the unique particulate tracers that were pumped throughout the stages, the stage groups, or any combination thereof. The method further comprises determining a flow profile for the wellbore for each phase using the produced fluid samples comprising the unique particulate tracers by: a) obtaining a tracer concentration history for each unique particulate tracer; b) optionally obtaining a production history for the wellbore; c) determining a decline rate for each unique particulate tracer using the corresponding tracer concentration history; d) determining a normalization factor for each unique particulate tracer using the corresponding tracer concentration history and optionally the production history; e) determining a normalized decline rate for each unique particulate tracer using the corresponding decline rate and the corresponding normalization factor; and f) determining a flow profile for the wellbore for each phase indicative of flow contribution of each stage, each stage group, or any combination thereof by using the corresponding normalized decline rates.

In accordance with some embodiments, a method of determining a flow profile for a wellbore using unique particulate tracers, the method being implemented in a computer system that includes a physical computer processor and non-transitory storage medium. The method comprises a) obtaining, from the non-transitory storage medium, a tracer concentration history for each unique particulate tracer in produced fluid samples from a wellbore drilled into a subterranean formation, wherein at least one unique particulate tracer is pumped throughout each stage, each stage group, or any combination thereof during a hydraulic fracturing operation performed in the subterranean formation, and wherein each unique particulate tracer corresponds to an oil phase, a water phase, or a gas phase, and wherein the produced fluid samples comprise at least a portion of the unique particulate tracers that were pumped throughout the stages, the stage groups, or any combination thereof. The method further comprises b) optionally obtaining, from the non-transitory storage medium, a production history for the wellbore; c) determining, with the physical computer processor, a decline rate for each unique particulate tracer using the corresponding tracer concentration history; d) determining, with the physical computer processor, a normalization factor for each unique particulate tracer using the corresponding tracer concentration history and optionally the production history; e) determining, with the physical computer processor, a normalized decline rate for each unique particulate tracer using the corresponding decline rate and the corresponding normalization factor; and f) determining, with the physical computer processor, a flow profile for the wellbore for each phase indicative of flow contribution of each stage, each stage group, or any combination thereof by using the corresponding normalized decline rates.

BRIEF DESCRIPTION OF THE DRAWINGS

FIGS. 1E-1, 1E-2, 1E-3 illustrates examples of unique particulate tracers pumped throughout stages in the context of multiple wellbores.

FIG. 3A-3C illustrate embodiments of pumping unique particulate tracers in the near wellbore region in the context of a multiple wellbores.

FIG. 7A-7G include various examples consistent with the disclosure.

FIG. 9 illustrates an example method of determining a flow profile for a wellbore using unique particulate tracers FIG. 10 illustrates more information including the Δt, which is arrival time difference.

FIG. 11-22 illustrate various ways to refine the wellbore volume and various other optional steps.

FIG. 25 illustrates an example method for determining a flow profile for a wellbore using unique particulate tracers.

FIG. 27 illustrates an example method for determining a flow profile for a wellbore using unique particulate tracers.

FIG. 30 illustrates an example method for determining a flow profile for a wellbore using unique particulate tracers.

FIG. 32 illustrates an example method for determining a flow profile for a wellbore using unique particulate tracers.

Various embodiments and examples are provided in the various figures. Like reference numerals refer to corresponding parts throughout the drawings.

DETAILED DESCRIPTION OF EMBODIMENTS

Figures 1A, 1B, 1C:
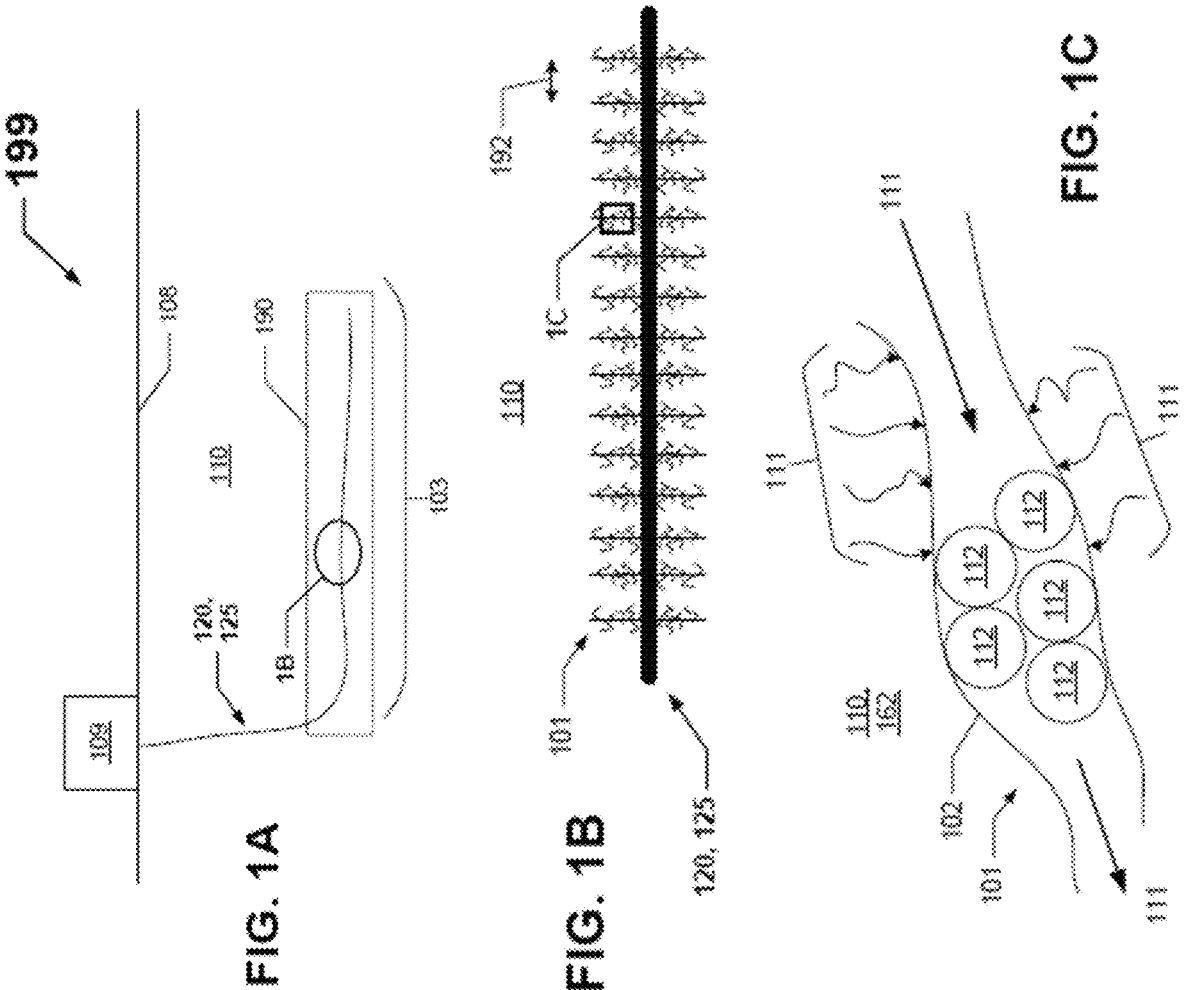
FIGS. 1A, 1B, and 1C show a field system, and details thereof, with which example embodiments can be used.
Figures 1, 1D:
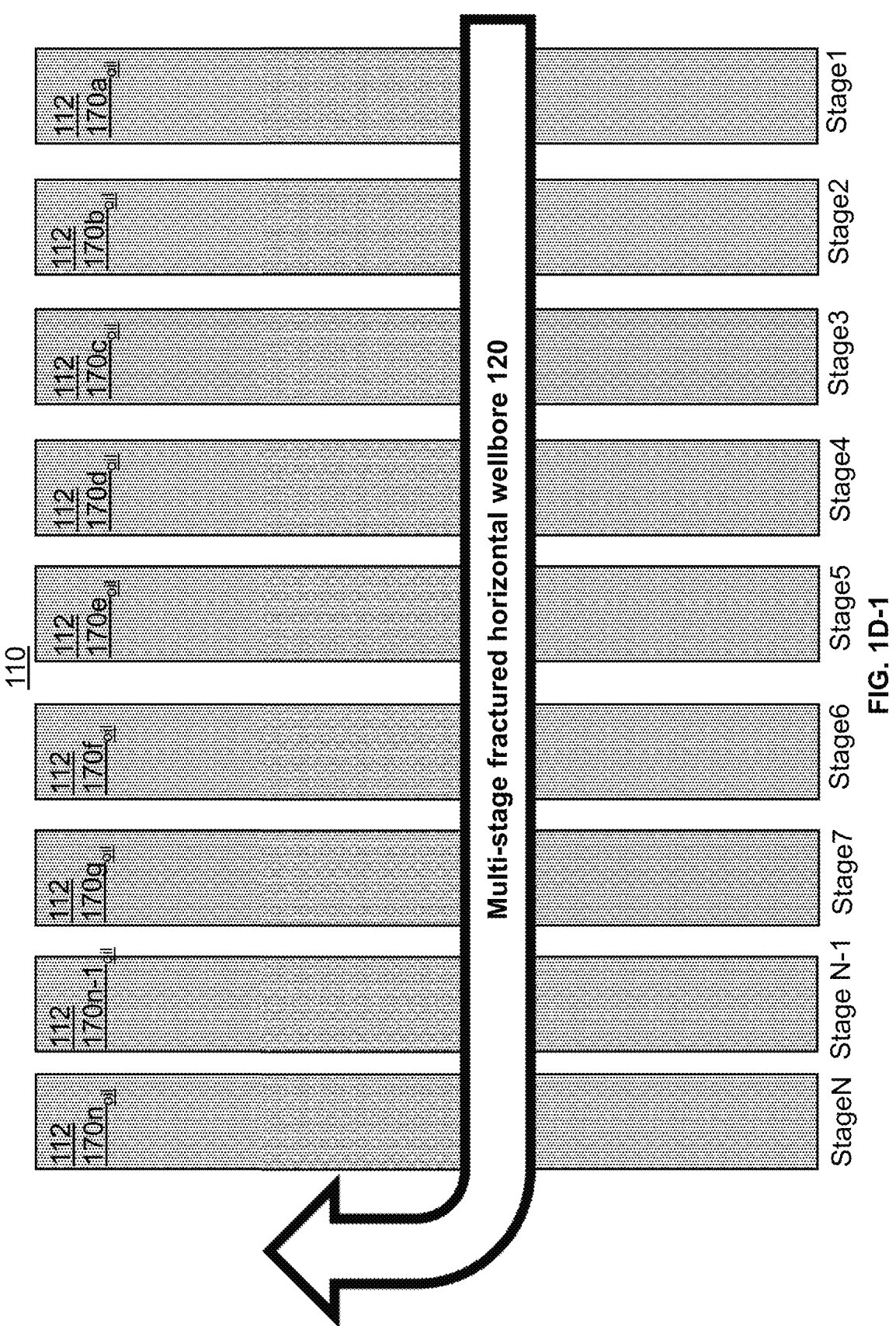
FIGS. 1D-1, 1D-2, 1D-3 illustrates examples of unique particulate tracers pumped throughout stages in the context of a single wellbore.
Figures 1, 1D, 2:
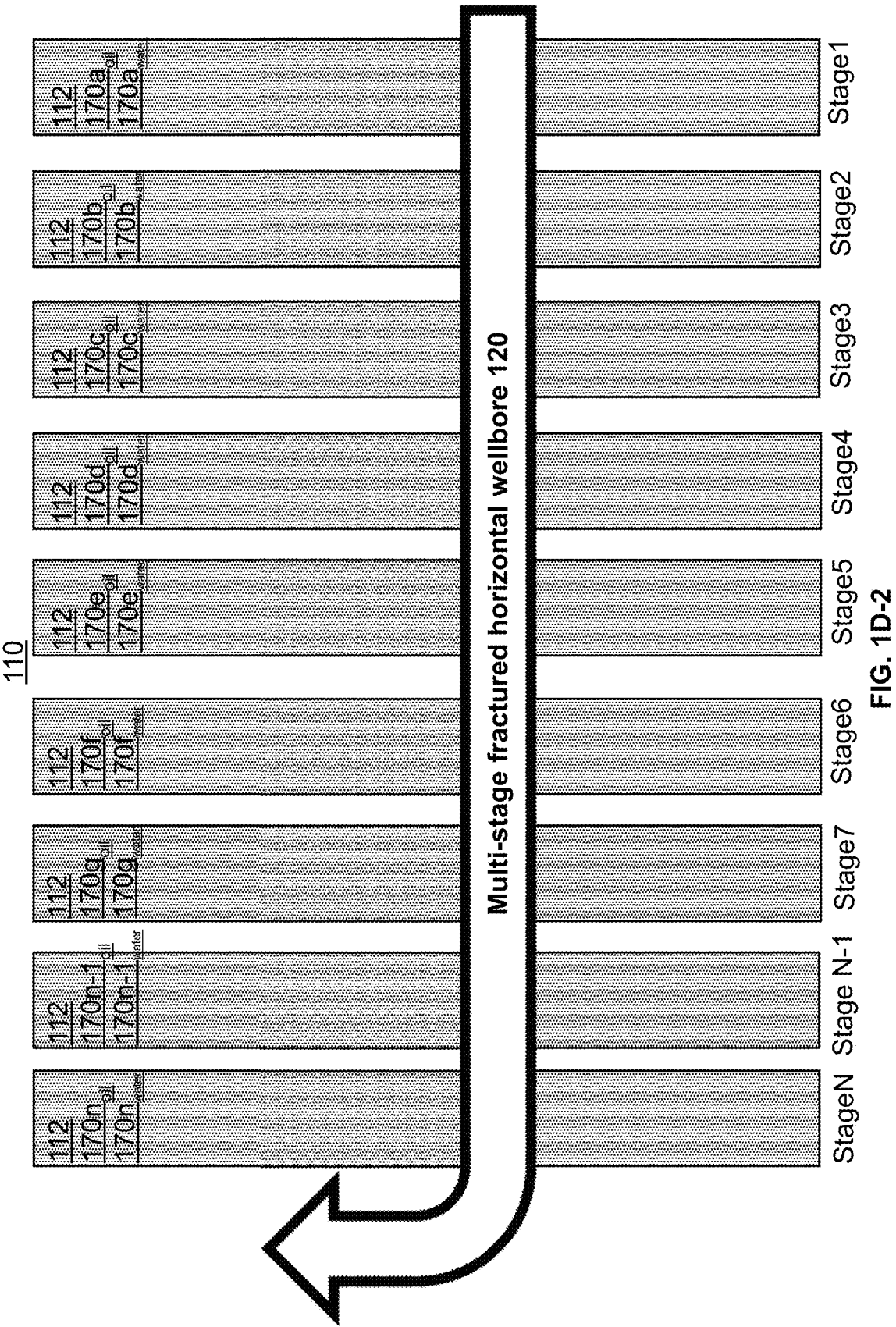
Figures 1, 1D, 2, 3:
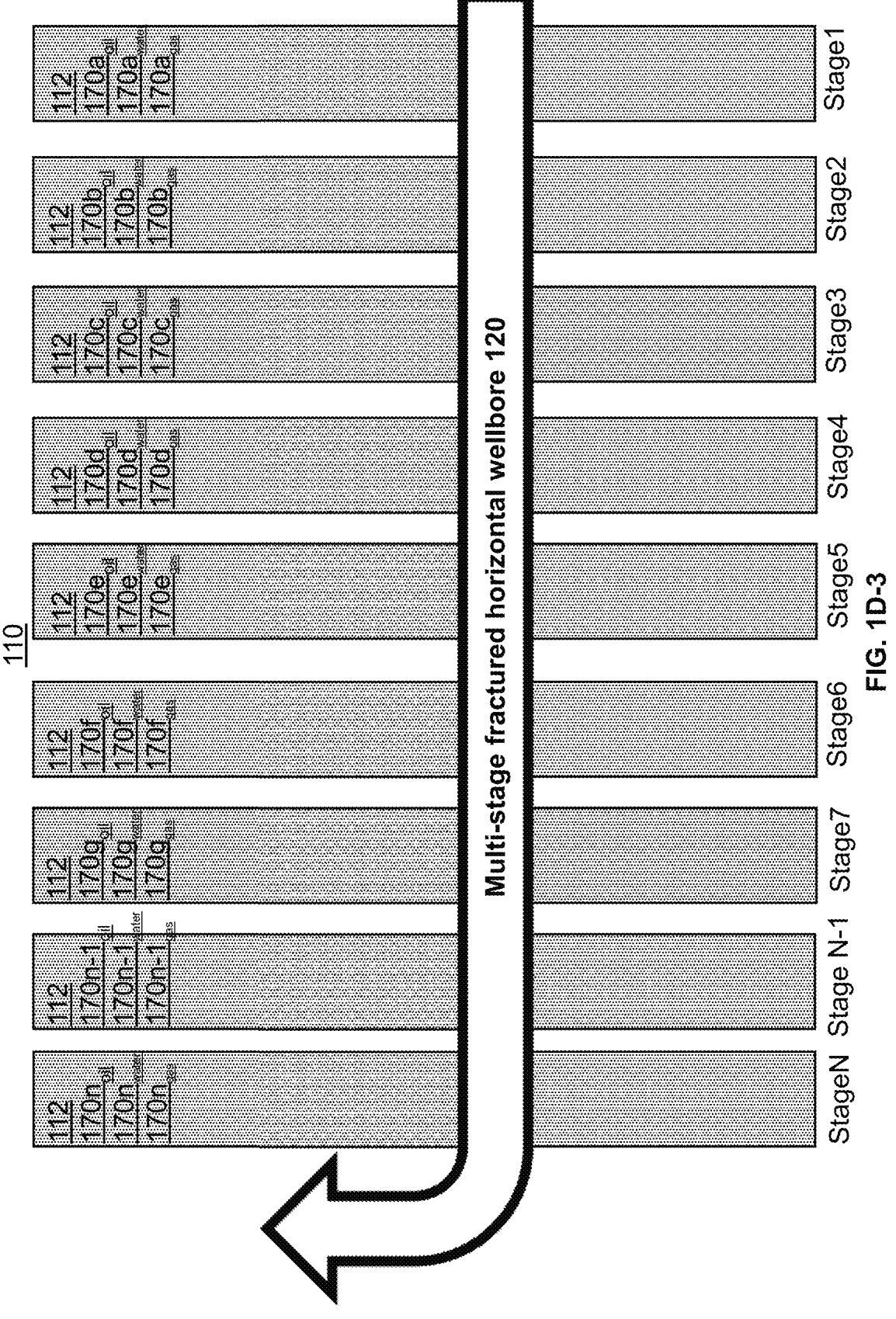
Figures 1, 1E:
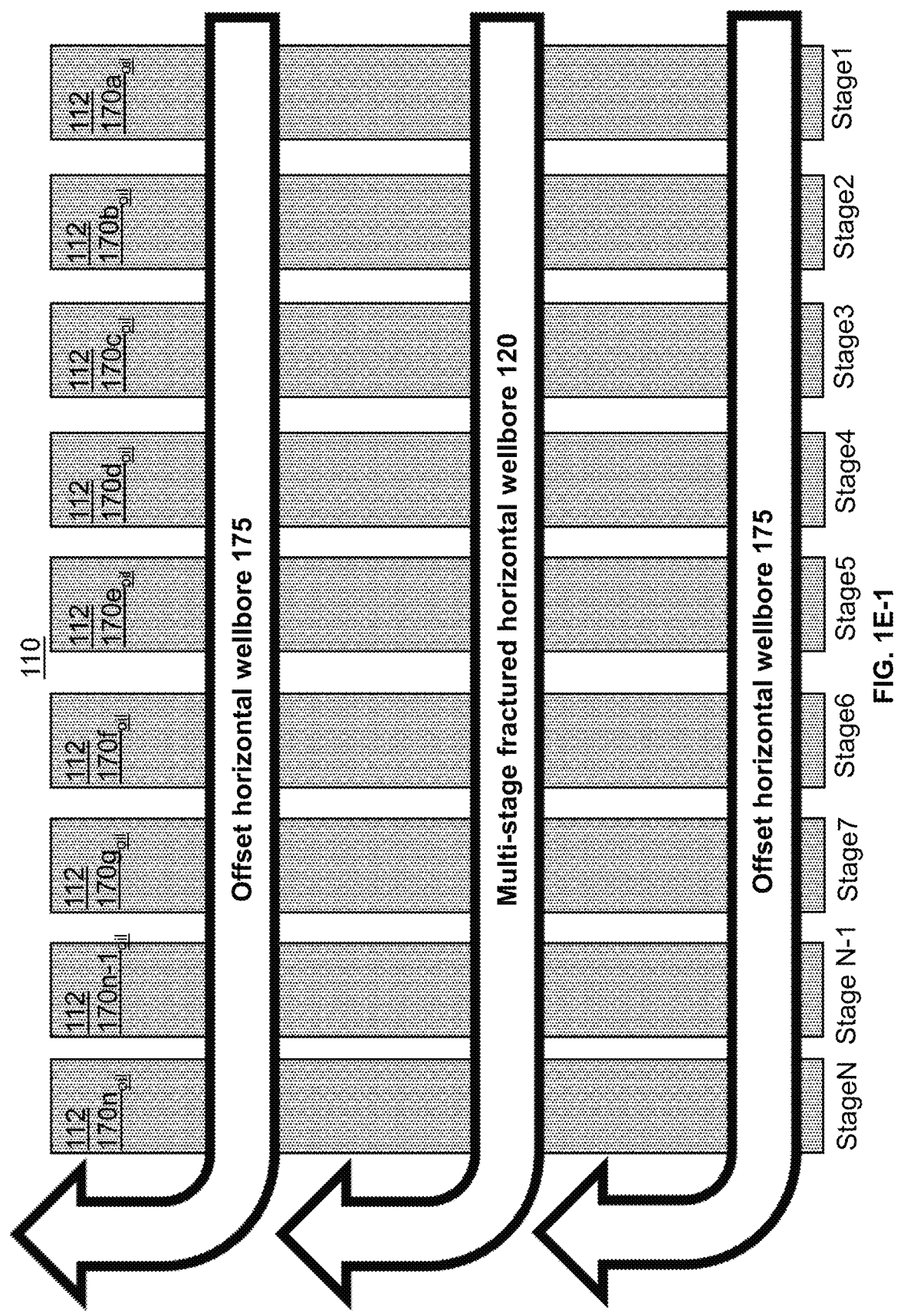
Figures 1, 1E, 2:
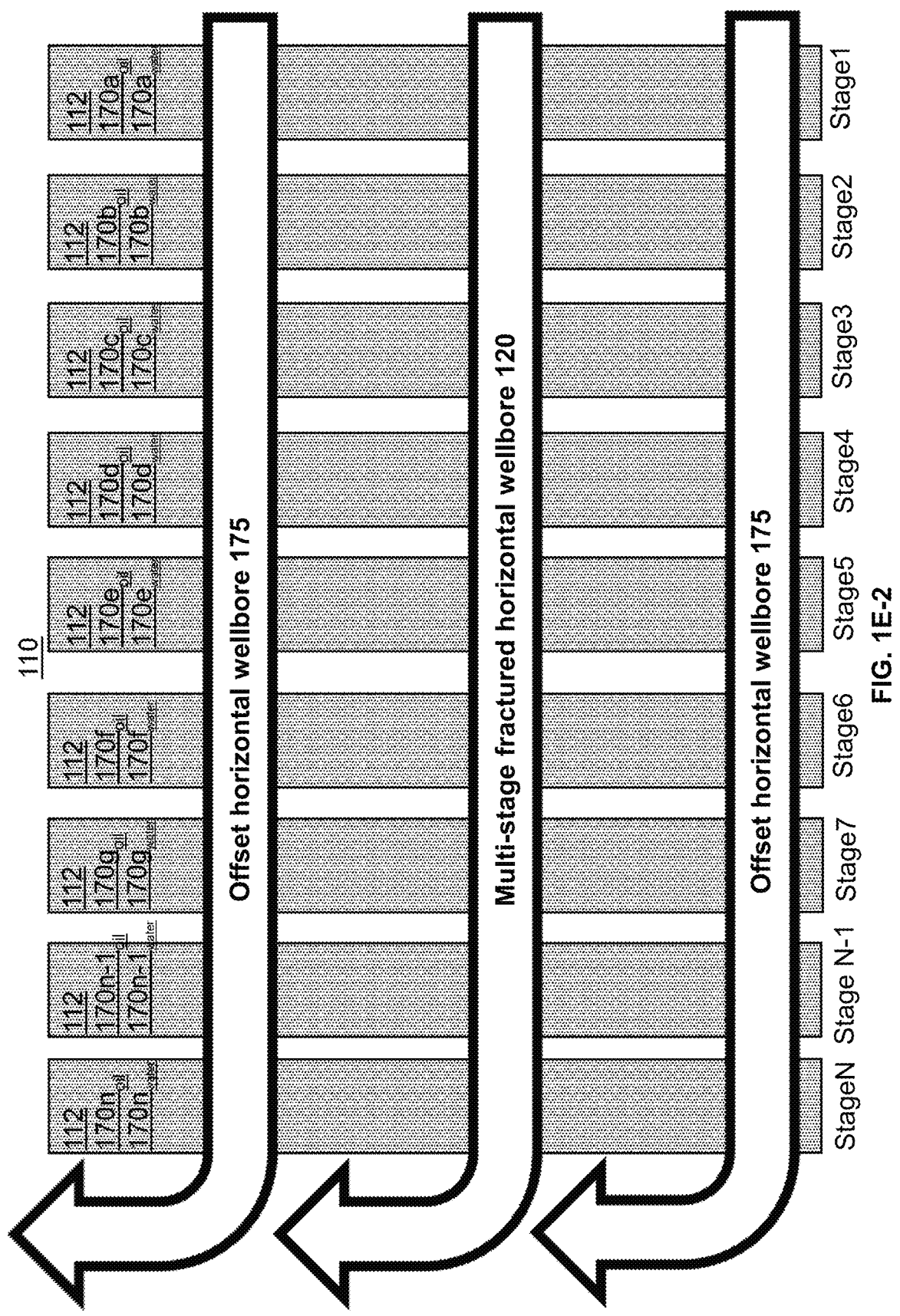
Figures 1, 1E, 2, 3:
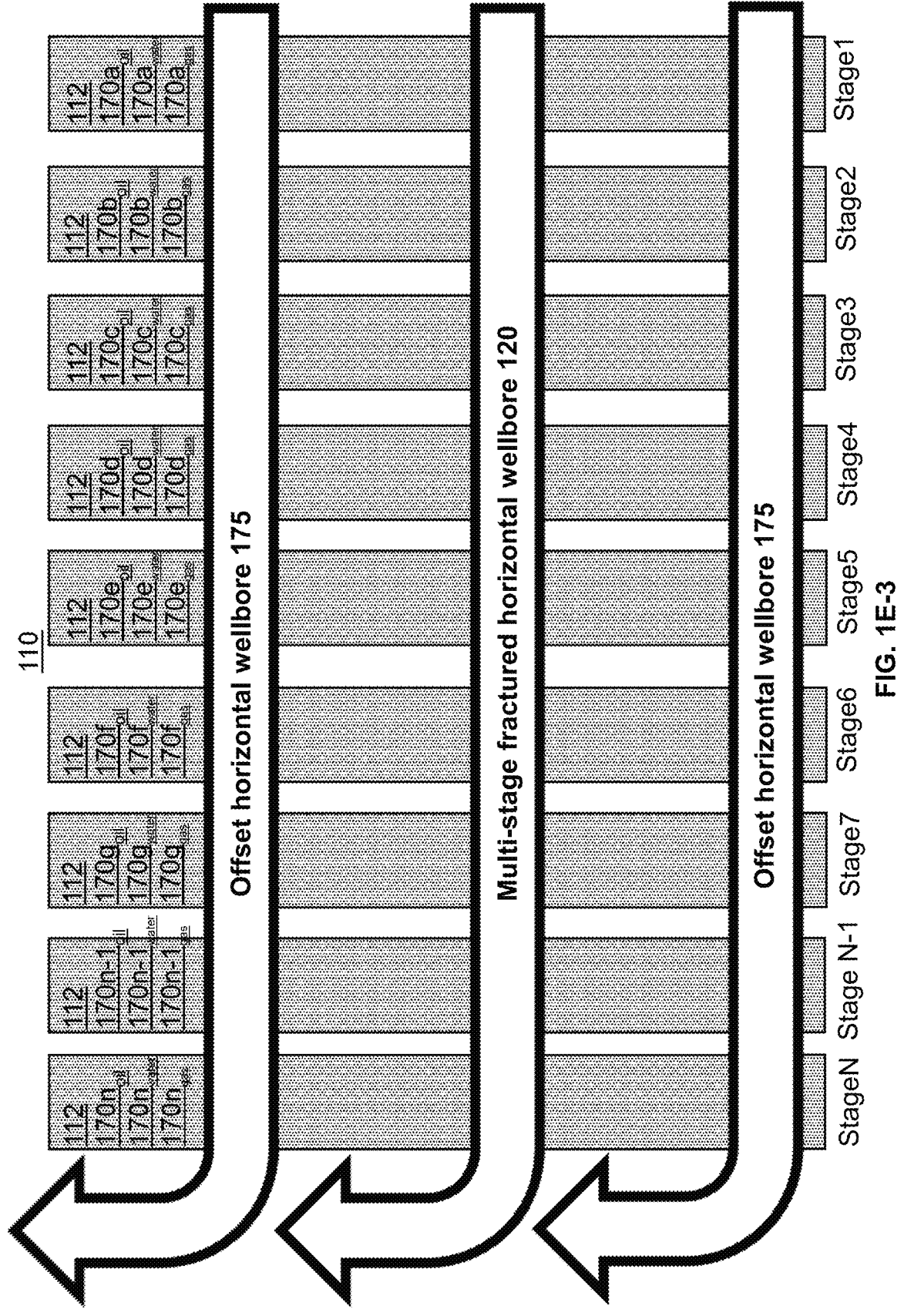

PARTICULATE TRACERS: The term "particulate tracers" is utilized herein to refer to solid particles with chemical tracers bound to them. The particulate tracers may be practically any particulate tracers known in the art, such as particulate tracers for hydrocarbons (e.g., oil), particulate tracers for water, particulate tracers for gas, or any combination thereof. For example, types of particulate tracers that are introduced into the subterranean formation may include, but are not limited to, fluorinated benzoic acids (FBAs), fluorescein dyes, FBA/fluorescein synthesis, fluorescing nanocrystals, radioactive tracers, fluorescing nanoparticles, magnetic nanoparticle tracers, etc.

Particulate tracers may differ in density, for example, from specific gravity of 0.90 to 2.75 (e.g., 0.96 to 2.65 in one embodiment, 0.96 to 1.5 in a second embodiment, etc.). The density may affect rheology and flow. The average size of particulate tracer particles may be 40 mesh to 100 mesh. Particulate tracers generally release at the same rate independent of the flowrate. The particulate tracers may be substantially the same size as proppant particles, and as such, the particulate tracers may be pumped with proppant particles and stay with the proppant particles (sometimes simply referred to as "proppant"). Those of ordinary skill in the art will appreciate that the term "particulate tracer" is not meant to be limited, and the term "particulate tracer" may include practically any substance that can function as a particulate tracer as discussed herein.

For simplicity, the term "unique particulate tracer" is utilized herein to distinguish between different particulate tracers. A unique particulate tracer includes at least one solid particle comprising tracer material. To further distinguish different unique particulate tracers, sometimes the term first, second, each, etc. may be utilized herein (e.g., first unique oil particulate tracer, second unique oil particulate tracer, each unique oil particulate tracer, etc.). Furthermore, a specific particulate tracer, such as a first unique oil particulate tracer, may be pumped into a single stage or a stage group that comprises at least two stages due to a shortage of different particulate tracers, costs, logistics, or other reasons. For simplicity, those of ordinary skill in the art will appreciate that discussion of a "stage" may also include a "stage group" herein unless stated otherwise.

In the existing practice, a unique oil particulate tracer may be pumped throughout each stage and/or stage group if there is an interest in oil. A unique water particulate tracer may be pumped throughout each stage and/or stage group if there is an interest in water. A unique gas particulate tracer may be pumped throughout each stage and/or stage group if there is an interest in gas. FIGS. 1D-1, 1D-2, 1D-3, 1E-1, 1E-2, and 1E-3 illustrate different pumping options in which unique particulate tracers are pumped throughout stages and/or stage groups.

Figure 1F:
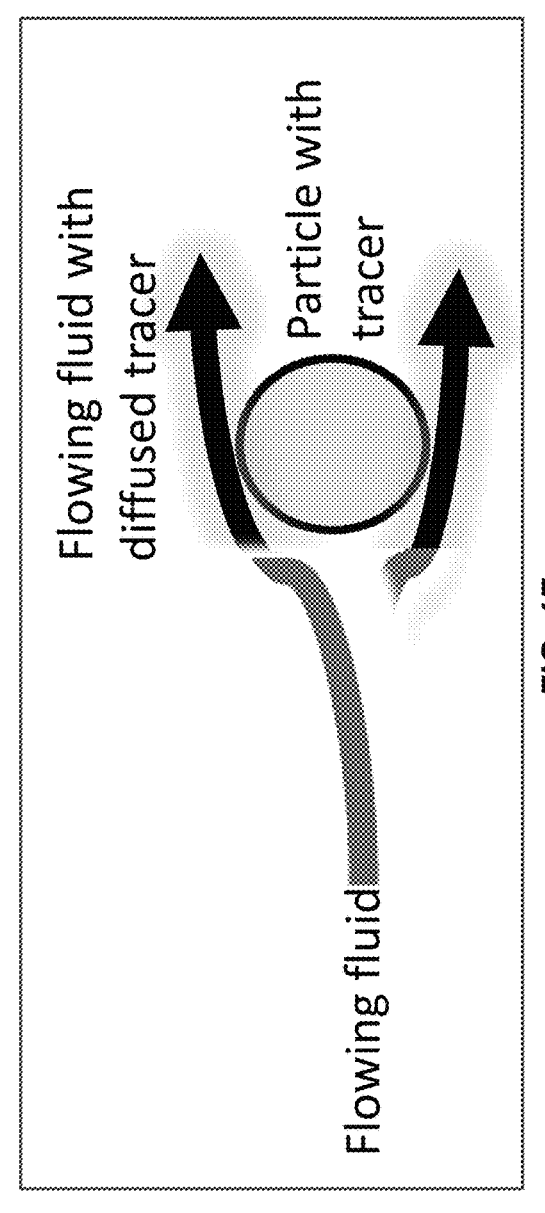
FIG. 1F illustrates that the unique particulate tracers may react and diffuse into flowing fluid and the fluid may be produced from a wellbore as produced fluid.

As illustrated in FIG. 1F, the unique particulate tracers may react and diffuse into flowing fluid and the fluid may be produced from a wellbore as produced fluid. For example, unique oil particulate tracers may react and diffuse into the fluid in response to contact with oil in the fluid. Similarly, unique water particulate tracers may react and diffuse into the fluid in response to contact with water in the fluid. Similarly, unique gas particulate tracers may react and diffuse into the fluid in response to contact with gas in the fluid. Similarly, in a single stage of a hydraulic fracturing operation, different particulate tracers may react and diffuse into the fluid in response to contact with the corresponding item in the fluid. For example, in a single stage of a hydraulic fracturing operation, a unique oil particulate tracer may diffuse into the fluid in response to contact with oil in the fluid and a unique gas particulate tracer may diffuse into the fluid in response to contact with gas in the fluid. The produced fluid may be sampled to analyze the unique particulate tracers in the samples. Each unique particulate tracer pumped into a stage and/or stage group may depend on the desired information that is sought about that stage and/or stage group as discussed further hereinbelow.

Placing Unique Particulate Tracers in a Subterranean Formation Having a Wellbore Therewithin Such that a Substantial Portion of the Unique Particulate Tracers are Placed in a Near Wellbore Region of the Subsurface Formation Proximate to the Wellbore:

Described below are methods and systems of placing unique particulate tracers in a subterranean formation having a wellbore therewithin. These embodiments are designed to be of particular use for surveillance within a subsurface formation, including generating flow rates (e.g., barrels per day). The embodiments described herein place particulate tracers in at least two stages, including a first stage and a second stage, during a hydraulic fracturing operation in the subsurface formation. The particulate tracers are pumped only in a fraction of each stage and/or each stage group such that a substantial portion of the unique particulate tracers are placed in a near wellbore region of the subsurface formation proximate to the wellbore. As will be described further, the embodiments provided herein improve upon existing approaches to placing unique particulate tracers in a subterranean formation.

Reference will now be made in detail to various embodiments, examples of which are illustrated in the accompanying drawings. In the following detailed description, numerous specific details are set forth in order to provide a thorough understanding of the present disclosure and the embodiments described herein. However, embodiments described herein may be practiced without these specific details. In other instances, well-known methods, procedures, components, and mechanical apparatus have not been described in detail so as not to unnecessarily obscure aspects of the embodiments.

Example embodiments of placing unique particular tracers in a subsurface formation having a wellbore therewithin will be described more fully hereinafter with reference to the accompanying drawings. Placing unique particular tracers in a subterranean formation having a wellbore therewithin may, however, be embodied in many different forms and should not be construed as limited to the example embodiments set forth herein. Rather, these embodiments and examples are provided so that this disclosure will be thorough and complete, and will fully convey the scope of placing unique particular tracers in a subterranean formation having a wellbore therewithin to those of ordinary skill in the art. Like, but not necessarily the same, elements (also sometimes called components) in the various figures are denoted by like reference numerals for consistency.

FIGS. 1A through 1C show a field system 199, including details thereof, with which example embodiments can be used. Specifically, FIG. 1A shows a schematic diagram of a land-based field system 199 in which a wellbore 120 has been drilled in a subterranean formation 110. FIG. 1B shows a detail of a substantially horizontal section 103 of the wellbore 120 of FIG. 1A. FIG. 1C shows a detail of an induced fracture 101 of FIG. 1B. The field system 199 in this example includes a wellbore 120 disposed in a subterranean formation 110 using field equipment 109 (e.g., a derrick, a tool pusher, a clamp, a tong, drill pipe, casing pipe, a drill bit, a wireline tool, a fluid pumping system) located above a surface 108 and within the wellbore 120. Once the wellbore 120 is drilled, a casing string 125 is inserted into the wellbore 120 to stabilize the wellbore 120 and allow for the extraction of subterranean resources (e.g., hydrocarbon such as natural gas, oil) from the subterranean formation 110.

The surface 108 can be ground level for an onshore application and the sea floor/lakebed for an offshore application. For offshore applications, at least some of the field equipment can be located on a platform that sits above the water level. The point where the wellbore 120 begins at the surface 108 can be called the wellhead. While not shown in FIGS. 1A and 1B, there can be multiple wellbores 120, each with its own wellhead but that is located close to the other wellheads, drilled into the subterranean formation 110 and having substantially horizontal sections 103 that are close to each other. In such a case, the multiple wellbores 120 can be drilled at the same pad or at different pads. When the drilling process is complete, other operations, such as fracturing operations, can be performed. The fractures 101 are shown to be located in the horizontal section 103 of the wellbore 120 in FIG. 1B. The fractures 101, whether induced and/or naturally occurring, can additionally or alternatively be located in other sections (e.g., a substantially vertical section, a transition area between a vertical section and a horizontal section) of the wellbore 120. Example embodiments can be used along any portion of the wellbore 120 where fractures 101 are located.

The subterranean formation 110 can include one or more of a number of formation types, including but not limited to shale, limestone, sandstone, clay, sand, and salt. In certain embodiments, a subterranean formation 110 can include one or more reservoirs in which one or more resources (e.g., oil, natural gas, water, steam) can be located. One or more of a number of field operations (e.g., fracturing, coring, tripping, drilling, setting casing, extracting downhole resources) can be performed to reach an objective of a user with respect to the subterranean formation 110.

The wellbore 120 can have one or more of a number of segments or hole sections, where each segment or hole section can have one or more of a number of dimensions. Examples of such dimensions can include, but are not limited to, a size (e.g., diameter) of the wellbore 120, a curvature of the wellbore 120, a total vertical depth of the wellbore 120, a measured depth of the wellbore 120, and a horizontal displacement of the wellbore 120. There can be multiple overlapping casing strings of various sizes (e.g., length, outer diameter) contained within and between these segments or hole sections to ensure the integrity of the wellbore construction. In this case, one or more of the segments of the subterranean wellbore 120 is the substantially horizontal section 103. As stated above, in additional or alternative cases, one or more of the segments of the subterranean wellbore 120 is a substantially vertical section.

As discussed above, inserted into and disposed within the wellbore 120 of FIGS. 1A and 1B are a number of casing pipes that are coupled to each other end-to-end to form the casing string 125. In this case, each end of a casing pipe has mating threads (a type of coupling feature) disposed thereon, allowing a casing pipe to be directly or indirectly mechanically coupled to another casing pipe in an end-to-end configuration. The casing pipes of the casing string 125 can be indirectly mechanically coupled to each other using a coupling device, such as a coupling sleeve.

Each casing pipe of the casing string 125 can have a length and a width (e.g., outer diameter). The length of a casing pipe can vary. For example, a common length of a casing pipe is approximately 40 feet. The length of a casing pipe can be longer (e.g., 60 feet) or shorter (e.g., 10 feet) than 40 feet. The width of a casing pipe can also vary and can depend on the cross-sectional shape of the casing pipe. For example, when the shape of the casing pipe is cylindrical, the width can refer to an outer diameter, an inner diameter, or some other form of measurement of the casing pipe. Examples of a width in terms of an outer diameter can include, but are not limited to, 4½ inches, 7 inches, 7⅝ inches, 8⅝ inches, 10¾ inches, 13⅜ inches, and 14 inches.

The size (e.g., width, length) of the casing string 125 can be based on the information (e.g., diameter of the borehole drilled) gathered using field equipment with respect to the subterranean wellbore 120. The walls of the casing string 125 have an inner surface that forms a cavity 165 that traverses the length of the casing string 125. Each casing pipe can be made of one or more of a number of suitable materials, including but not limited to steel. Cement 109 is poured into the wellbore 120 through the cavity 165 and then forced upward between the outer surface of the casing string 125 and the wall of the subterranean wellbore 120. In some cases, a liner may additionally be used with, or alternatively be used in place of, some or all of the casing pipes.

Once the cement dries to form concrete, a number of fractures 101 are induced in the subterranean formation 110. The fractures 101 can be induced by hydraulic fracturing. The hydraulic fracturing process involves the injection of large quantities of fluids containing water, chemical additives, and proppant 112 into the subterranean formation 110 from the wellbore 120 to create fracture networks. A subterranean formation 110 naturally has fractures 101, but these naturally occurring fractures 101 have inconsistent characteristics (e.g., length, spacing) and so in some cases cannot be relied upon for extracting subterranean resources without having additional fractures 101, such as what is shown in FIG. 1B, induced in the subterranean formation 110.

Operations that induce fractures 101 in the subterranean formation 110 use any of a number of fluids that include proppant 112 (e.g., sand particles, ceramic pellets). When proppant 112 is used, some of the fractures 101 (also sometimes called principal or primary fractures) receive proppant 112, while a remainder of the fractures 101 (also sometimes called secondary fractures) do not have any proppant 112 in them.

As shown in FIG. 1C, the proppant 112 is designed to become lodged inside at least some of the induced fractures 101 to keep those fractures 101 open after the fracturing operation is complete. The size of the proppant 112 is an important design consideration. Sizes (e.g., 40/70 mesh, 50/140 mesh) of the proppant 112 can vary. While the shape of the proppant 112 is shown as being uniformly spherical, and the size is substantially identical among the proppant 112, the actual sizes and shapes of the proppant 112 can vary. If the proppant 112 is too small, the proppant 112 will not be effective at keeping the fractures 101 open enough to effectively allow subterranean resources 111 to flow through the fractures 101 from the rock matrices 162 in the subterranean formation 110 to the wellbore 120. If the proppant 112 is too large, the proppant 112 can plug up the fractures 101, blocking the flow of the subterranean resources 111 through the fractures 101.

The use of proppant 112 in certain types of subterranean formation 110, such as shale, is important. Shale formations typically have permeabilities on the order of microdarcys (mD) to nanodarcys (nD). When fractures 101 are induced in such formations with low permeabilities, it is important to sustain the fractures 101 and their conductivity for an extended period of time in order to extract more of the subterranean resource 111.

The wellbore 120 is hydraulically fractured in terms of stages, which are illustrated as Stage1 to StageN in FIGS. 1D-1, 1D-2, 1D-3, 1E-1, 1E-2, and 1E-3. Each stage includes single or multiple perforations clusters and the fractures 101 are induced from the perforation clusters. Additionally, unique particulate tracers are pumped with the proppant 112 for surveillance purposes to track flow patterns and rates of the fluid to which it is introduced.

In existing practice, a unique particulate tracer is typically pumped throughout each stage to determine over time which stage is contributing to water or hydrocarbon (e.g., oil) flow. The unique particulate tracers are chemical compounds that have negligible effects on the fluid carrying the particulate tracers. In the existing practice, the unique particulate tracers are pumped throughout the stages and/or throughout the stage groups with the proppant such as illustrated in FIGS. 1D-1, 1D-2, 1D-3, 1E-1, 1E-2, and 1E-3, and thereafter, at least a portion the unique particulate tracers are produced in the produced fluid and sampled to measure for tracer concentration. A field operator manually collects at least one sample from the produced fluid, transports the at least one sample to a laboratory, filters the at least one sample, and finally analyzes the at least one sample for tracer concentration. The existing practice of pumping unique particulate tracers 170 (illustrated as $170a_{oil}$, $170b_{oil}$, and so on) with the proppant 112 in the entirety of each Stage1 through StageN for a single wellbore 120 is illustrated in as illustrated FIGS. 1D-1, 1D-2, 1D-3, 1E-1, 1E-2, and 1E-3. The existing practice of pumping unique particulate tracers 170 with the proppant 112 in the entirety of each Stage1 through StageN for a plurality of wellbores, such as the wellbore 120 and two offset horizontal wellbores 175, is illustrated in FIGS. 1E-1, 1E-2, and 1E-3. Due to the limited quantity of unique particulate tracers, costs, logistics, etc., a unique particulate tracer may be pumped with the proppant in the entirety of each stage and/or stage group (i.e., a plurality of stages) in the existing practice.

Figure 1H:
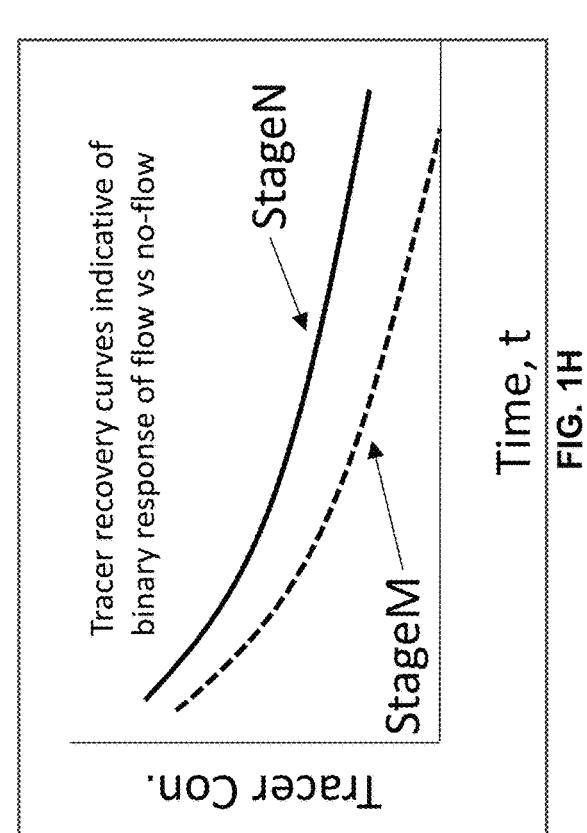
FIG. 1G-1H illustrate diagram related to binary response.
Figure 1G:
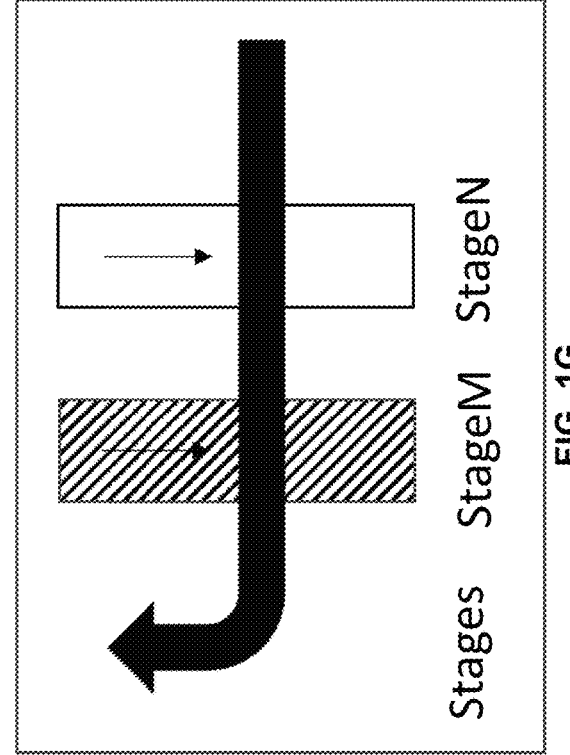

The existing practice, as illustrated in FIG. 1D-1, 1D-2, 1D-3, 1E-1, 1E-2, 1E-3, requires a large quantity of unique particulate tracers as well as the associated financial cost, time, equipment, and personnel to handle the large quantity of the unique particulate tracers. Furthermore, quantitative evaluation of stage and/or stage group contribution to flow is not generally possible with the existing manner that the unique particulate tracers are placed throughout the entirety of stages and/or stage groups. First, in FIGS. 1E-1, 1E-2, and 1E-3, quantitative evaluation of stage or stage group contribution to flow is not generally possible because the particulate tracers of wellbore 120 may go to one or both offset wellbores 175. As a result, the particulate tracers affecting the flow in the wellbore 120 may not be known and there may not be a good baseline for flow profiling. As another example, tracer recovery curves may simply indicate a binary response of flow vs no-flow. FIG. 1G illustrates a single wellbore with a StageM and a StageN and FIG. 1H illustrates typical tracer recovery curves indicative of just the binary response of flow vs. no-flow. Second, tracer release rate is not a function of the flowrate, so the quantification is generally not possible with the existing tracer design. Indeed, existing placement of unique particulate tracers have not been able to quantify the flow profile along the lateral during flow so far because tracer release rate for unique particulate tracers is not proportional to the flow rate. For example, the existing practice of placing unique particulate tracers throughout the entirety of stages and/or stage groups make it difficult to quantify the flow profile along the lateral during flow because tracer release rate for particulates is not proportional to the flow rate. Third, if the unique particulate tracers are distributed throughout the injected stage volume, then the produced unique particulate tracer response may be very dispersed so the existing methods (similar to solid wellbore tracer application) for flow profiling called the pulse velocity method or decay method cannot be used. In short, there are current limitations on flow profiling using unique particulate tracers that are placed in the entirety of stages and/or stage groups.

Figure 2A:
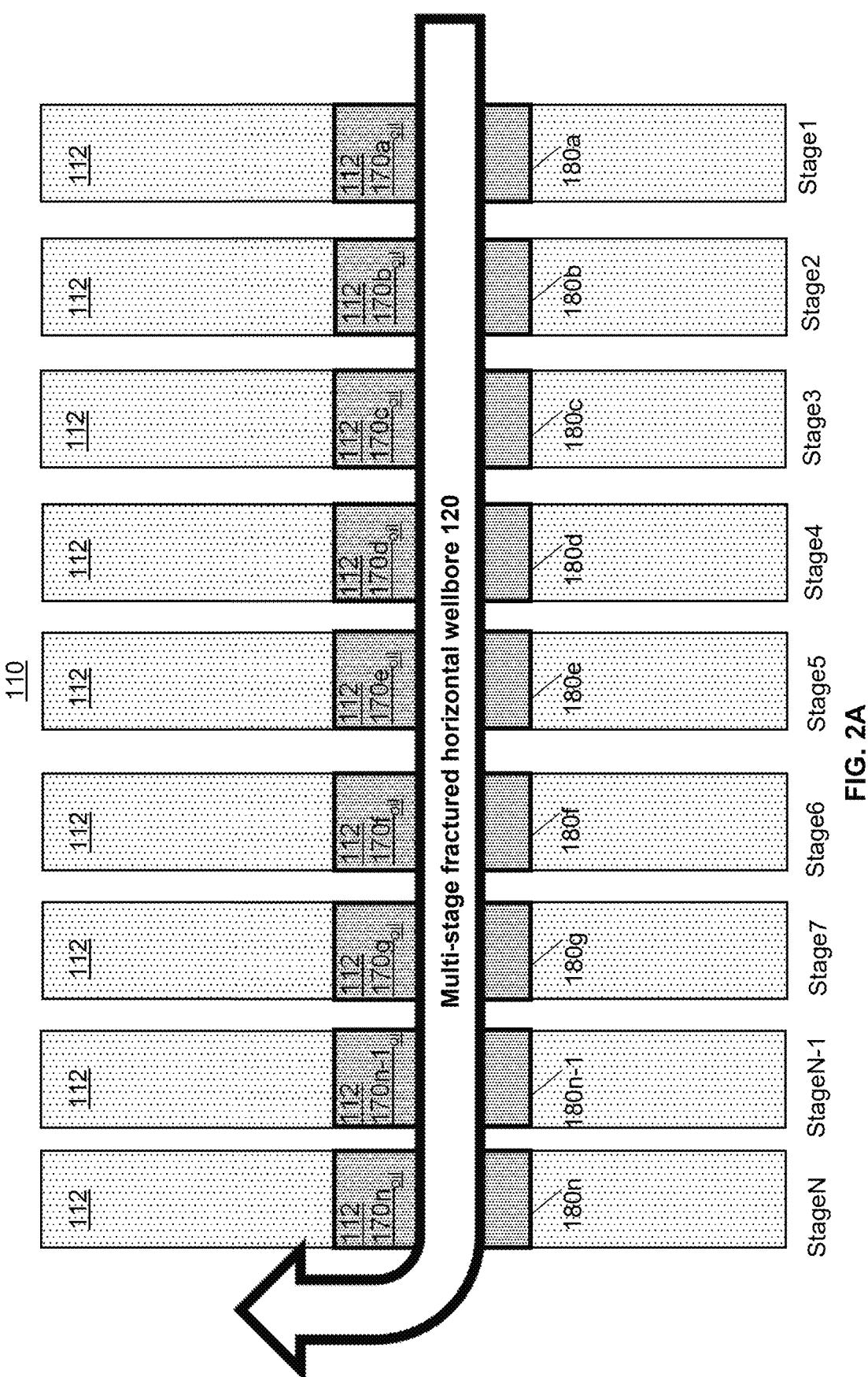
FIG. 2A-2D illustrate embodiments of pumping unique particulate tracers in the near wellbore region in the context of a single wellbore.
Figure 2B:
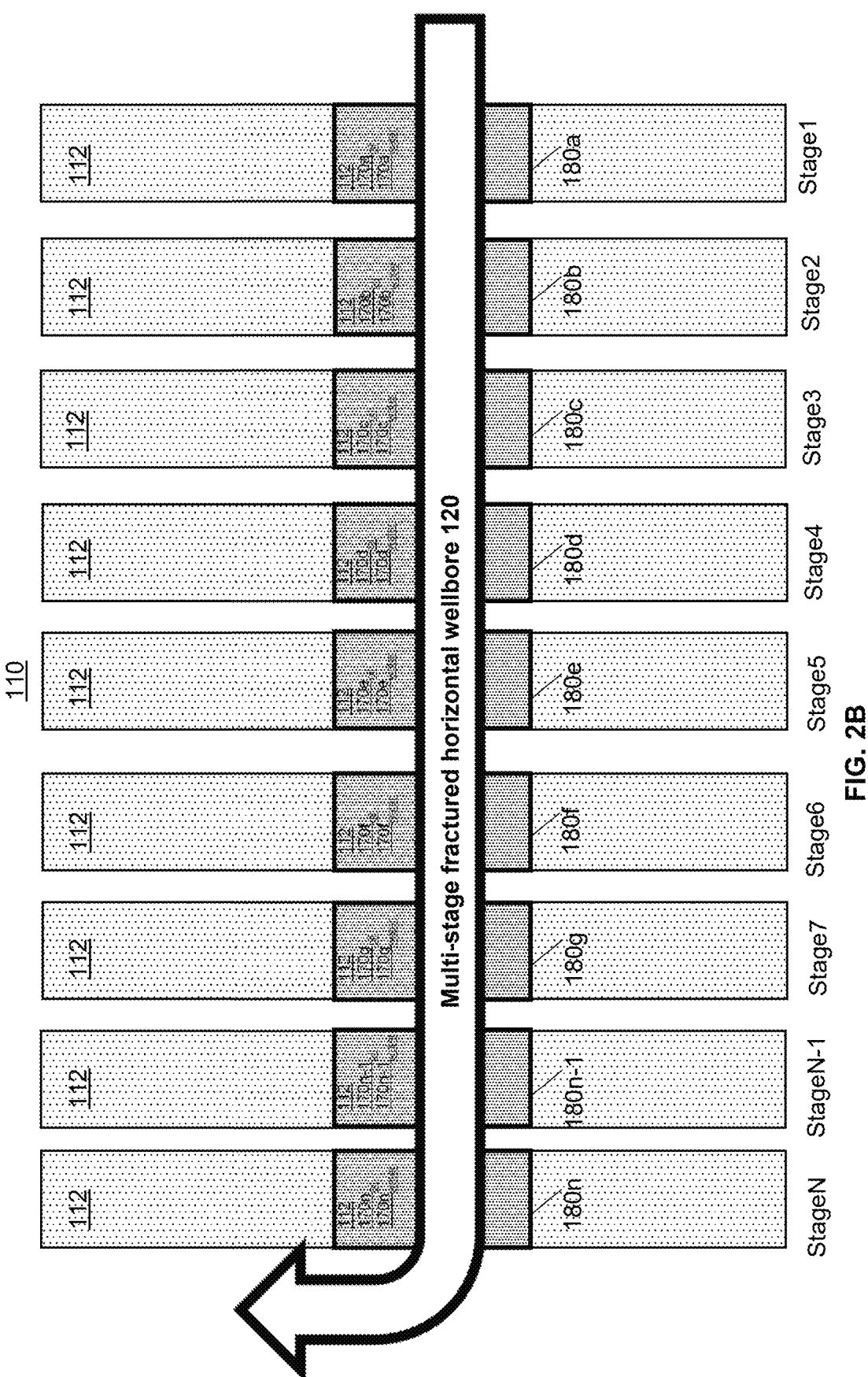
Figure 2C:
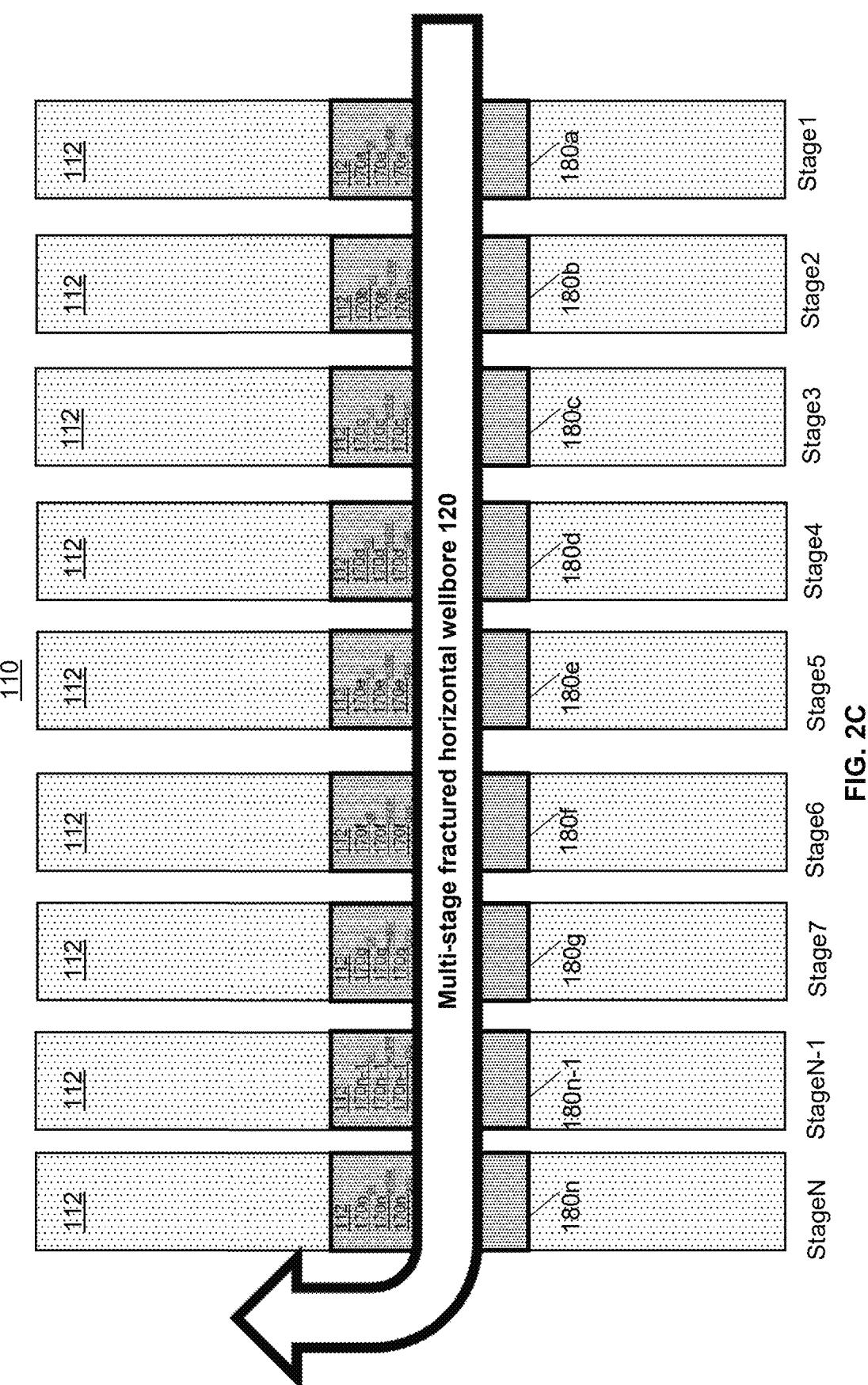
Figure 2D:
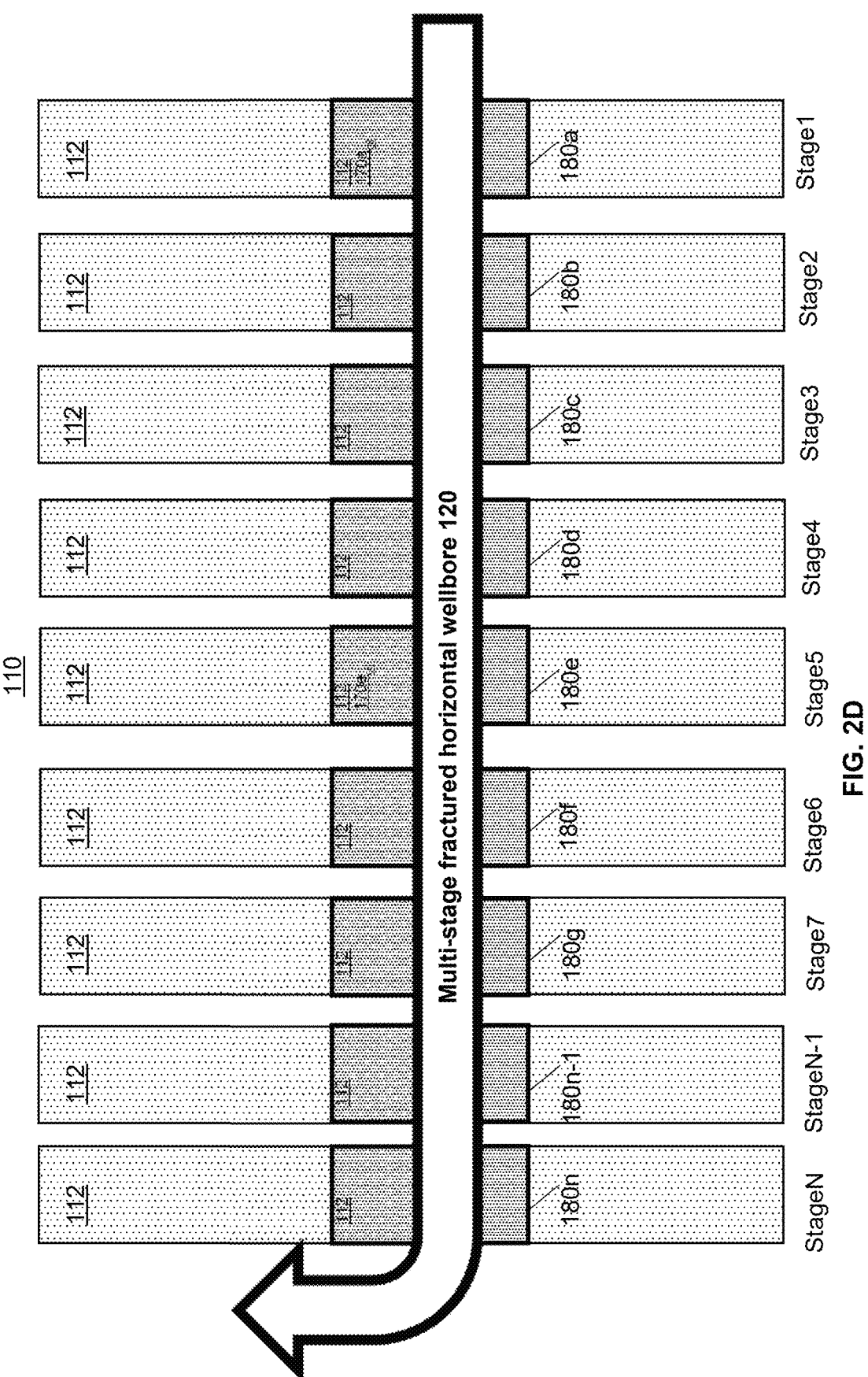
Figure 3A:
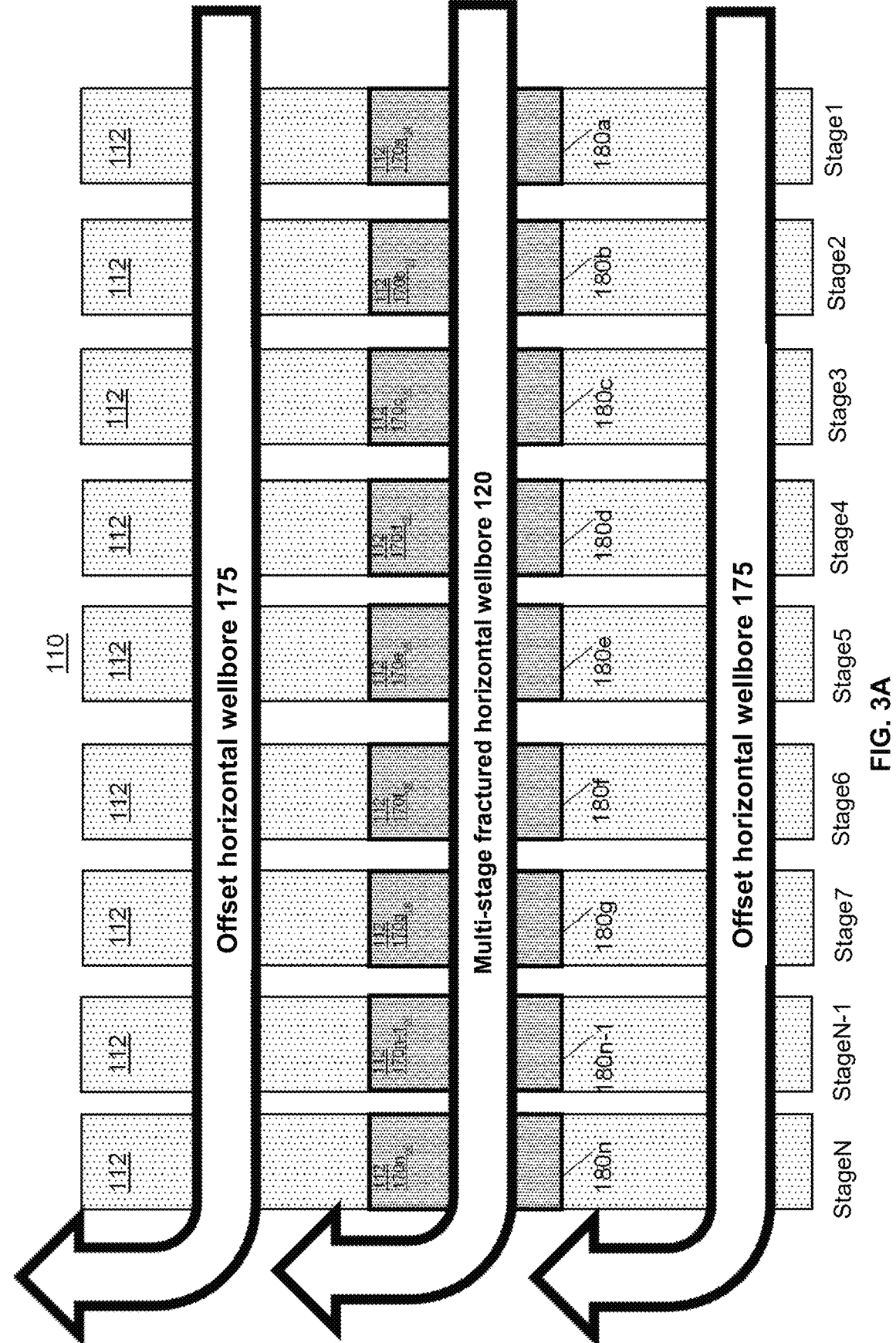
Figure 3B:
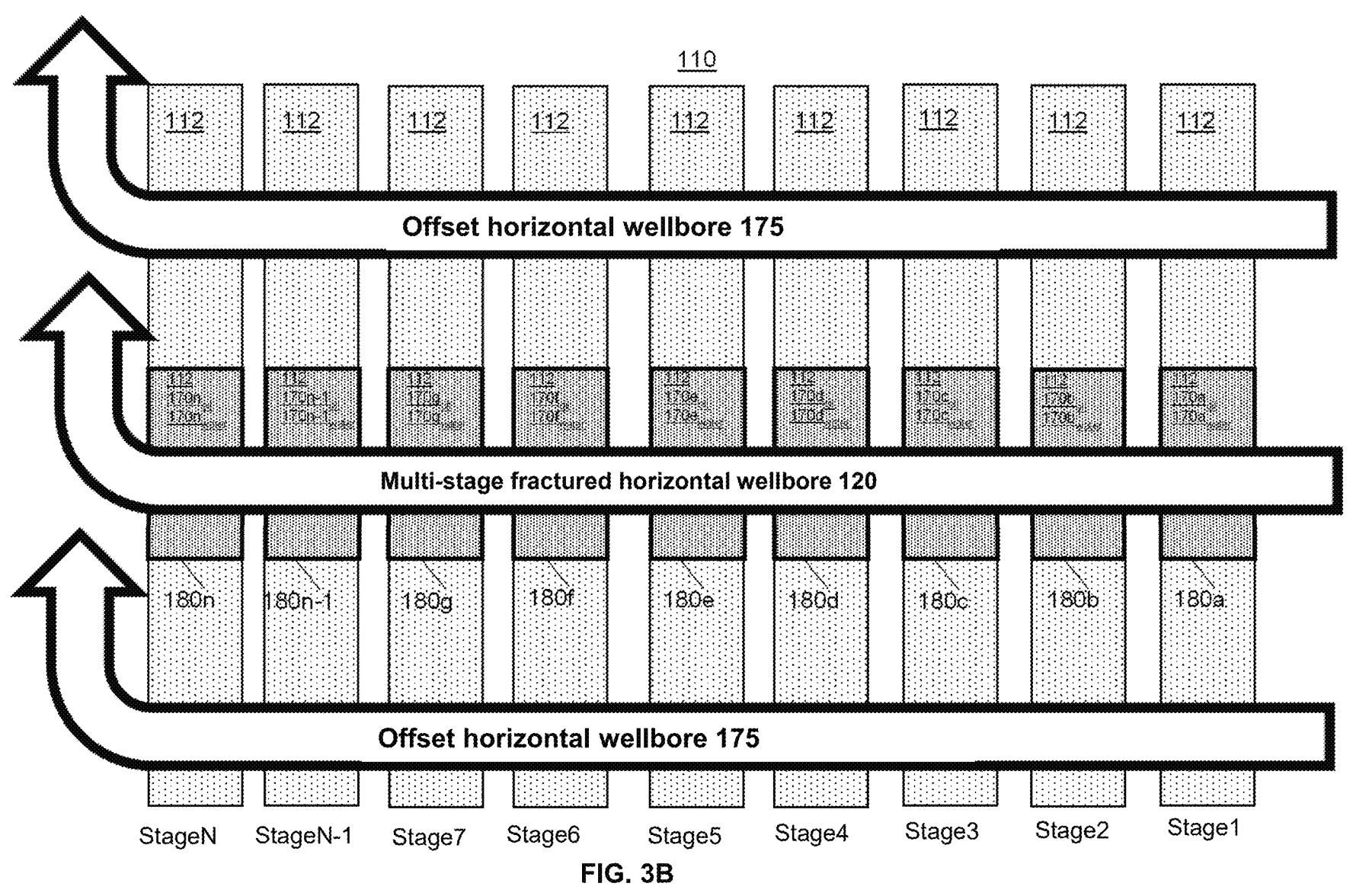
Figure 3C:
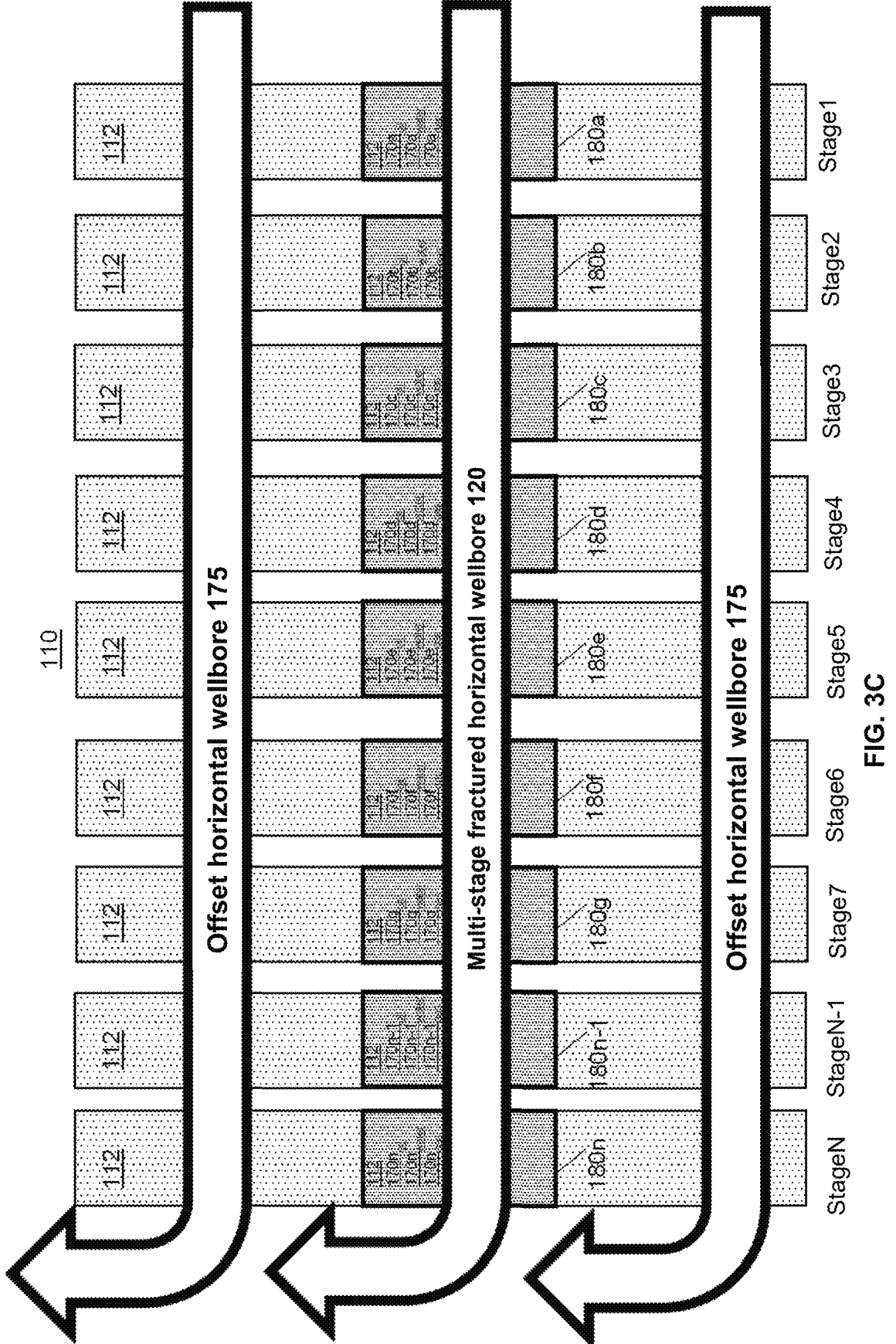

In contrast to the existing practice of placing unique particulate tracers, in the example embodiments of the present disclosure the unique particulate tracers are pumped only in a fraction of each stage such that a substantial portion of the unique particulate tracers are placed in a near wellbore region of the subsurface formation proximate to the wellbore. FIGS. 2A, 2B, and 2C illustrate non-limiting embodiments of placing unique particulate tracers in a subterranean formation having a wellbore therewithin consistent with the instant disclosure. In FIGS. 2A, 2B, and 2C, the proppant 112 is pumped in the entirety of each Stage1 through StageN for the single wellbore 120 as in FIGS. 1D-1, 1D-2, and 1D-3. However, unique particulate tracers 170 (illustrated as 170a$_{oil}$, 170b$_{oil}$, and so on) are pumped only in a fraction of each stage such that a substantial portion of the unique particulate tracers 170 are placed in a near wellbore region 180 (illustrated as 180a for the near wellbore region corresponding to Stage1, 180b for the near wellbore region corresponding to Stage2, and so on) of the subterranean formation 110 proximate to the wellbore 120. The unique particulate tracers 170 are pumped with the proppant 112 in the near wellbore region 180. At least one unique particulate tracer is pumped in the fraction of each stage, and each unique particulate tracer corresponds to an oil phase, a water phase, or a gas phase.

Advantageously, a lower quantity of unique particulate tracers is utilized in embodiments consistent with the disclosure because the unique particulate tracers are placed in the near wellbore region and not throughout each stage and/or stage group. Moreover, as will be described further herein, embodiments are provided in this disclosure related to placing unique particulate tracers in fewer stages than all the stages that are available, such as placing particulate tracers 170 in three stages (e.g., Stage1, Stage5, and StageN) of the nine stages that are illustrated in FIGS. 2A, 2B, and 2C, to further decrease the quantity of unique particulate tracers that is utilized without significantly impacting the analysis.

Advantageously, the placement of the unique particulate tracers in the near wellbore region focuses or concentrates the particulate tracers in this area, which may increase the accuracy of flow rates that are generated based on the unique particulate tracers. The existing practice typically does not provide an economic, scalable, and accurate way to generate flow rates (e.g., absolute barrels per day) and/or flow profiles (e.g., percentages) in unconventional long horizontal wells. Embodiments consistent with the instant disclosure may provide a cost-effective, long term, non-interventional, and accurate way of profiling the production from individual stages of multi-stage hydraulically fractured wellbores. This may also allow for optimization of hydrocarbon production from unconventional resources. The determined flow rates and/or flow profiles may be utilized for completion design optimization, understanding changes in flow profiles as a function of time, understand rock type proximate to the wellbore, where to drill a wellbore, understand production from different parts of the lateral that can be utilized to optimize wellbore length and/or wellbore landing, understand possible optimization equipment or techniques for increasing hydrocarbon recovery, etc. The wellbore may comprise a vertical trajectory, a horizontal trajectory, or a deviated trajectory. The subterranean formation may be located onshore or located offshore.

Figure 4:
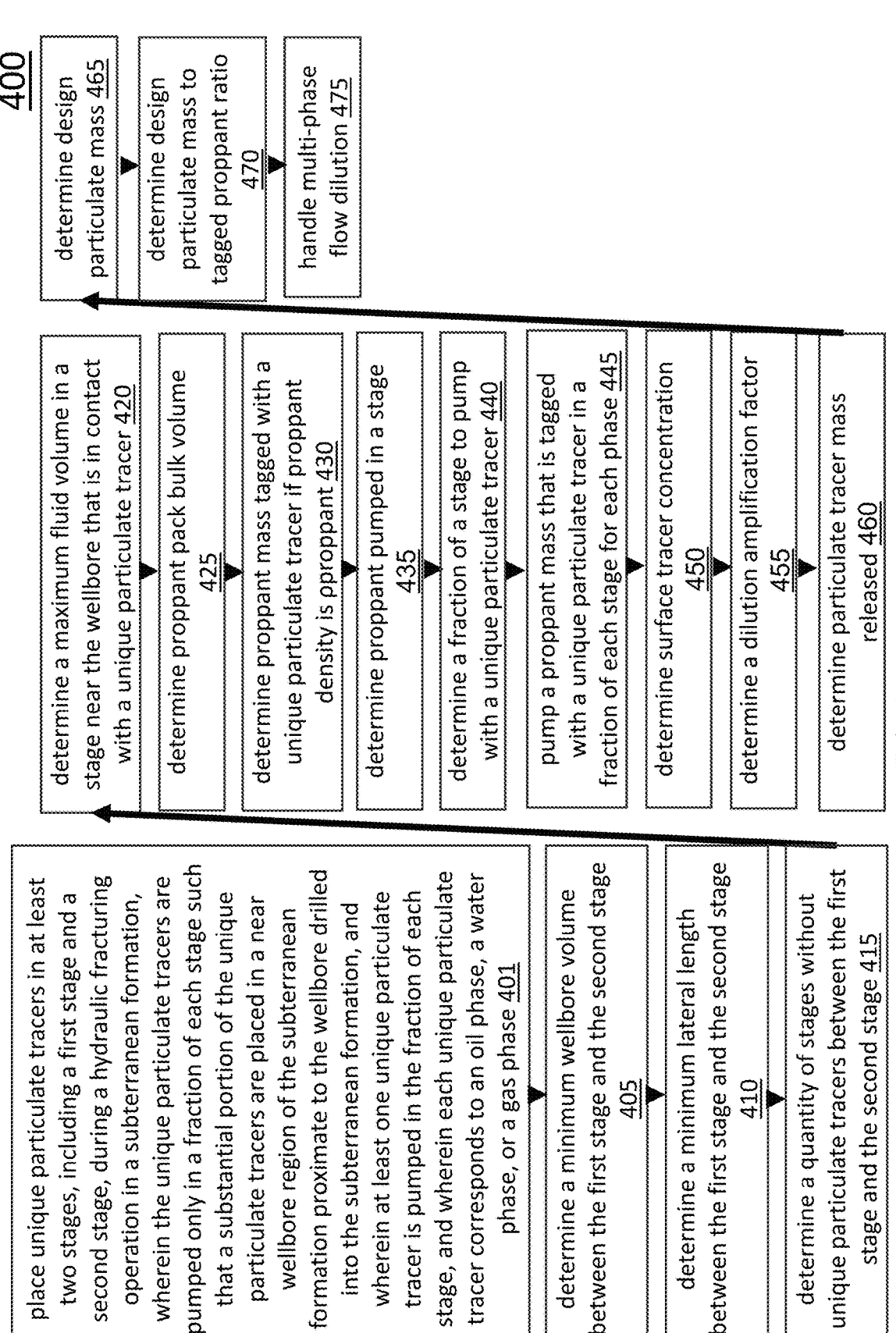
FIG. 4 illustrates an example method of placing unique particulate tracers in a subterranean formation having a wellbore therewithin.

FIG. 4 illustrates an example method of placing unique particulate tracers in a subterranean formation having a wellbore therewithin referred to as a method 400. The unique particulate tracers may be practically any unique particulate tracers known in the art, such as unique particulate tracers for hydrocarbons (e.g., oil), unique particulate tracers for water, unique particulate tracers for gas, or any combination thereof. For example, types of particulate tracers that are introduced into the subterranean formation may include, but are not limited to, fluorinated benzoic acids (FBAs), fluorescein dyes, FBA/fluorescein synthesis, fluorescing nanocrystals, radioactive tracers, fluorescing nanoparticles, magnetic nanoparticle tracers, etc.

While the various steps in one embodiment of the method 400 are presented sequentially, one of ordinary skill will appreciate that some or all of the steps may be executed in different orders, may be combined or omitted, and some or all of the steps may be executed in parallel. Further, in one or more of the example embodiments, one or more of the steps shown in this example method may be omitted, repeated, and/or performed in a different order. Furthermore, a person of ordinary skill in the art will appreciate that any equations utilized herein may be modified without changing the meaning, for example, an equation may be modified to use different units such as metric units without changing the meaning. A person of ordinary skill in the art will appreciate that additional steps not shown in FIG. 4 may be included in performing this method. A person of ordinary skill in the art will appreciate that fewer than the steps shown in FIG. 4 may be used in performing this method of pumping unique particulate tracers only in a fraction of each stage. The method shown in FIG. 4 is merely one embodiment that can be performed by using a system, such as described in FIGS. 1A, 1B, 1C, and 36.

Referring to FIG. 4, the method 400 of FIG. 4 includes step 401 of placing unique particulate tracers in at least two stages, including a first stage and a second stage, during a hydraulic fracturing operation in a subterranean formation. The unique particulate tracers are pumped only in a fraction of each stage such that a substantial portion of the unique particulate tracers are placed in a near wellbore region of the subterranean formation proximate to the wellbore drilled into the subterranean formation. At least one unique particulate tracer is pumped in the fraction of each stage, and each unique particulate tracer corresponds to an oil phase, a water phase, or a gas phase. For example, a unique oil particulate tracer may be pumped only in a first fraction of a first stage of a stage pair and a different unique oil particulate tracer may be pumped only in a second fraction of a second stage of the stage pair. The unique particulate tracers may be pumped using existing techniques and existing equipment as illustrated, for example, in FIGS. 2A, 2B, 2C, 3A, 3B, and 3C. FIG. 4 may be applied to at least two stages and fewer than all the stages. In the running example based on FIGS. 2D and 7A-7G, the unique particulate tracers 170$a_{oil}$ and 170$e_{oil}$ will be placed in Stage1 in near wellbore region 180$a$ and Stage5 in near wellbore region 180$e$, respectively. Stage1 (e.g., first stage) and Stage5 (e.g., second stage) are a stage pair. The rest of FIG. 4 includes different equations that may facilitate the placement of step 401.

The method 400 of FIG. 4 includes step 405 to determine a minimum wellbore volume between the first stage and the second stage. In the running example, the unique particulate tracers 170$a_{oil}$ and 170$e_{oil}$ will be placed in Stage1 and Stage5 respectively, and the minimum wellbore volume between Stage1 and Stage5 may be determined at step 405. The minimum wellbore volume may be determined using Equation 1 below. The Equation 1 is solved once of each phase.

$$V_{wellbore,min} bbls = q_{min} * t_{fs} * \frac{1}{24*60} \qquad \text{Equation 1}$$

- wherein $V_{wellbore,min}$ is minimum wellbore volume between two unique particulate tracer placements (e.g., in bbls)

- wherein $q_{max}$ is maximum flow rate (e.g., in bbls)

- wherein $t_{fs}$ is sampling frequency (e.g., in minutes)

- Of note:If metric units are utilized, then the following portion of Equation 1 may be omitted: $* \frac{1}{24*60}$ Running Example Using Equation 1:

$17bbls = 5000bpd * 5 \text{ minutes} * \frac{1}{24*60}$

The method 400 includes step 410 to determine a minimum lateral length between the first stage and the second stage. In the running example, the unique particulate tracers

170$a_{oil}$ and 170$e_{oil}$ will be placed in Stage1 and Stage5 respectively, and the minimum lateral length between Stage1 and Stage5 may be determined at step 410. The determined minimum wellbore volume from step 405 and a flow pipe radius (referred to as $r_w$) may be utilized to determine the minimum lateral length. The flow pipe radius may correspond to production casing or production tubing. The minimum wellbore length may be determined using Equation 2 below. The Equation 2 is solved once for each phase.

$$L_{wellbore,min} ft = \frac{V_{wellbore,min}}{\pi r_w^2} \qquad \text{Equation 2}$$

- wherein $L_{wellbore,min}$ is minimum lateral length between two unique particulate tracer placements (e.g., in feet)

- wherein $r_w$ is a flow pipe radius (e.g., wellbore diameter in inches)

Running Example Using Equation 2:

$591 \text{ feet} = \frac{17bbls}{\pi 5.5 \text{ inches}^2}$

Parameters on which the tracer placement for flow profiling depend are provided and these are utilized in the Equations 1-2 hereinabove: (a) max expected flowrate from the well: $q_{max}$ bbls/day, and (b) fastest sampling frequency at surface post shut-in possible at the surface ($t_{fs}$ minutes): such as 5-minute interval. Moreover, this unique tracer placement at the above minimum lateral length may allow for obtaining non-overlapping signals at the surface at the practical sampling frequency of 1 sample every 5 minutes.

The method 400 includes step 415 to determine a quantity of stages without unique particulate tracers between the first stage and the second stage. In the running example, the unique particulate tracers will not be placed in three stages (i.e., Stage2, Stage3, and Stage4 in FIG. 2D) using the minimum lateral length between Stage1 and Stage5 that was determined at step 410. The quantity of stages without unique particulate tracers may be determined using Equation 3 below. The Equation 3 is solved once for each phase.

$$\text{quantity of stages without unique particulate tracers between} \qquad \text{Equation 3}$$
$$\text{two unique particulate tracer placements} = \frac{L_{wellbore,min}}{Lstage}$$

- wherein $L_{wellbore,min}$ is minimum lateral length between two unique particulate tracer placements (e.g., in feet)

- wherein $Lstage$ is stage length (e.g., in feet)

Running Example Using Equation 3:

$3 \text{ stages} = \frac{591 \text{ feet}}{200 \text{ feet}}$

The method 400 includes step 420 to determine a maximum fluid volume in a stage near the wellbore that is in contact with a unique particulate tracer, which will be utilized later herein to determine a fraction of each stage in which to pump a unique particulate tracer. If the unique particulate tracers are placed inside the subterranean formation with proppant, and the stage in which the tracers are placed does not flow at a sufficient rate, then the particulate tracer signals would overlap inside the wellbore and would not stay distinct, which is used for flow profiling. Thus, minimum flowrate $q_{min,stage}$ (e.g., bbls/day) from a stage is a design parameter to determine tracer placement within the stage. The maximum fluid volume in a stage near the wellbore that is in contact with a unique particulate tracer may be determined using Equation 4 below. The Equation 4 is solved once for each phase.

$$V_p bbls \le q_{min,stage} * \frac{t_{fs}}{24 * 60} \qquad \text{Equation 4}$$

- wherein $V_p$ is a maximum fluid volume in a stage near the wellbore that is in contact with unique particulate tracer (e.g. in $bbls$)

- wherein $q_{min,stage}$ in minimum flowrate from a stage (e.g., in $bbls$)

- wherein $t_{fs}$ is sampling frequency (e.g., in minutes)(e.g., ~5 minutes)

Of note:If metric units are utilized, then the following portion of Equation 4 may be omitted:$24 * 60$ Running Example Using Equation 4:

$$1.041667 bbls \le 300 bpd * \frac{5 \text{ minutes}}{24 * 60}$$

The method 400 includes step 425 to determine proppant pack bulk volume, which will be utilized later herein to determine a fraction of each stage in which to pump a unique particulate tracer. The corresponding proppant packing bulk volume, $V_{bulk-proppant}$, if the proppant pack porosity is Ø, may be determined using Equation 5 below. The Equation 5 is solved once for each phase.

$$V_{bulk-proppant}, bbls = \frac{V_p}{\phi} * (1 - \phi) \qquad \text{Equation 5}$$

wherein $V_{bulk-proppant}$ is proppant pack bulk volume (e.g., in $bbls$)

wherein $V_p$ is a maximum fluid volume in stage near the wellbore that is in contact with unique particulate tracer (e.g., in $bbls$)

wherein $\phi$ is proppant pack porosity

Running Example Using Equation 5:

$$2.430556 bbls = \frac{1.041667}{0.30} * (1 - 0.30)$$

The method 400 includes step 430 to determine proppant mass tagged with a unique particulate tracer if proppant density is $\rho_{proppant}$ (e.g., lbs/gallon), which will be utilized later herein to determine a fraction of each stage in which to pump a unique particulate tracer. Tagged refers to includes as in what is the proppant mass that includes a unique particulate tracer. The proppant mass tagged with unique particulate tracer may be determined using Equation 6 below. The Equation 6 is solved once for each phase (add claim).

$$\text{tagged proppant mass, } lbs = 42 * V_{bulk-proppant} * \rho_{proppant} \qquad \text{Equation 6}$$

wherein tagged proppant mass is proppant mass tagged with the unique particulate tracers (e.g., in $lbs$)

wherein $V_{bulk-proppant}$ is proppant pack bulk volume (e.g., in $bbls$)

wherein $\rho_{proppant}$ is proppant density (e.g., $lbs$/gallon)

-continued

Of note:If metric units are utilized, then the following portion of Equation 6 may be omitted: $42 *$ Running Example Using Equation 6:

$$2256.144 lbs = 42 * 2.430556 bbls * 22 \frac{lb}{gal}$$

Of note:$\rho_{proppant}$ of 22 lb/gal was determined by $2.65 gm/cc * 8.34$.

The method 400 includes step 435 to determine proppant pumped in a stage, which will be utilized later herein to determine a fraction of each stage during which to pump a unique particulate tracer. During fracture design, each stage gets completed with $M_{p,stage}$ (e.g., lbs) of proppant. The proppant pumped in a stage may be determined using Equation 6 below. The Equation 7 is solved once, and substantially the same answer is utilized for each phase.

$$M_{p,stage} lbs = \text{proppant intensity} * L_{stage} \qquad \text{Equation 7}$$

wherein $M_{p,stage}$ is proppant pumped in a stage (e.g., in $lbs$)

wherein proppant intensity may be expressed as lb/ft wherein $L_{stage}$ is length of stage (e.g., inches)

Running Example Using Equation 7:

$$440000 lbs = 2000 \frac{lb}{ft} * 200 \text{ feet}$$

The method 400 includes step 440 to determine a fraction of a stage in which to pump a unique particulate tracer. In some embodiments, a fraction comprises 0.001% to 10%. In some embodiments, a fraction comprises 0.001% to 25%. In some embodiments, a fraction comprises 0.001% to 50%. In some embodiments, the same fraction may be utilized for each stage. The fraction of a stage in which to pump a unique particulate tracer may be determined using Equation 8 below: The Equation 8 is solved once for each phase.

$$\text{fraction of stage tagged with a unique particulate tracer} = \frac{\text{Tagged proppant mass, } lbs}{M_{pstage} lbs} \qquad \text{Equation 8}$$

wherein fraction of stage tagged with a unique particulate tracer is percentage of a stage wherein tagged proppant mass is proppant mass tagged with a unique particulate tracer (e.g., in $lbs$)

wherein $M_{p,stage}$ is proppant pumped in a stage (e.g., in $lbs$)

Running Example Using Equation 8:

0.0051 percent of stage tagged with a unique particulate tracer =

$$\frac{2256.144 lbs}{440000 lbs}$$

Of note:0.0051 may be represented as 0.51% of stage tagged with a unique particular tracer In the running example, the fraction is a percentage of the stage such as 0.51% of the stage, and the whole stage is 100%. Regarding steps 430, 435, and 440, in the running example, about 2256.144 lbs of the proppant 112 will be tagged with the unique particulate tracer 170$a_{oil}$ in 0.51% (i.e., fraction) of Stage1 out of about 440,000 lbs of the proppant 112 that will be pumped into the Stage1. Existing practice would have added particulate tracers throughout the 440,000 lbs of proppant in Stage1. Similarly, about 2256.144 lbs of proppant 112 will be tagged with the unique particulate tracer 170$e_{oil}$ in 0.51% (i.e., fraction) of Stage5 out of the about 440,000 lbs of the proppant 112 that will be pumped into the Stage5. Thus, this running example illustrates a substantial reduction in the quantity of unique particulate tracers that will be utilized in Stage1 and Stage5. The fraction of 0.51% may translate to about 1 minute of pumping time.

The method 400 includes a step 445 to pump a proppant mass that is tagged with a unique particulate tracer in a fraction of each stage for each phase. The unique particulate tracer is pumped in the determined fraction at the start and/or at the end of a stage injection such that a substantial portion of the unique particulate tracer is placed in a near wellbore region of the subterranean formation proximate to the wellbore of the corresponding stage. Start of stage injection: Based on some geomechanical models, early in the stage injected proppant stays close to the wellbore. End of stage injection: Conventional thinking is that the proppant injected at the end stays close to the wellbore. In the running example, the 2256.144 lbs of the proppant 112 tagged with the unique particulate tracer 170$a_{oil}$ may be pumped in 0.51% (i.e., fraction) of Stage1 at the start of the stage injection or at the end of stage injection such that the proppant 112 tagged with the unique particulate tracer 170$a_{oil}$ is pumped into the near wellbore region 180$a$. In the running example, the 2256.144 lbs of the proppant 112 tagged with the unique particulate tracer 170$e_{oil}$ may be pumped in 0.51% (i.e., fraction) of Stage5 at the start of the stage injection or at the end of stage injection such that the proppant 112 tagged with the unique particulate tracer 170$e_{oil}$ is pumped into the near wellbore region 180$e$. Pumping of the fraction of a stage with proppant mass tagged with the unique particulate tracer at the start/end of stage treatment will allow for the tracer to be placed in the near wellbore region.

For pumping, a unique particulate tracer may be kept in an isolation tank and the proppant may be kept in a different isolation tank, and then both get added to the fracturing fluid and the fracturing fluid is injected. Separate pumps for the proppant and the the unique particulate tracer may be utilized until they are mixed in the stream (e.g., stream of fracturing fluid). Afterwards, there may be other pumps that further pressurize the mix to be pumped into the wellbore.

Figure 5:
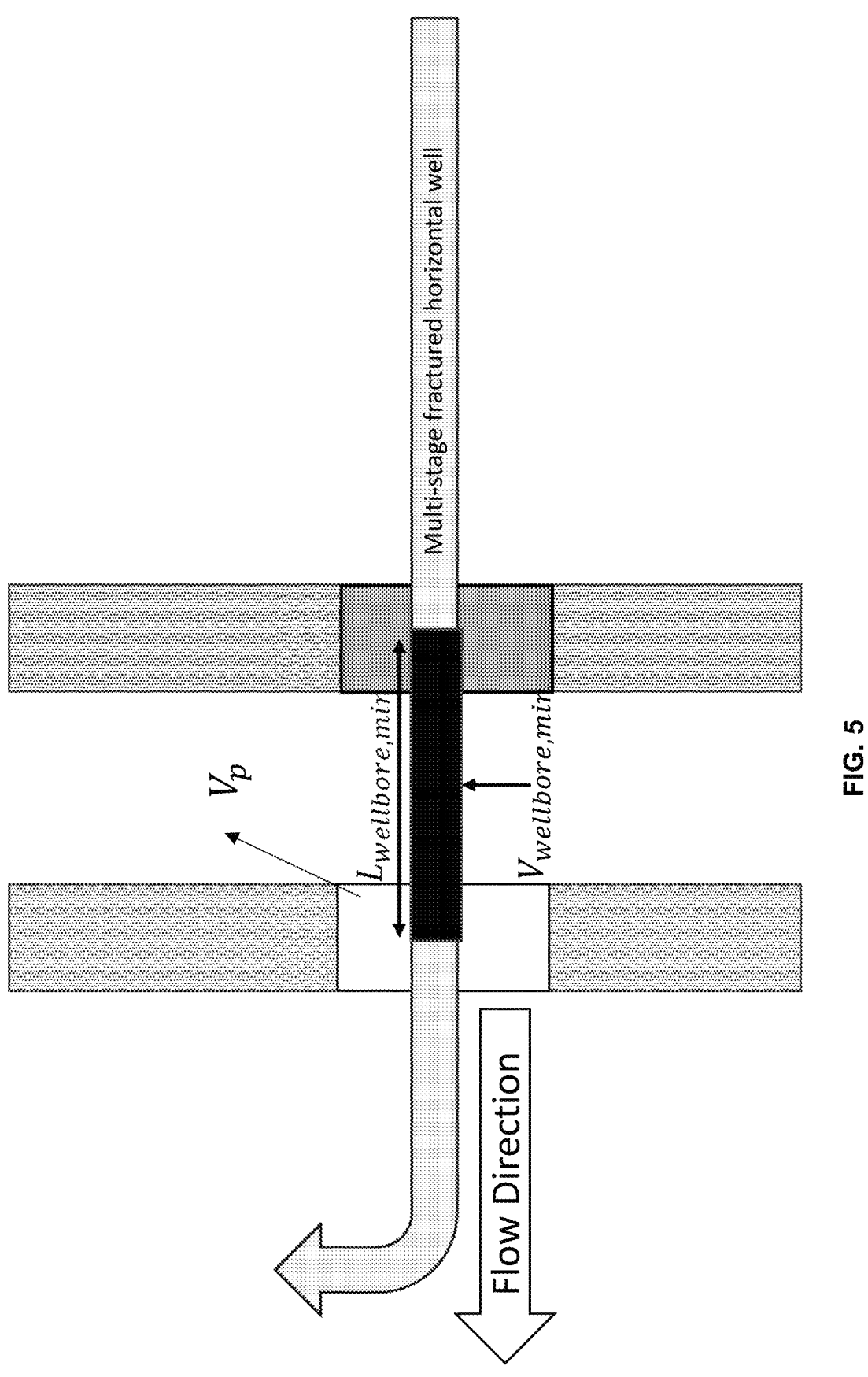
FIG. 5 illustrates an example of V$_{wellbore,min}$ and L$_{wellbore,min}$.

Additional information: The particulate tracer placement design discussed before allows for the tracer dilution between the volume contained between the locations/stages where the two unique particulate tracers are placed $V_{wellbore, min}$ bbls is mixed with the volume of fluid flowing from the stage downstream $V_p$ bbls because the placement is designed such that the time it takes for the fluid to flow in the wellbore from upstream (e.g., location closer to the wellbore's toe) to downstream (e.g., location closer to the wellbore's heel) is less than equal to time it would take particulate contacted volume downstream to flow into the wellbore and mix with the total stream. This would also be the maximum dilution that the tracer would undergo in theory and would be what would be observed at the surface. This is illustrated in FIG. 5.

The method 400 includes step 450 to determine surface tracer concentration. This relationship is used to determine the amount of unique particulate tracer mass to be injected. In one embodiment, the tracer concentration observed at the surface should at least be the equivalent to the tracer quantification limit as determined by a conventional lab analytical method. For most unique particulate tracers such a limit is ~5 ppb. In one embodiment, a phase amplification factor may also be incorporated while using this relationship to determine the unique particulate tracer mass design. The surface tracer concentration may be determined using equation 9 below. The surface observed tracer concentration with dilution would be Equation 9. The Equation 9 is solved once for each phase.

Tracer *conc.* @ surface, $$ppb = \frac{\text{Particulate tracer mass released from } V_p, lbs}{\text{Mass of fluid in } (V_{wellbore,min} + V_p), lbs} * 10^9 \qquad \text{Equation 9}$$

The method 400 includes step 455 to determine a dilution amplification factor. In one embodiment, the dilution amplification factor could be the ratio of wellbore volume between two tracer placements to the total wellbore volume because it removes any dilution related uncertainty that could be a part of the design. The dilution amplification factor may be determined using Equation 10 below. The Equation 10 is solved once for each phase.

Dilution amplification factor =

$$\frac{(\text{Total wellbore volume } (V_{wellbore,total}bbls))}{\begin{array}{c}Min \text{ Wellbore volume between two} \\ \text{particulate tracer placement } (V_{wellbore,min}bbls)\end{array}} \qquad \text{Equation 10}$$

Running Example Using Equation 10:

$$26 = \frac{450bbls}{17bbls}$$

The method 400 includes step 460 to determine particulate tracer mass released, which is a minimum to be released in the subsurface in order to see at least 5 ppb in the surface. The tracer mass in the particulate contacted volume $V_p$ using the below constraint (detection, quantification limit) from laboratory analysis: The Equation 11 is solved once for each phase.

Tracer *conc.* @ surface, $$ppb \geq \text{Detection, quantification limit}, ppb \qquad \text{Equation 11}$$

Figure 6:
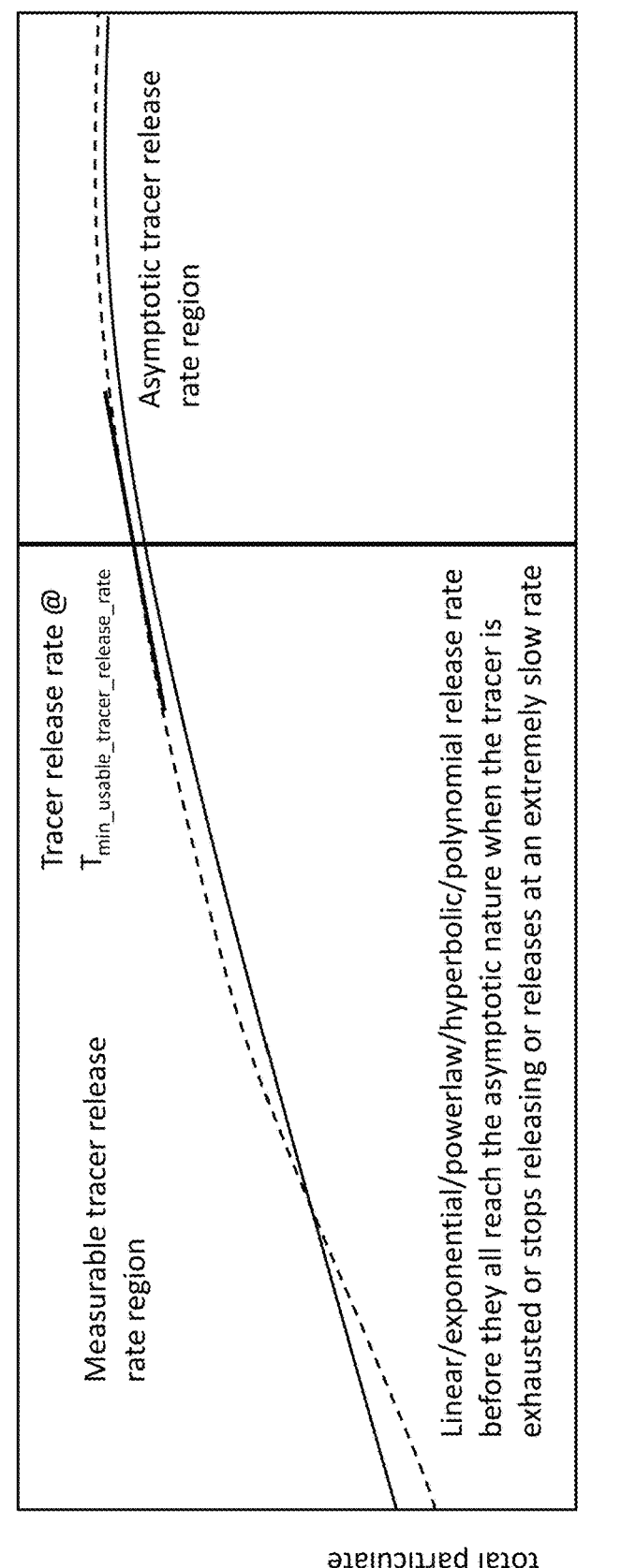
FIG. 6 illustrates an expected tracer release rate plot.
Figure 7D:
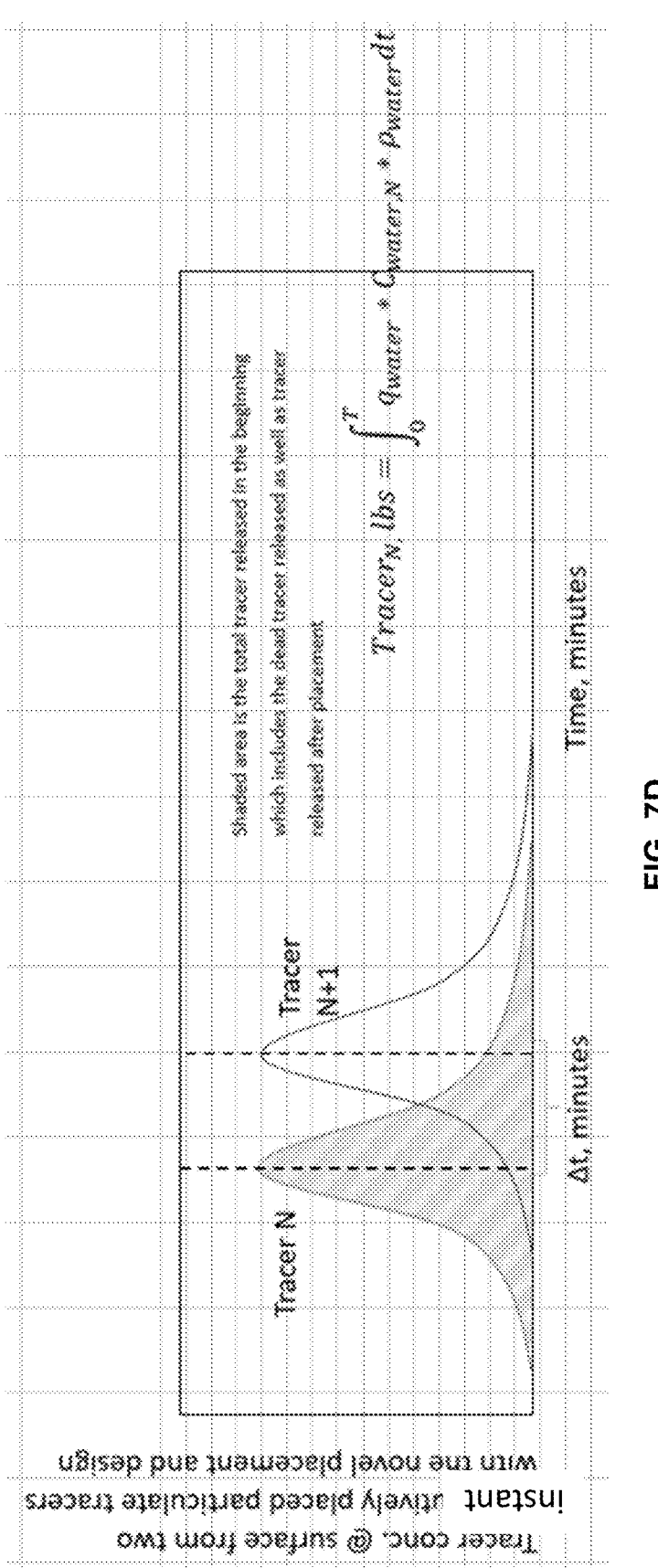
Figure 7F:
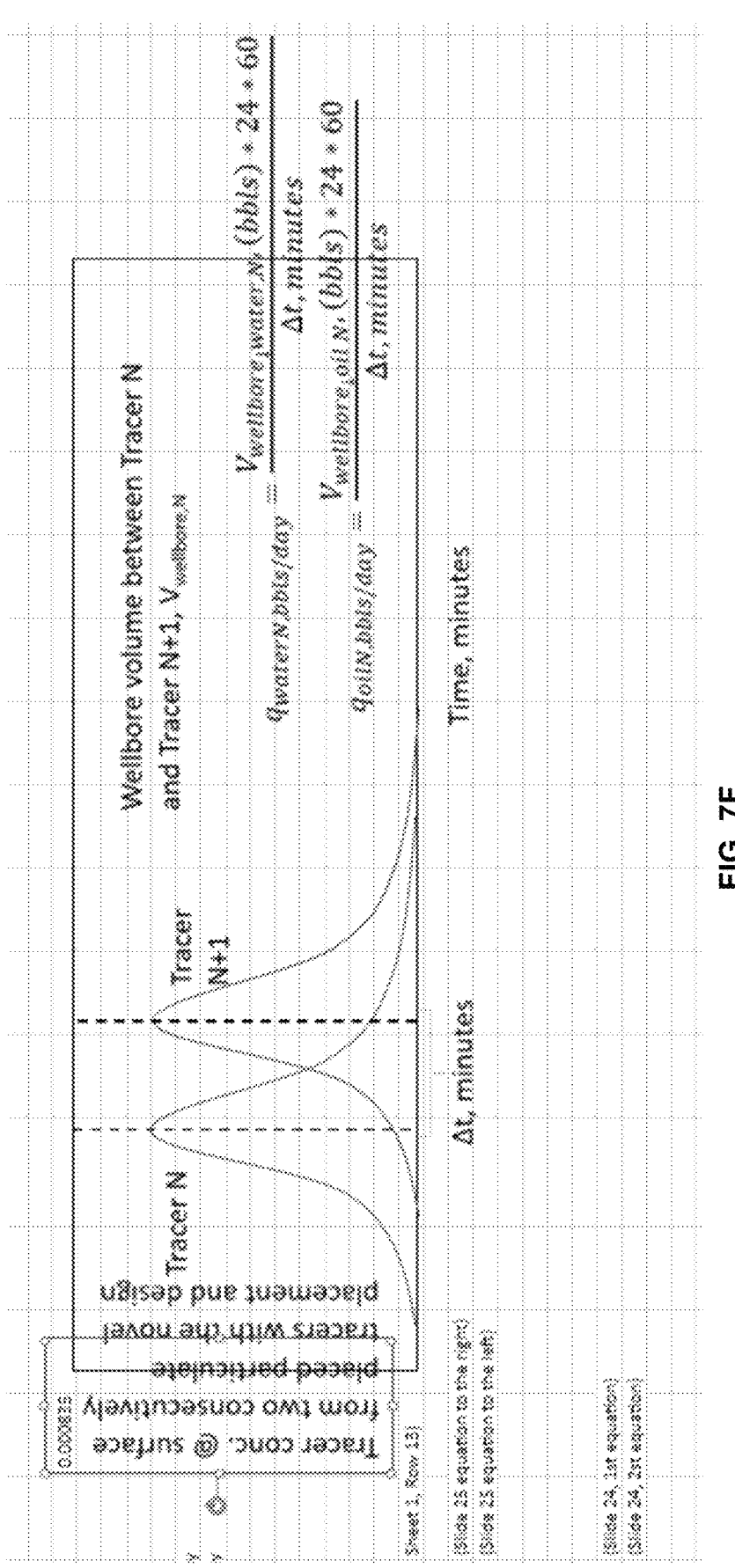

With tracer release rate from a unique particulate tracer measured in the lab, the actual mass of a unique particulate tracer to be injected in the fraction of a stage in the improved configuration could be determined. The expected tracer release rate plot is shown in FIG. 6. The detection, quantification limit may be 5 ppb in one embodiment. The detection, quantification limit may be in a range of 0.1 ppb to 100 ppb. In another embodiment, the detection, quantification limit may be in a range of 0.1 ppb to 10 ppb in another embodiment. The detection, quantification limit may be 5 ppb or higher in another embodiment. In one embodiment, the detection, quantification limit may even be 0.1 ppb or lower. The particulate tracer mass released may be determined using Equation 12 below. The Equation 12 is solved once for each phase.

Equation 12 unique particulate tracer mass released, $$lbs = \frac{\text{Detection, quantification limit, } ppb * \text{Mass of fluid in } (V_{wellbore,min} + V_p) * \text{Dilution } Amp. \text{ factor}}{10^9}$$

wherein Tracer *conc.* @ surface, $$ppb \geq \text{Detection, quantification limit, } ppb$$

Of note: The Equation 12 uses concentration in *ppb* so we multiply the *RHS* by $10^9$, but if we use the concentration in *ppm* then we would multiply

*RHS* by $10^6$. Alternatively, if we use ceoncentration as true fraction/ratio then we would not multiply *RHS* with just 1.

Running Example Using Equation 12:

$$0.000835418 lbs = \frac{5 ppb * 6446.125 lbs * 26}{10^9}$$

wherein Tracer *conc.* @ surface, $ppb \geq 5 ppb$

The method 400 includes step 465 to determine design particulate mass. The amount of tracer released from the particulate tracers is a function of the injected tracer mass as well as the exposure time of the tracer to the fluid which could be seen from the release rate. A typical well shut-in duration $t_{shutin}$ is ~24 hours so the tracer concentration could be built for analysis would lead to the following particulate mass for injection using the release rate @ $T_{min\_usable\_tracer\_release\_rate}$ so the design would still work for time less than $T_{min\_usable\_tracer\_release\_rate}$ because the release rates would be higher for those times. The Equation 13 is solved once for each phase.

Equation 13

Design particulate mass, $$lbs = \frac{t_{shutin} * \text{particulate tracer mass released, } lbs}{24 * min. \text{ usable tracer mass released rate @ } T_{min\_usable\_tracer\_release\_rate}\left(\frac{\frac{lbs}{lbs}}{day}\right)}$$

Of note: The equation could have the 24 removed from the denominator if everything else is in standard units.

Running Example Using Equation 13:

$$22 lbs = \frac{24 * 0.000835418 lbs}{24 * 3.79735E - 05\left(\frac{\frac{lbs}{lbs}}{day}\right)}$$

The method 400 includes step 470 to determine design particulate mass to tagged proppant ratio. The Equation 14 is solved once for each phase.

Equation 14

Design particulate mass to tagged proppant ratio =

$$\frac{\text{Design particulate mass, } lbs}{\text{Tagged proppant mass, } lbs}$$

-continued
Running Example Using Equation 14:

$$0.009751152 = \frac{22 lbs}{2256.144 lbs}$$

The method 400 includes step 475 to handle multi-phase flow dilution. With phase amplification factor introduced in the design, the produced tracer concentrations would still be at quantification limit as long as the WOR is equal to or greater than the phase amplification factor for water tracers and vice versa for oil tracers. The Equation 15 is solved once for each phase.

Water particulate tracer surface concentrations ≥    Equation 15

Quantifiable Limit if $WOR \geq$ Phase Amplification Factor

With large phase amplification factors, if the water or oil tracer fall below detectable limit, the flowrate of the respective phase is small compared to the other phase and thus should be the main flow phase of concern. The Equation 16 is solved once for each phase.

Oil particulate tracer surface concentrations ≥    Equation 16

Quantifiable Limit if $WOR \geq \dfrac{1}{\text{Phase Amplification Factor}}$

The improved implementation of unique particulate tracers with the design methodology outlined is similarly applicable to both oil and water particulate tracers. With oil and water flowing simultaneously, the way the improved application is designed would account for reduction in the tracer mass for oil or water and a corresponding increase in the tracer mass for water or oil if contact area changes between water and oil particulate tracers and its corresponding reduction in the tracer concentration because overall flowrate of the corresponding phase also goes down along with the dilution.

Each of the following items are incorporated by reference: (1) Jain, Lokendra, Doorwar, Shashvat, and Daniel Emery. "Analytical Tracer Interpretation Model for Fracture Flow Characterization and Swept Volume Estimation in Unconventional Wells." Paper presented at the SPE/AAPG/SEG Unconventional Resources Technology Conference, Houston, Tex., USA, July 2021; (2) U.S. Pat. No. 8,949,029; (3) Haitao Li, et al., Evaluation of the Release Mechanism of Sustained-Release Tracers and its Application in Horizontal Well Inflow Profile Monitoring, ACS Omega 2021 6 (29), 19269-19280; and (4) Flow loop testing to validate Tracerco's solid chemical inflow tracer technology, Tracerco Limited, 2021, available at tracerco.com.

Figure 8:
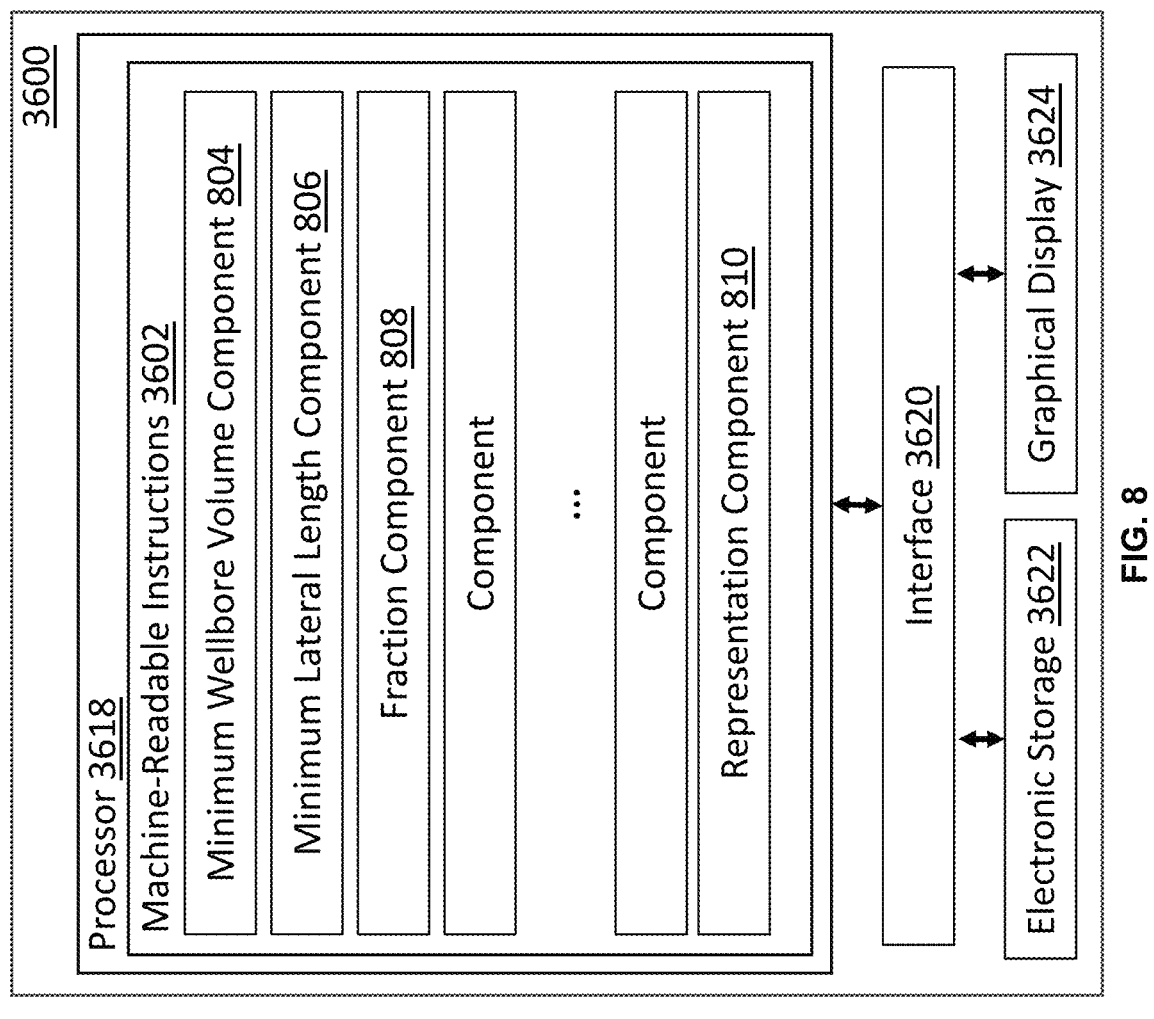
FIG. 8 illustrates an example computer system consistent with the disclosure.
Figure 16A:
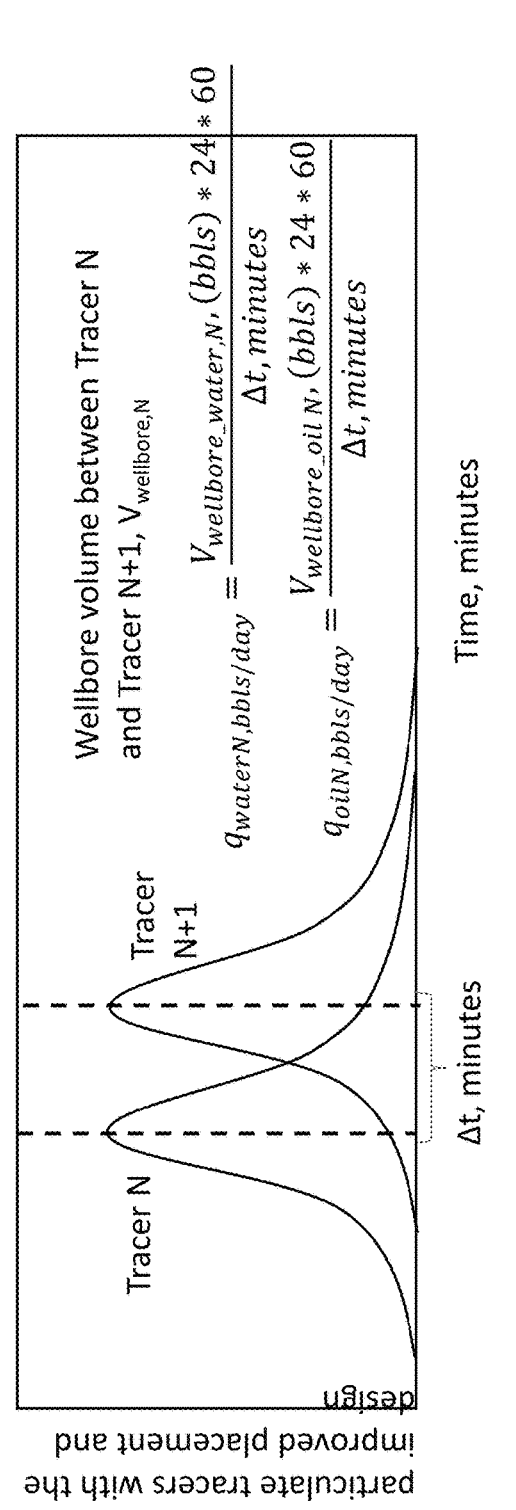
Figure 18A:
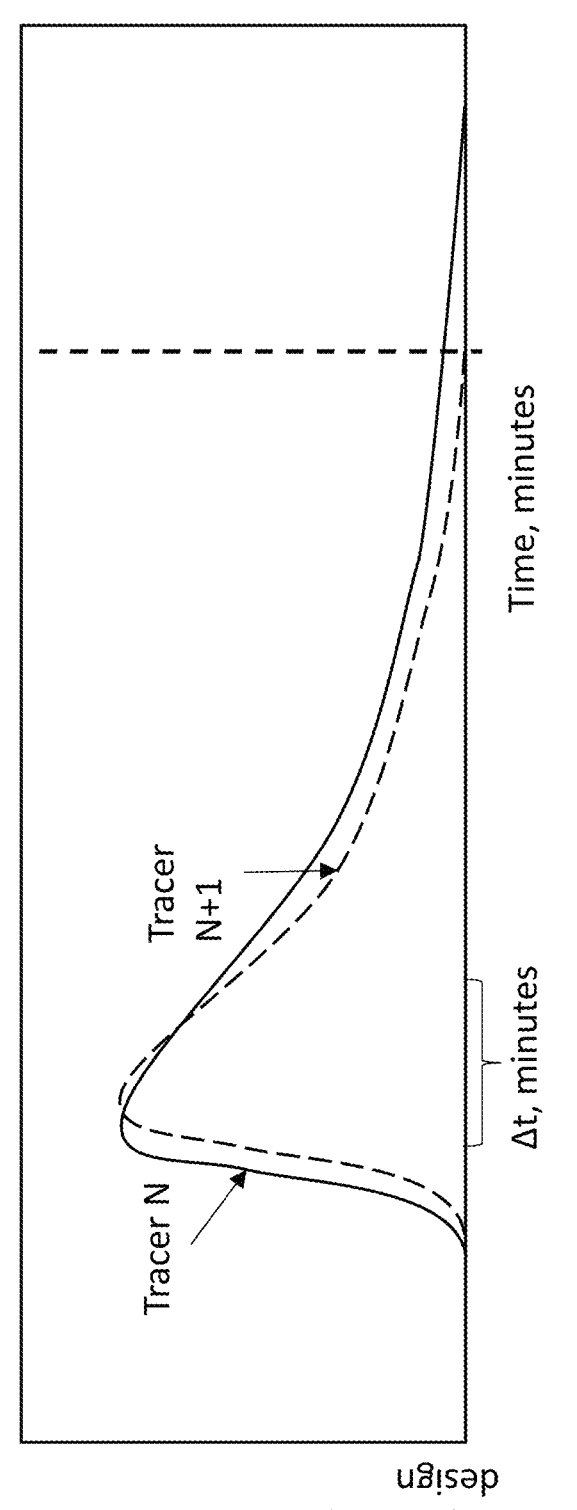

One or more of the steps described hereinabove in the method 400 of FIG. 4 may be implemented by a system and/or in a system, such as a system 3600 shown in FIG. 36 as illustrated in FIG. 8. For example, the step 405 to determine a minimum wellbore volume between the first stage and the second stage may be implemented by component 804 in FIG. 8. The step 410 to determine a minimum lateral length between the first stage and the second stage may be implemented by component 806 in FIG. 8. The step 440 to determine a fraction of a stage in which to pump a unique particulate tracer may be implemented by component

808 in FIG. 8. A representation of one or more of the values determined in the method 400 of FIG. 4 may be generated and displayed by component 810.

Determining a Flow Profile for a Wellbore Using Unique Particulate Tracers that are Pumped Only in a Fraction of Each Stage Such that a Substantial Portion of the Unique Particulate Tracers are Placed in a Near Wellbore Region of the Subterranean Formation Proximate to the Wellbore:

Reference will now be made in detail to various embodiments, examples of which are illustrated in the accompanying drawings. In the following detailed description, numerous specific details are set forth in order to provide a thorough understanding of the present disclosure and the embodiments described herein. However, embodiments described herein may be practiced without these specific details. In other instances, well-known methods, procedures, components, and mechanical apparatus have not been described in detail so as not to unnecessarily obscure aspects of the embodiments.

Example embodiments of determining a flow profile for a wellbore using unique particulate tracers will be described more fully hereinafter with reference to the accompanying drawings. The unique particulate tracers are pumped in at least one stage pair during a hydraulic fracturing operation performed in the subterranean formation, and wherein the unique particulate tracers are pumped only in a fraction of each stage such that a substantial portion of the unique particulate tracers are placed in a near wellbore region of the subterranean formation proximate to the wellbore. At least one unique particulate tracer is pumped in the fraction of each stage, and each unique particulate tracer corresponds to an oil phase, a water phase, or a gas phase. However, determining a flow profile may be embodied in many different forms and should not be construed as limited to the example embodiments set forth herein. Rather, these embodiments and examples are provided so that this disclosure will be thorough and complete, and will fully convey the scope of determining a flow profile to those of ordinary skill in the art. Like, but not necessarily the same, elements (also sometimes called components) in the various figures are denoted by like reference numerals for consistency.

FIG. 9 illustrates an example method of determining a flow profile for a wellbore using unique particulate tracers referred to as a method 900. The unique particulate tracers may be practically any unique particulate tracers known in the art, such as unique particulate tracers for hydrocarbons (e.g., oil), unique particulate tracers for water, unique particulate tracers for gas, or any combination thereof. For example, types of particulate tracers that are introduced into the subterranean formation may include, but are not limited to, fluorinated benzoic acids (FBAs), fluorescein dyes, FBA/fluorescein synthesis, fluorescing nanocrystals, radioactive tracers, fluorescing nanoparticles, magnetic nanoparticle tracers, etc.

While the various steps in one embodiment of the method 900 are presented sequentially, one of ordinary skill will appreciate that some or all of the steps may be executed in different orders, may be combined or omitted, and some or all of the steps may be executed in parallel. Further, in one or more of the example embodiments, one or more of the steps shown in this example method may be omitted, repeated, and/or performed in a different order. Furthermore, a person of ordinary skill in the art will appreciate that any equations utilized herein may be modified without changing the meaning, for example, an equation may be modified to use different units such as metric units without changing the meaning. A person of ordinary skill in the art will appreciate that additional steps not shown in FIG. 9 may be included in performing this method. A person of ordinary skill in the art will appreciate that fewer than the steps shown in FIG. 9 may be used in performing this method of determining a flow profile for a wellbore using unique particulate tracers. The method shown in FIG. 9 is merely one embodiment that can be performed by using a system, such as described in FIGS. 1A, 1B, 1C, and 36.

Referring to FIG. 9, the method 900 of FIG. 9 includes step 901 to obtain produced fluid samples comprising unique particulate tracers from a wellbore drilled into a subterranean formation. The unique particulate tracers are pumped in at least one stage pair (e.g., a first stage and a second stage) during a hydraulic fracturing operation performed in the subterranean formation. The unique particulate tracers are pumped only in a fraction of each stage such that a substantial portion of the unique particulate tracers are placed in a near wellbore region of the subterranean formation proximate to the wellbore. At least one unique particulate tracer is pumped in the fraction of each stage, and wherein each unique particulate tracer corresponds to an oil phase, a water phase, or a gas phase. Practically any known technique or known equipment may be utilized to obtain the produced fluid samples.

The method 900 of FIG. 9 includes step 905 to obtain a tracer concentration history for each unique particulate tracer, for example, as described herein.

The method 900 of FIG. 9 includes step 910 to determine a wellbore volume for the stage pair. In one embodiment, the wellbore volume is determined using an equation as follows:

$$V_{wellbore} = L_{wellbore} \text{ft} * \pi r_w^2$$

wherein $V_{wellbore}$ is wellbore volume, $L_{wellbore}$ft is length for a specific stage pair (e.g., length between a first stage and a second stage of a stage pair), and $r_w$ is a flow pipe radius. The wellbore volume may be solved once, and substantially the same answer may be reused for various stage pairs.

The method 900 of FIG. 9 includes step 915 to determine a flow profile for the wellbore for each phase indicative of flow contribution for each stage pair and stages in between each stage pair using the wellbore volume and the corresponding tracer concentration histories. In one embodiment, the flow contribution is determined using an equation as follows:

$$q_{N,bbls/day} = \frac{V_{wellbore,N}, (bbls) * 24 * 60}{\Delta t, \text{minutes}}$$

wherein $q_{N,bbls/day}$ is flow contribution for a specific stage pair, $V_{wellbore}$ is wellbore volume, $\Delta t$ is arrival time difference, and N is a specific stage. For example, as in FIG. 2D, a stage pair includes a first stage that received unique particulate tracer 170$a_{oil}$ and a second stage that received unique particulate tracer 170$e_{oil}$, with three stages are located between the first stage and the second stage without any unique particulate tracers. Thus, the flow contribution may include the stage pair of the first stage and the second stage as well as the three stages in between. FIG. 10 provides more information including the $\Delta t$, which is arrival time difference. With the improved placement and design, the particulate tracer response at the surface could be interpreted like wellbore solid tracers for flow profiling as illustrated in FIG. 10.

The method 900 of FIG. 9 includes step 920 as a check by obtaining a production history for the wellbore; summing all flow contributions for each stage pair for each phase; and comparing the sums and the production history to constraint total flow contribution for each phase. The production history may be obtained as discussed elsewhere herein. This step may be performed as a check.

If there is an inconsistency, then the method 900 may include an optional step 925 to smooth a tracer concentration history for a specific unique particulate tracer before c) of step 915 to reduce noise (e.g., reduce points that show large variations ups and/or downs); and utilize the smoothed tracer concentration history for the specific unique particulate tracer in c) of step 915. This optional step 915 may be performed by curve fitting to smoothen out the data (e.g., normal, log normal, or other representative curve fit).

The method 900 of FIG. 9 includes step 930 to generate, on a graphical user interface, a representation of the flow profile for the wellbore for each phase indicative of the flow contribution for each stage pair and stages within each stage pair; and display, via the graphical user interface, the representation.

Those of ordinary skill in the art will appreciate that various modifications may be made to the description above. For example, the method 900 may include an optional step 935 to refine the wellbore volume in response to multiple phases in the wellbore. Various ways to refine the wellbore volume are provided in FIGS. 11-22. Various other optional steps are also provided in FIGS. 11-22.

Figure 23:
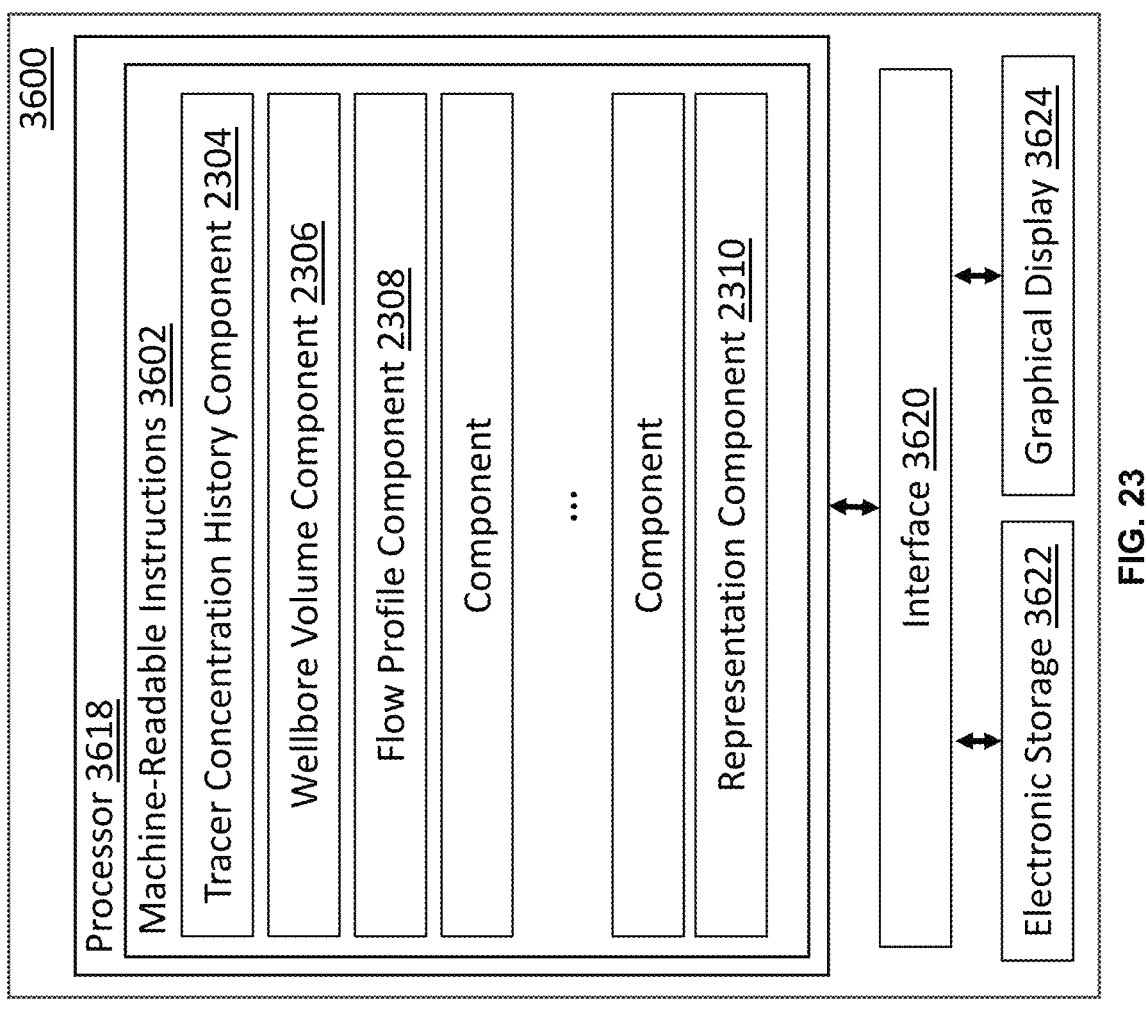
FIG. 23 illustrates an example computer system consistent with the disclosure.

One or more of the steps described hereinabove in the method 900 of FIG. 9 may be implemented by a system and/or in a system, such as a system 3600 shown in FIG. 36 as illustrated in FIG. 23. For example, the step 905 to obtain a tracer concentration history for each unique particulate tracer may be implemented by component 2304 in FIG. 23. The step 910 to determine a wellbore volume for the stage pair may be implemented by component 2306 in FIG. 23. The step 915 to determine a flow profile for the wellbore for each phase indicative of flow contribution for each stage pair and stages in between each stage pair using the wellbore volume and the corresponding tracer concentration histories may be implemented by component 2308 in FIG. 23. A representation of one or more flow profiles may be generated and displayed by component 2310. FIG. 7A-7G include various examples consistent with the disclosure.

Comparison Between Solid Wellbore Tracer vs Concentrated Particulate Tracers: In a typical wellbore with 3 inch id, the surface area per ft for wellbore tracers is 0.8 ft2. If installed over two tubing lengths (60 ft). the exposed surface area is 48 ft2. If the wellbore tracer is installed over a stage of 200 ft in length, the exposed surface area is 160 ft2. 1 gm particulate tracers have exposed surface area of 32000 ft2 and occupies 0.00017 ft3 of the volume. Over a length of 1 ft and ~2000 lbs of proppant loading in the reservoir and random closed packing has a pore volume of ~19 ft3 and bulk volume of ~12 ft3 so a tracer loading of 1 kg of tracer in last 10% of the stage with 1.2 ft3 of near wellbore bulk volume would occupy 0.17 ft3 which would end up providing the exposed surface area of 32*10^6 ft2. The maximum fluid contacted volume in the last 10% of a stage with above specifications would be 1.9 ft3 per ft of a stage. For a stage with the length of 200 ft, the tracer contacted volume could be ~67 bbls with large exposed tracer surface area as calculated. This would allow for a significant tracer concentration spike 6 orders of magnitude higher than the conventional wellbore tracers and should also act similar to wellbore tracers to estimate flowrate across the well using pulse velocity method. The technique would use high frequency sampling like for a deepwater well and equivalent to 24 to 48 hours. These tracers should also last a while but the life span would be smaller 10 times smaller (6 to 12 months, field observation) than the conventional wellbore tracers (upto 5 years). Non-interventional, allows for determining water breakthrough stages, allows for oil/water rate quantification for stages over time, allows for same tracers to be installed in multiple wells nearby because we can focus on the tracer flowback with pulse velocity method.

Determining a Flow Profile for a Wellbore Using Unique Particulate Tracers that are Pumped Throughout Each Stage, Each Stage Group, or any Combination Thereof:

Reference will now be made in detail to various embodiments, examples of which are illustrated in the accompanying drawings. In the following detailed description, numerous specific details are set forth in order to provide a thorough understanding of the present disclosure and the embodiments described herein. However, embodiments described herein may be practiced without these specific details. In other instances, well-known methods, procedures, components, and mechanical apparatus have not been described in detail so as not to unnecessarily obscure aspects of the embodiments.

Example embodiments of determining a flow profile for a wellbore using unique particulate tracers will be described more fully hereinafter with reference to the accompanying drawings. At least one unique particulate tracer is pumped throughout each stage, each stage group, or any combination thereof during a hydraulic fracturing operation performed in the subterranean formation in example embodiments, however, determining a flow profile may be embodied in many different forms and should not be construed as limited to the example embodiments set forth herein. Rather, these embodiments and examples are provided so that this disclosure will be thorough and complete, and will fully convey the scope of determining a flow profile to those of ordinary skill in the art. Like, but not necessarily the same, elements (also sometimes called components) in the various figures are denoted by like reference numerals for consistency.

As explained hereinabove, in the existing practice, as illustrated in FIGS. 1D-1, 1D-2, 1D-3, 1E-1, 1E-2, and 1E-3, quantitative evaluation of stage and/or stage group contribution to flow is not generally possible with the existing manner that unique particulate tracers are placed throughout the entirety of stages and/or stage groups. First, in FIGS. 1E-1, 1E-2, and 1E-3, quantitative evaluation of stage and/or stage group contribution to flow is not generally possible because the unique particulate tracers of wellbore 120 may go to one or both offset wellbores 175. As a result, the unique particulate tracers affecting the flow in the wellbore 120 may not be known and there may not be a good baseline for flow profiling. As another example, tracer recovery curves may simply indicate a binary response of flow vs no-flow. FIG. 1G illustrates a single wellbore with a StageM and a StageN, and FIG. 1H illustrates typical tracer recovery curves indicative of just the binary response of flow vs. no-flow. Second, tracer release rate is not a function of the flowrate, so the quantification is generally not possible with the existing tracer design. Indeed, existing placement of unique particulate tracers have not been able to quantify the flow profile along the lateral during flow so far because tracer release rate for unique particulate tracers is not proportional to the flow rate. For example, the existing practice of placing unique particulate tracers throughout the entirety of stages and/or stage groups make it difficult to quantify the flow profile along the lateral during flow because tracer release rate for particulates is not proportional to the flow rate. Third, if the unique particulate tracers are distributed throughout the injected stage volume, then the produced unique particulate tracer response may be very dispersed so the existing methods (similar to solid wellbore tracer application) for flow profiling called the pulse velocity method or decay method cannot be used. In short, there are current limitations on flow profiling using unique particulate tracers that are placed in the entirety of stages and/or stage groups.

Advantageously, as will be described further herein, embodiments are provided in this disclosure related to determining a flow profile for a wellbore using unique particulate tracers that are pumped throughout each stage, each stage group, or any combination thereof. By doing so, these embodiments may be utilized to provide quantitative flow profiles that were not generally available in the existing practice. Furthermore, provided herein are embodiments of two methods referred to as the "response time delay method" and the "decline method" that may be utilized to determine the flow profiles. The "response time delay method" may be dependent on the release rate, but the "decline method" is not. In some circumstances, both the "response time delay method" and the "decline method" may be utilized for comparison and validation.

Advantageously, embodiments provided herein may be utilized for non-interventional time-based flow profiling using the unique particulate tracers. The determined flow profiles may be utilized for completion design optimization, understanding changes in flow profiles as a function of time, understand rock type proximate to the wellbore, where to drill a wellbore, understand production from different parts of the lateral that can be utilized to optimize wellbore length and/or wellbore landing, understand possible optimization equipment or techniques for increasing hydrocarbon recovery, etc.

Figure 24:
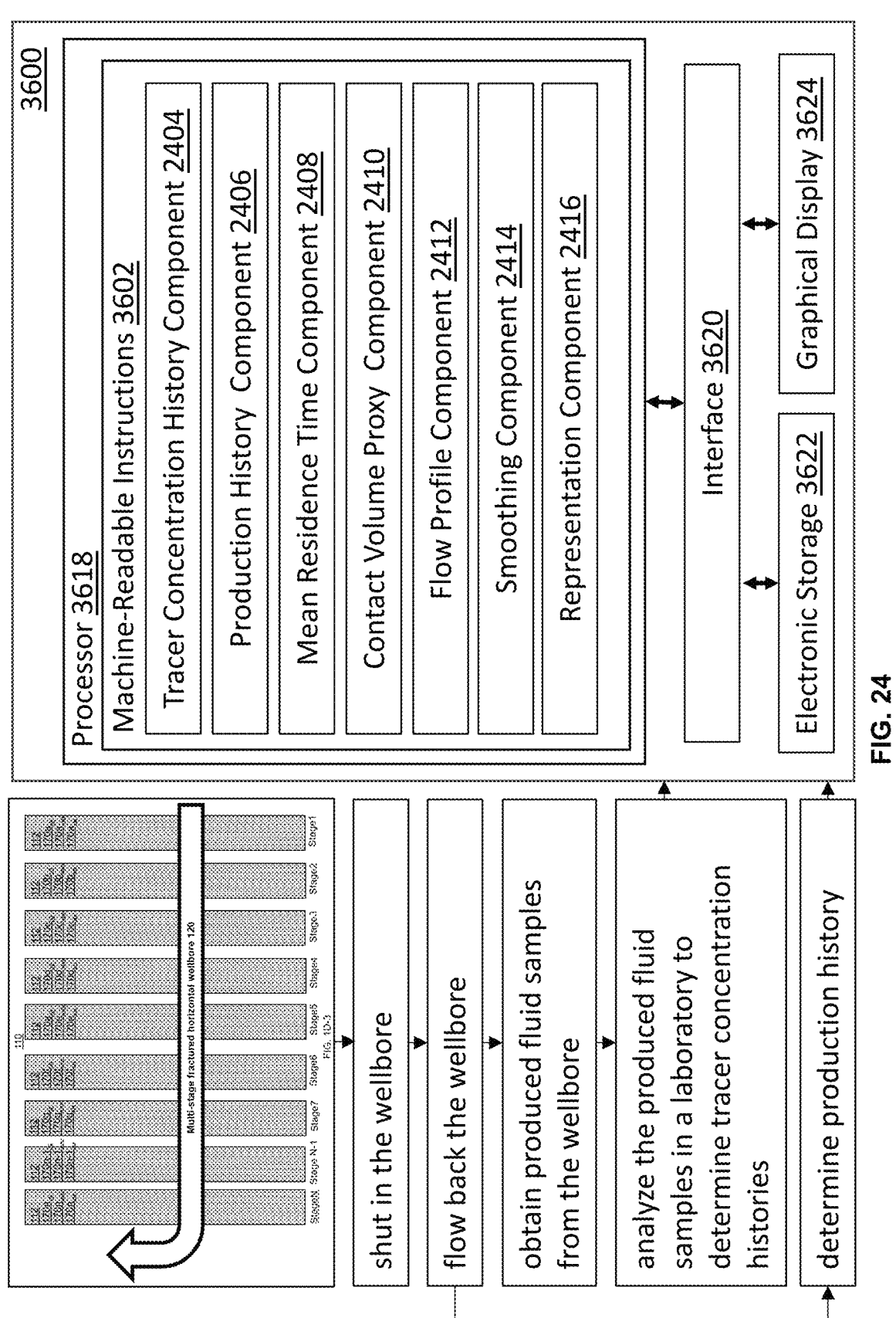
FIG. 24 illustrates an example computer system consistent with the disclosure.
Figure 36:
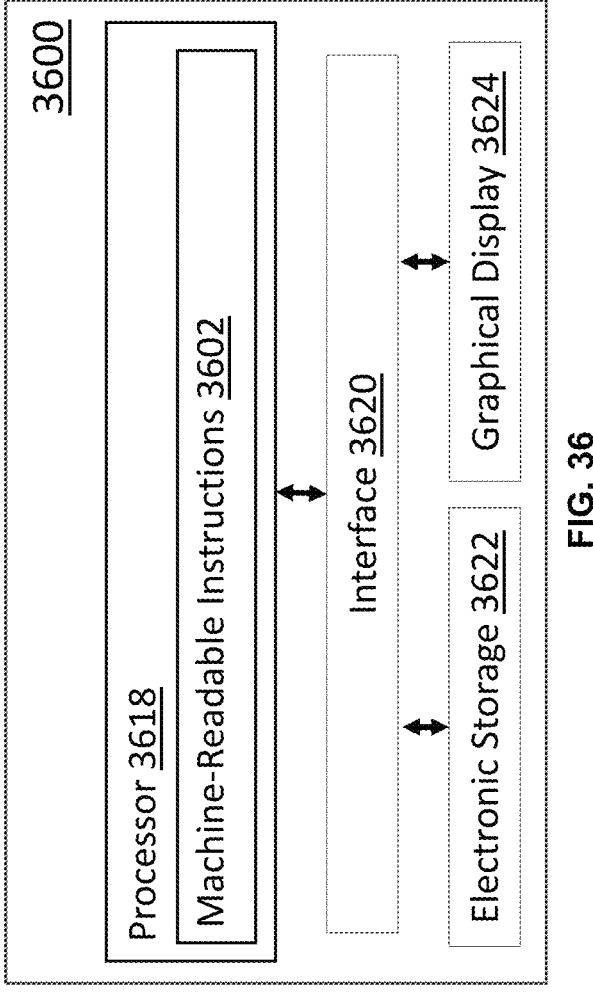
FIG. 36 illustrates an example computer system consistent with the disclosure.

Response Time Delay Method:

The methods and systems of the present disclosure may be implemented by a system and/or in a system, such as a system 3600 shown in FIG. 36 and FIG. 24. A method of determining a flow profile for a wellbore using unique particulate tracers may be performed by the processor 3618, including input such as at least one tracer concentration history (e.g., a tracer concentration history for each unique particulate tracer) and/or a production history for a wellbore as well as output such as a flow profile for the wellbore for each phase indicative of flow contribution of each stage, each stage group, or any combination thereof. The electronic storage 3622 may store information relating to the tracer concentration history for each unique particulate tracer, the production history of the wellbore, information about the produced fluid samples, and/or other information. The graphical display 3624 may present information relating to the flow profile for the wellbore for each phase indicative of the flow contribution of each stage, each stage group, or any combination thereof, and/or other information.

The processor 3618 may be configured to execute one or more machine-readable instructions 3602 to facilitate determining the flow profile for the wellbore for each phase using the unique particulate tracers. The machine-readable instructions 3602 may include one or more computer program components. The machine-readable instructions 3602 may include a tracer concentration history component 2404, a production history component 2406, a mean residence time component 2408, a contact volume proxy component 2410, a flow profile component 2412, a smoothing component 2414, a representation component 2416, and/or other computer program components.

The tracer concentration history component 2404 may be configured to obtain (e.g., from the non-transitory storage medium such as the electronic storage 3622) a tracer concentration history for each unique particulate tracer in produced fluid samples from a wellbore drilled into a subterranean formation. At least one unique particulate tracer was pumped throughout each stage, each stage group, or any combination thereof during a hydraulic fracturing operation performed in the subterranean formation. Each unique particulate tracer corresponds to an oil phase, a water phase, or a gas phase. The produced fluid samples comprise at least a portion of the unique particulate tracers that are pumped throughout the stages, the stage groups, or any combination thereof.

The production history component 2406 may be configured to obtain (e.g., from the non-transitory storage medium such as the electronic storage 3622) a production history for the wellbore.

The mean residence time component 2408 may be configured to determine (e.g., with the physical computer processor such as the processor 3618) a mean residence time for each unique particulate tracer using the corresponding tracer concentration history.

The contact volume proxy component 2410 may be configured to determine (e.g., with the physical computer processor such as the processor 3618) a contact volume proxy for each unique particulate tracer using the production history and the corresponding tracer concentration history.

The flow profile component 2412 may be configured to determine (e.g., with the physical computer processor such as the processor 3618) a flow profile for the wellbore for each phase indicative of flow contribution of each stage, each stage group, or any combination thereof by using the corresponding mean residence times and the corresponding contact volume proxies.

The smoothing component 2414 may be configured to smooth (e.g., with the physical computer processor such as the processor 3618) a tracer concentration history for a specific unique particulate tracer before determining a mean residence time and before determining a contact volume proxy to reduce noise. The smoothed tracer concentration history for the specific unique particulate tracer may be utilized in determining the mean residence time and determining the contact volume proxy.

The representation component 2416 may be configured to generate (e.g., on the graphical user interface such as the graphical display 3624) a representation of the flow profile for the wellbore for each phase indicative of the flow contribution of each stage, each stage group, or any combination thereof. The representation component 2416 may be configured to display (e.g., on the graphical user interface such as the graphical display 3624) the representation.

FIG. 25 illustrates an example method 2500 for determining a flow profile for a wellbore using unique particulate tracers. The method 2500 may be referred to as a response time delay method herein (e.g., Response time delay, rate=volume/time), however, those of ordinary skill in the art will appreciate that this terminology is not meant to be limiting. The method 2500 may be utilized if high frequency data with mode is accurately captured with time (e.g., high frequency sampling depending on the flow rate) and/or low oil rate. For example, the response delay method may be applied when data is collected in the first 5 days post POP (i.e., popping the wellbore open for the first time after the unique particulate tracers were pumped in), such as collecting produced fluid samples at least once a day to about 5+ a day, at least once a day to about 10+ a day, etc.

While the various steps in one embodiment of the method 2500 are presented sequentially, one of ordinary skill will appreciate that some or all of the steps may be executed in different orders, may be combined or omitted, and some or all of the steps may be executed in parallel. Further, in one or more of the example embodiments, one or more of the steps shown in this example method may be omitted, repeated, and/or performed in a different order. Furthermore, a person of ordinary skill in the art will appreciate that any equations utilized herein may be modified without changing the meaning, for example, an equation may be modified to use different units such as metric units without changing the meaning. A person of ordinary skill in the art will appreciate that additional steps not shown in FIG. 25 may be included in performing this method. The method shown in FIG. 25 is merely one embodiment that can be performed by using a system, such as described in FIG. 36 and FIG. 24. FIGS. 1D-3, 24, and 36 are utilized in the discussion of FIG. 25 for ease of understanding.

Referring to FIG. 25, the method 2500 includes step 2505 to obtain (e.g., from the non-transitory storage medium such as the electronic storage 3622) a tracer concentration history for each unique particulate tracer in produced fluid samples from a wellbore drilled into a subterranean formation. At least one unique particulate tracer is pumped throughout each stage, each stage group, or any combination thereof during a hydraulic fracturing operation performed in the subterranean formation. Each unique particulate tracer corresponds to an oil phase, a water phase, or a gas phase. For example, if a flow profile for the oil phase is desired, then unique oil particulate tracers that will react to oil should be pumped throughout the stages. If a flow profile for the water phase is desired, then water unique particulate tracers that will react to water should be pumped throughout the stages. If a flow profile for the gas phase is desired, then gas unique particulate tracers that will react to gas should be pumped throughout the stages. The produced fluid samples comprise at least a portion of the unique particulate tracers that are pumped throughout the stages, the stage groups, or any combination thereof.

The tracer concentration history of a specific unique particulate tracer may include a tracer concentration (e.g., in parts per billion (ppb)) as a function of time for the specific stage that it is pumped into during the hydraulic fracturing operation. The tracer concentration history for each unique particulate tracer that is obtained at the step 2505 may be previously generated using laboratory analysis (discussed in FIG. 27). For example, the produced fluid samples obtained from the produced fluid from the wellbore may be analyzed in a laboratory using equipment and/or tests such as, but not limited to: chromatography. ultra-high-performance liquid chromatography (UHPLC) with a fluorescent light scattering detector and a diode array detector (DAD) may be used to obtain the spectral profile of samples, triple quad mass spec liquid chromatography may be used to integrate target ions and precursor ions of the chemical of interest, or other known techniques to generate a tracer concentration history for each unique particulate tracer. This generated tracer concentration history for each unique particulate tracer may be obtained from a non-transitory storage medium at the step 2505. Two example tracer concentration histories in curve form are illustrated in FIG. 1H. The step 2505 may be performed using the tracer concentration history component 2404.

Turning to the running example, the running example based on FIG. 1D-3 assumes that the wellbore 120 produces oil, water, and gas, and therefore, a unique oil particulate tracer, a unique water particulate tracer, and a unique gas particulate tracer are pumped throughout each stage of the figure (i.e., throughout the nine stages). In other words, a total of twenty-seven unique particulate tracers (i.e., nine unique oil particulate tracers, nine unique water particulate tracers, and nine unique gas particulate tracers) are pumped in FIG. 1D-3 For simplicity, this running example assumes that all twenty-seven unique particulate tracers $170a_{oil}$, $170a_{water}$, $170a_{gas}$, $170b_{oil}$, $170b_{water}$, $170b_{gas}$, $170c_{oil}$, $170c_{water}$, $170c_{gas}$, $170d_{oil}$, $170d_{water}$, $170d_{gas}$, $170e_{oil}$, $170e_{water}$, $170e_{gas}$, $170f_{oil}$, $170f_{water}$, $170f_{gas}$, $170g_{oil}$, $170g_{water}$, $170g_{gas}$, $170n\text{-}1_{oil}$, $170n\text{-}1_{water}$, $170n\text{-}1_{gas}$, $170n_{oil}$, $170n_{water}$, and $170n_{gas}$ were detected by laboratory analysis in the produced fluid samples from the wellbore 120. At step 2505, a tracer concentration history is obtained from a non-transitory storage medium for each of the twenty-seven unique particulate tracers (i.e., twenty-seven tracer concentration histories may be obtained from the non-transitory storage medium).

The method 2500 includes step 2510 to obtain (e.g., from the non-transitory storage medium such as the electronic storage 2422) a production history for the wellbore. The production history accounts for the phases of the produced fluid of the wellbore, including the oil phase, the water phase, the gas phase, or any combination thereof. The production history that is obtained may include quantity (e.g., barrels (bbls) per day) of oil that is produced from the wellbore, quantity (e.g., barrels (bbls) per day) of water that is produced from the wellbore, quantity (e.g., standard cubic feet (scf) per day) of gas that is produced from the wellbore, or any combination thereof. For example, if the wellbore produces all three phases, then the production history accounts for all three phases. However, if the wellbore does not produce gas, for example, then the production history may reflect water, oil, or both water and oil but not gas.

In one embodiment, the production history may include quantity or rate of oil that is produced from the wellbore, quantity or rate of water that is produced from the wellbore, quantity or rate of gas that is produced from the wellbore, or any combination thereof, for example, as a function of time. In one embodiment, the production history may include additional information, such as, but not limited to, wellbore identification information, well geographic properties (e.g., x coordinate for the heel, y coordinate for the heel, depth, and/or azimuth), geologic properties (e.g., identification information for the subterranean formation), wellbore properties (e.g., tortuosity), completion properties (e.g., perforated length, proppant intensity, and/or fracturing fluid intensity), etc. The production history for the wellbore that is obtained from the non-transitory storage medium at the step 2510 may be previously generated using known techniques (discussed in FIG. 27). The step 2510 may be performed using the production history component 2406.

The running example based on FIG. 1D-3 assumes that the wellbore 120 produces oil, water, and gas. At step 2510, a production history may be obtained for the wellbore 120 that includes the quantity or rate of oil that is produced from the wellbore 120, the quantity or rate of water that is produced from the wellbore 120, and the quantity or rate of gas that is produced from the wellbore 120.

Figure 26A:
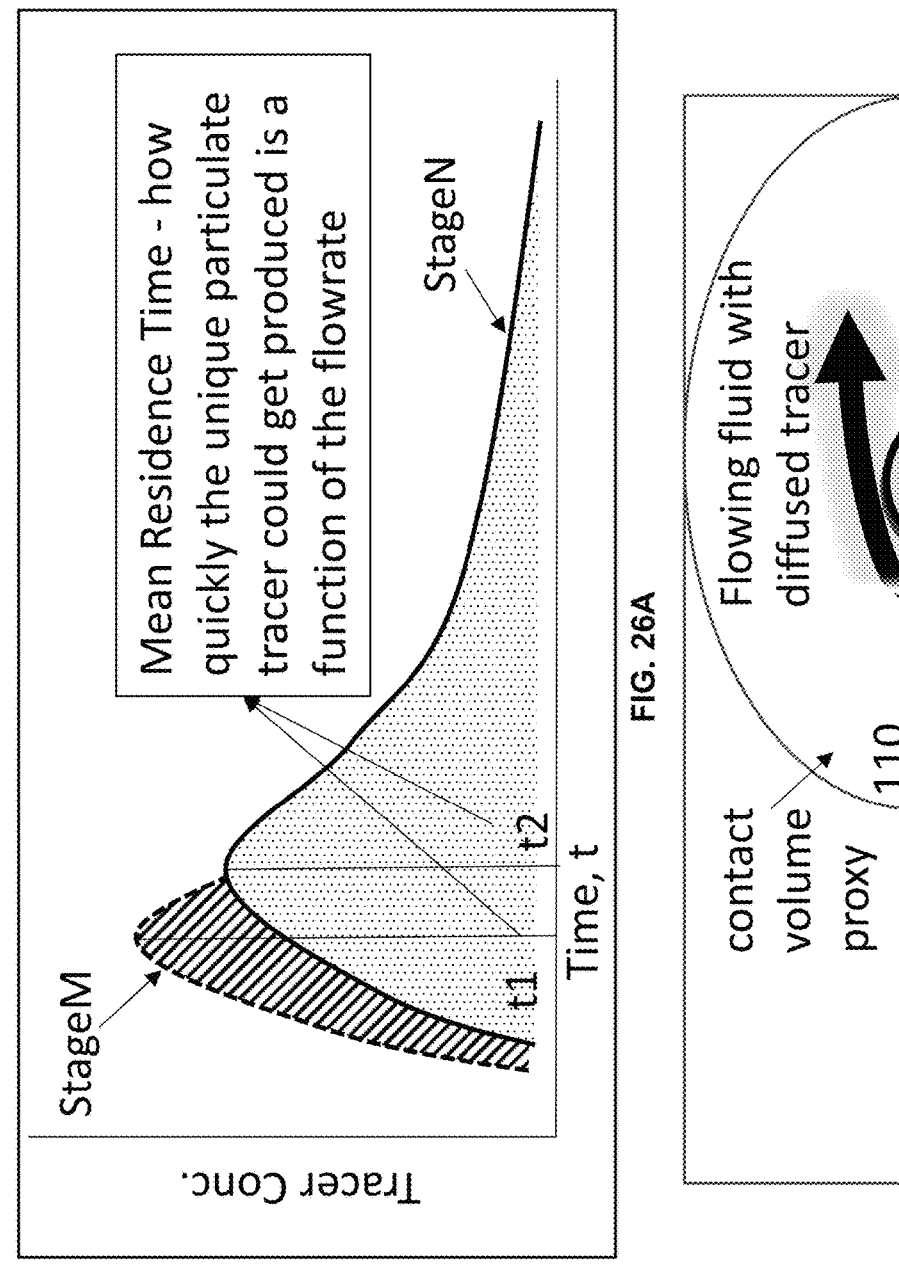
FIG. 26A illustrates one diagram regarding mean residence time.

The method 2500 includes step 2515 to determine (e.g., with a physical computer processor such as the processor 3618) a mean residence time for each unique particulate tracer using the corresponding tracer concentration history. For example, the mean residence time of a specific unique particulate tracer generally refers to how quickly that specific unique particulate tracer gets produced from the stage that it is pumped into. How quickly a unique particulate tracer could get produced is a function of the flowrate, and flowrate is defined as volume over time (e.g., the contact volume proxy discussed hereinbelow over mean residence time). One diagram regarding mean residence time is illustrated in FIG. 26A.

In one embodiment, the mean residence time is determined using an equation as follows:

$$t_{res} = \frac{\int_{t=0}^{t=\infty} c * t * dt}{\int_{t=0}^{t=\infty} c * dt}$$

wherein $t_{res}$ is mean residence time, c is tracer concentration history, t is time, and dt is integration with respect to time. Additionally, t=0 is time starting from zero and t=∞ goes to infinity, thus, the time t can start at zero and go to a desired value up to infinity. The unit for mean residence time may be in hours. The mean residence time can be thought of as a time proxy over which the contact volume proxy discussed hereinbelow gets produced. The mean residence time equation hereinabove may be repeated for each unique particulate tracer using the corresponding tracer concentration history that was obtained. The step 2515 may be performed using the mean residence time component 2408.

In the running example based on FIG. 1D-3, at step 2515, a mean residence time may be determined using the equation above for each of the twenty-seven unique particulate tracers (i.e., twenty-seven mean residence times may be determined).

Figure 26B:
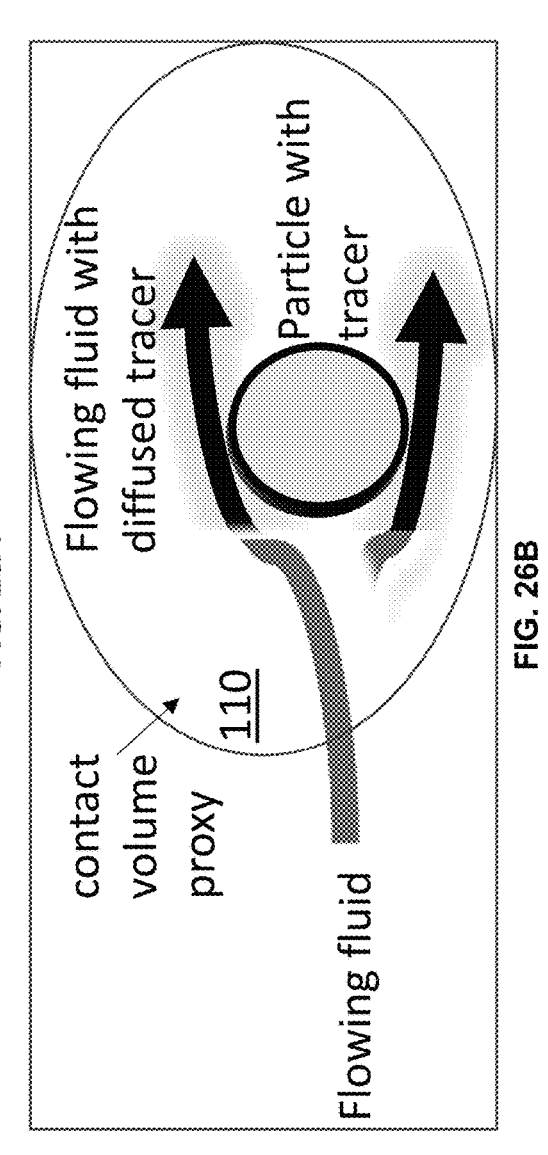
FIG. 26B illustrates one diagram regarding contact volume proxy.

The method 2500 includes step 2520 to determine (e.g., with the physical computer processor such as the processor 3618) a contact volume proxy for each unique particulate tracer using the production history and the corresponding tracer concentration history. For example, the contact volume proxy of a specific unique particulate tracer generally refers to an approximate volume of the subterranean formation that was contacted by the specific unique particulate tracer as it diffused/leached/dissolved in the subterranean formation, or in other words, what is the approximate volume of the subterranean formation contacted by the tracer cloud of the specific unique particulate tracer (discussed in FIG. 27). One diagram regarding contact volume proxy in the subterranean formation 110 is illustrated in FIG. 26B. The proxy for volume through which the tracer cloud flows (i.e., contact volume proxy) is illustrated as the area under the curves in FIG. 26A.

In one embodiment, the contact volume proxy is determined using an equation as follows:

$$vol_{proxy} = \int_{t=0}^{t=\infty} q * c * dt$$

Wherein $vol_{proxy}$ is contact volume proxy, q is production history, c is tracer concentration history, t is time, and dt is integration with respect to time. Additionally, t=0 is time starting from zero and t=∞ goes to infinity, thus, the time t can start at zero and go to a desired value up to infinity. The unit for contact volume proxy may be barrels (bbls). The contact volume proxy equation hereinabove may be repeated for each unique particulate tracer using the production history and the corresponding tracer concentration history that were obtained. The step 2520 may be performed using the contact volume proxy component 2410.

In the running example based on FIG. 1D-3, at step 2520, a contact volume proxy may be determined using the equation above for each of the twenty-seven unique particulate tracers (i.e., twenty-seven contact volume proxies may be determined).

The method 2500 includes step 2525 to determine (e.g., with the physical computer processor such as the processor 3618) a flow profile for the wellbore for each phase indicative of flow contribution of each stage, each stage group, or any combination thereof by using the corresponding mean residence times and the corresponding contact volume proxies. The flow contribution for each stage or stage group is determined, and then, the flow contributions corresponding to a specific phase are included in a flow profile for that specific phase (e.g., a flow profile for the oil phase, a separate flow profile for the water phase, and/or a separate flow profile for the gas phase). Each flow profile provides a quantitative evaluation of each stage or stage group's contribution to flow (e.g., per phase) that is not generally available for unique particulate tracers that are placed throughout the entirety of stages and/or stage groups. Each flow profile provides a quantitative evaluation of each stage and/or stage group's contribution to flow that is an improvement over the simple binary information of existing techniques.

In one embodiment, the flow profile is determined using an equation as follows:

$$\text{flow\_contribution}_N(\%) = \frac{\dfrac{vol_{proxy\_N}}{t_{res\_N}}}{\sum_{i=1}^{i=M} \dfrac{vol_{proxy\_i}}{t_{res\_i}}} * 100$$

wherein flow_contribution$_N$ is flow contribution for a specific stage or specific stage group, $t_{res}$ is mean residence time, $vol_{proxy}$ is contact volume proxy, i is a counter, M is total number of stages or stage groups in which unique particulate tracers are pumped, and N is specific stage or specific stage group for which flow contribution is determined. The flow contribution may be in the form of a percentage. The flow contribution equation hereinabove may be repeated for each stage or stage group using the corresponding mean residence times and the corresponding contact volume proxies that were determined.

A flow profile for a phase may include all the corresponding flow contribution percentages determined with the equation hereinabove. For example, a flow profile for the oil phase includes all the flow contribution percentages determined with the equation hereinabove corresponding to the unique oil particulate tracers, which should sum up to about 100%. A separate flow profile for the water phase includes all the flow contribution percentages determined with the equation hereinabove corresponding to the unique water particulate tracers, which should sum up to about 100%. A separate flow profile for the gas phase includes all the flow contribution percentages determined with the equation hereinabove corresponding to the unique gas particulate tracers, which should sum up to about 100%. A representation of each flow profile for each phase may be generated and displayed using a bar chart, line graph, curves, etc. using conventional techniques as discussed hereinbelow at step 2530. In one embodiment, a representation of a flow profile in terms of cumulative information (e.g., percentage cum oil along the lateral) may be generated and displayed. The step 2525 may be performed using the flow profile component 2412.

In the running example based on FIG. 1D-3, at step 2525, a flow contribution may be determined using the equation above for each of the twenty-seven unique particulate tracers (i.e., twenty-seven flow contributions may be determined). A flow profile for the oil phase, for example, in the form of a bar chart may be made using the nine flow contribution percentages corresponding to the oil phase. A flow profile for the water phase, for example, in the form of a bar chart may be made using the nine flow contribution percentages corresponding to the water phase. A flow profile for the gas phase, for example, in the form of a bar chart may be made using the nine flow contribution percentages corresponding to the gas phase.

The method 2500 includes step 2530 to generate, on a graphical user interface such as the graphical display 3624, a representation of the flow profile for the wellbore for each phase indicative of the flow contribution of each stage, each stage group, or any combination thereof, and display, via the graphical user interface, the representation. Visual effects may be utilized to illustrate flow contribution per stage and/or stage group in the flow profile. A representation of each flow profile for each phase may be generated and displayed using a bar chart, line graph, curves, etc. The representation of each flow profile for each phase may include confidence levels, flow contribution information determined in another manner (e.g., using logging equipment, sensors, or other equipment) for comparison, etc. In one embodiment, a representation of a flow profile in terms of cumulative information (e.g., percentage cum oil along the lateral) may be generated and displayed. Examples of flow profiles for an oil phase are illustrated in FIGS. 33A-33H.

In the running example based on FIG. 1D-3, at step 2530, three representations of flow profiles may be generated and displayed (e.g., a representation of the flow profile for the oil phase in the form of a bar chart using the nine flow contribution percentages corresponding to the oil phase, a representation of the flow profile for the water phase in the form of a bar chart using the nine flow contribution percentages corresponding to the water phase, and a representation of the flow profile for the gas phase in the form of a bar chart using the nine flow contribution percentages corresponding to the gas phase).

Those of ordinary skill in the art will appreciate that various modifications may be made to the description above. As an example, FIG. 1D-3 illustrates individual stages instead of stage groups for simplicity, however, a person of ordinary skill in the art will appreciate that the steps 2505-2530 are also applicable in the context of one or more stage groups. As another example, the method 2500 may include an optional step 2535 to smooth a tracer concentration history for a specific unique particulate tracer before c) of step 2515 and d) of step 2520 to reduce noise (e.g., reduce points that show large variations ups and/or downs); and utilize the smoothed tracer concentration history for the specific unique particulate tracer in c) of step 2515 and d) of step 2520. This optional step 2535 may be performed by curve fitting to smoothen out the data (e.g., normal, log normal, or other representative curve fit). As another example, a person of ordinary skill in the art will appreciate that a single phase like the oil phase may be of interest so unique oil particulate tracers only may be pumped throughout the stages and/or stage groups (or two phases may be of interest and those corresponding unique particulate tracers may be pumped throughout the stages and/or stage groups). Thus, the method 2500 applies to one phase, two phases, or three phases. As another example, the method 2500 may be used for laterals, vertical wellbores, etc.

FIG. 27 illustrates an example method 2700 for determining a flow profile for a wellbore using unique particulate tracers. The method 2700 of FIG. 27 may include at least one of the steps of the method 2500 of FIG. 25. The method 2700 may also be referred to as a response time delay method herein (e.g., Response time delay, rate=volume/time), however, those of ordinary skill in the art will appreciate that this terminology is not meant to be limiting. The method 2700 may be utilized if high frequency data with mode is accurately captured with time (e.g., high frequency sampling depending on the flow rate) and/or low oil rate. For example, the response delay method may be applied when data is collected in the first 5 days after POP (i.e., popping the wellbore open after shut-in period), such as collecting produced fluid samples at least once a day to about 5+a day, at least once a day to about 10+a day, etc. The discussion of method 2700 of FIG. 27 will focus on physical steps that may be performed at the wellbore, in the field, and/or at a laboratory before the method 2500 of FIG. 25, as generally illustrated in FIG. 24.

While the various steps in one embodiment of the method 2700 are presented sequentially, one of ordinary skill will appreciate that some or all of the steps may be executed in different orders, may be combined or omitted, and some or all of the steps may be executed in parallel. Further, in one or more of the example embodiments, one or more of the steps shown in this example method may be omitted, repeated, and/or performed in a different order. Furthermore, a person of ordinary skill in the art will appreciate that any equations utilized herein may be modified without changing the meaning, for example, an equation may be modified to use different units such as metric units without changing the meaning. A person of ordinary skill in the art will appreciate that additional steps not shown in FIG. 27 may be included in performing this method. The method shown in FIG. 27 is merely one embodiment that can be performed by using a system, such as described in FIG. 36 and FIG. 24. FIGS. 1D-3, 24, and 36 are utilized in the discussion of FIG. 27 for ease of understanding.

Referring to FIG. 27, the method 2700 includes step 2705 to pump at least one unique particulate tracer throughout each stage, each stage group, or any combination thereof during a hydraulic fracturing operation performed in the subterranean formation, such as in FIG. 1D-3. Each unique particulate tracer corresponds to an oil phase, a water phase, or a gas phase. For example, the unique particulate tracers may be blended with proppant (e.g., sand) (e.g., the proppant 112) and pumped throughout stages, stage groups, or any combination thereof. As another example, the unique particulate tracers may be directly injected into the fracturing fluid stream and pumped throughout stages, stage groups, or any combination thereof. Practically any pumping equipment or pumping technique known in the art for pumping unique particulate tracers throughout stages, stage groups, or any combination thereof may be utilized.

In the running example based on FIG. 1D-3, at step 2705, the proppant 112 and the twenty-seven unique particulate tracers $170a_{oil}$, $170a_{water}$, $170a_{gas}$, $170b_{oil}$, $170b_{water}$, $170b_{gas}$, $170c_{oil}$, $170c_{water}$, $170c_{gas}$, $170d_{oil}$, $170d_{water}$, $170d_{gas}$, $170e_{oil}$, $170e_{water}$, $170e_{gas}$, $170f_{oil}$, $170f_{water}$, $170f_{gas}$, $170g_{oil}$, $170g_{water}$, $170g_{gas}$, $170n\text{-}1_{oil}$, $170n\text{-}1_{water}$, $170n\text{-}1_{gas}$, $170n_{oil}$, $170n_{water}$, and $170n_{gas}$ are pumped into the nine stages as illustrated in FIG. 24.

Figures 28A, 28B:
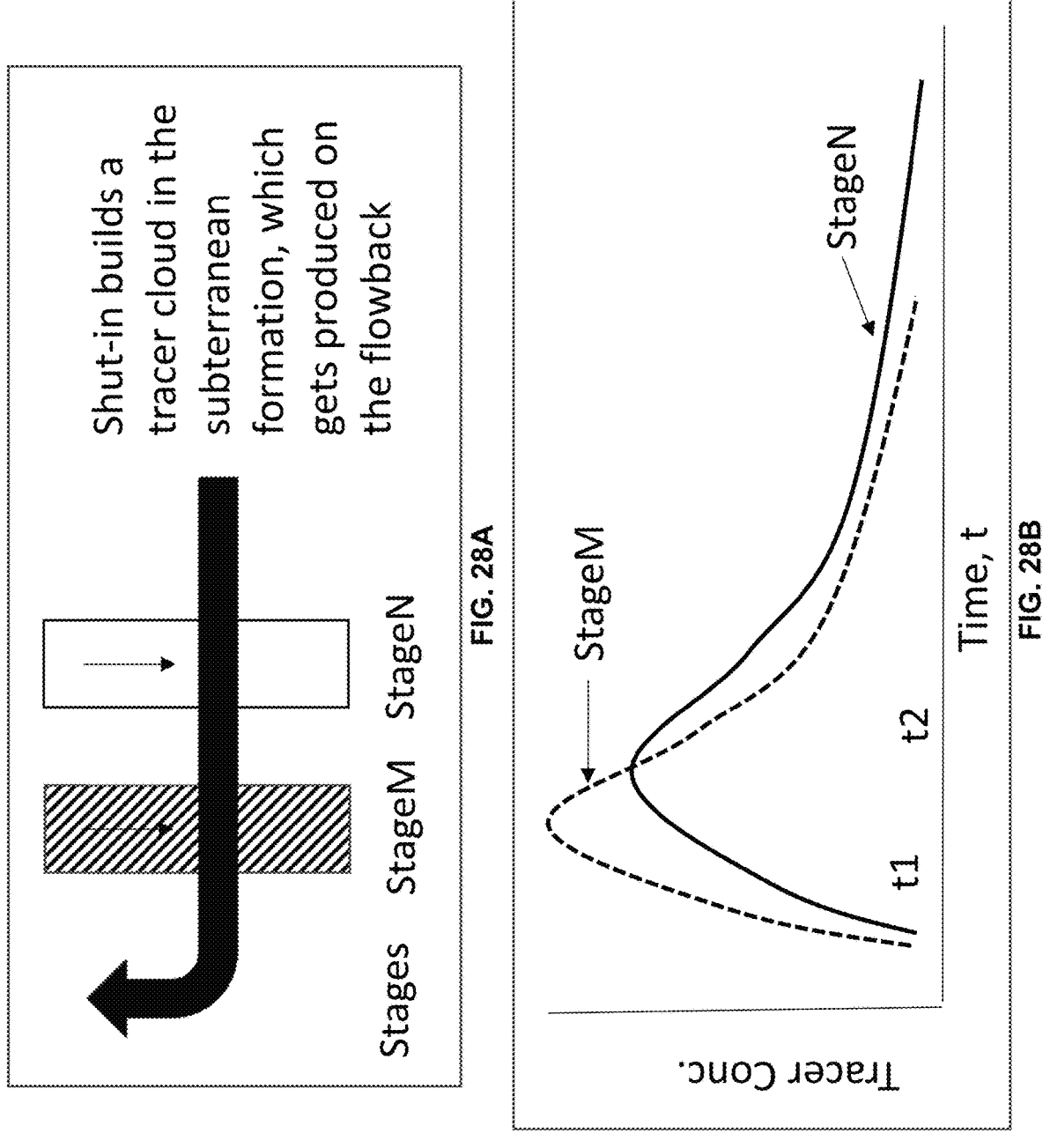
FIG. 28A-28B illustrate an example of shut-in to build up tracer clouds.

The method 2700 includes step 2710 to shut-in the wellbore for a period of time to cause tracer clouds to form in the subterranean formation for at least a portion of the unique particulate tracers that are pumped throughout the stages, the stage groups, or any combination thereof. Shutting in of the wellbore may help build the tracer cloud for each unique particulate tracer pumped as it diffuses/leaches/dissolves in the subterranean formation. The wellbore is shut-in for a period of time that is long enough for the injected unique particulate tracers to be detected in the produced fluid samples. The wellbore may be shut-in for a period of time such as 1 day to 3 days (i.e., 24 hours to 72 hours). The longer the wellbore has been producing, then the longer the shut-in period in some embodiments, such as a shut-in period of upto 5 days (i.e., upto 120 hours). The period of time for the shut-in may depend on the unique particulate tracers pumped, logistics and practical realities associated with shutting in a wellbore, etc. The wellbore may be shut-in using known techniques for shutting in wellbores. In short, the step 2710 shut-in the wellbore for enough time for tracer clouds to be developed so detectable tracer concentrations are produced. FIGS. 28A-28B illustrate an example of shut-in to build up tracer clouds.

In the running example based on FIG. 1D-3, at step 2710, the wellbore 120 is shut-in for a period of time long enough for tracer clouds to be developed for the twenty-seven unique particulate tracers $170a_{oil}$, $170a_{water}$, $170a_{gas}$, $170b_{oil}$, $170b_{water}$, $170b_{gas}$, $170c_{oil}$, $170c_{water}$, $170c_{gas}$, $170d_{oil}$, $170d_{water}$, $170d_{gas}$, $170e_{oil}$, $170e_{water}$, $170e_{gas}$, $170f_{oil}$, $170f_{water}$, $170f_{gas}$, $170g_{oil}$, $170g_{water}$, $170g_{gas}$, $170n$-$1_{oil}$, $170n$-$1_{water}$, $170n$-$1_{gas}$, $170n_{oil}$, $170n_{water}$, and $170n_{gas}$ so detectable tracer concentrations are produced from the wellbore 120 as illustrated in FIG. 24. For example, the wellbore 120 may be shut-in long enough to develop the twenty-seven tracer clouds for the twenty-seven unique particulate tracers.

The method 2700 includes step 2715 to flow back the wellbore to cause produced fluid from the wellbore after the shut-in period. For example, the wellbore flows back up for the time in which the tracer clouds are produced back (e.g., typically 5 to 7 days). The produced fluid samples comprise at least a portion of the unique particulate tracers that are pumped throughout the stages, the stage groups, or any combination thereof.

In the running example based on FIG. 1D-3, at step 2715, the wellbore 120 is flowed back to cause produced fluid to exit the wellbore 120.

The method 2700 includes step 2720 to obtain produced fluid samples comprising unique particulate tracers from a wellbore drilled into a subterranean formation. One embodiment may include sampling frequently for the first few days (~5 days and a function of flow rate) until the tracer clouds get produced. The samples from the produced fluid may be obtained directly from a wellhead that is fluidly coupled to the wellbore using practically any technique and/or equipment known in the art for sampling produced fluid. Information about an automated tracer sampling and measurement system may be found in U.S. Patent Publication Application No. 2014/0260694, which is incorporated by reference.

In the running example based on FIG. 1D-3, at step 2720, produced fluid samples may be collected from the wellbore 120, such as from the wellhead of the wellbore 120. The produced fluid samples comprise at least a portion of the twenty-seven unique particulate tracers that are pumped throughout the nine stages. For example, produced fluid samples may be collected at least once a day to about 5+ a day, at least once a day to about 10+ a day, etc. for approximately five days.

The method 2700 includes step 2725 to analyze the produced fluid samples obtained from the produced fluid to generate the tracer concentration history for each unique particulate tracer. For example, the produced fluid samples obtained from the produced fluid from the wellbore may be analyzed in a laboratory using equipment and/or tests such as, but not limited to: chromatography, ultra-high-performance liquid chromatography (UHPLC) with a fluorescent light scattering detector and a diode array detector (DAD) may be used to obtain the spectral profile of samples, triple quad mass spec liquid chromatography may be used to integrate target ions and precursor ions of the chemical of interest, or other known techniques to generate a tracer concentration history for each unique particulate tracer. The generated tracer concentration histories may be provided to the system 3600 (e.g., one or more remote computing devices of the laboratory may be communicatively coupled to the system 3600 via a wired or wireless connection). The generated tracer concentration history for each unique particulate tracer may be obtained from a non-transitory storage medium at the step 2505 and used to determine a flow profile for each phase as described hereinabove in connection with FIGS. 24, 25, and 36.

In the running example based on FIG. 1D-3, at step 2725, twenty-seven tracer concentration histories may be generated in the laboratory and used to determine a flow profile for each phase.

The method 2700 includes step 2730 to determine the production history of the wellbore. Practically any technique and/or equipment (e.g., downhole and/or on the surface) such as flow meters, temperature sensors, pressure pressures, separators (e.g., using a test separator in the field for about 24 hours), etc. may be utilized to generate the production history. The production history may be determined in the field using this equipment. Information about generating a production history is provided at the following: Izgec, B., Hasan, A. R. R., Lin, D, and C. S. S. Kabir. "Flow-Rate Estimation From Wellhead-Pressure and Temperature Data." SPE Prod & Oper 25 (2010): 31-39, which is incorporated by reference. The generated production history of the wellbore may be provided to the system 3600 (e.g., one or more remote meters, remote sensors, or computing devices may be communicatively coupled to the system 3600 via a wired or wireless connection). The generated production history for the wellbore may be obtained from a non-transitory storage medium at the step 2510 and used to determine a flow profile for each phase as described hereinabove in connection with FIGS. 24, 25, and 36.

In the running example based on FIG. 1D-3, at step 2730, a production history may be generated for the wellbore 120 and used to determine a flow profile for each phase.

The method 2700 includes a step of determining a flow profile for the wellbore for each phase using the produced fluid samples comprising the unique particulate tracers by: a) obtaining a tracer concentration history for each unique particulate tracer; b) obtaining a production history for the wellbore; c) determining a mean residence time for each unique particulate tracer using the corresponding tracer concentration history; d) determining a contact volume proxy for each unique particulate tracer using the production history and the corresponding tracer concentration history; and e) determining the flow profile for the wellbore for each phase indicative of flow contribution of each stage, each stage group, or any combination thereof by using the corresponding mean residence times and the corresponding contact volume proxies. In one embodiment, the step may be performed as explained hereinabove in connection with FIGS. 24, 25, and 36. However, the step 2735 may be performed in other ways in some embodiments. In one embodiment, one or more of the steps of the method 2700 may be implemented using a computing system such as in FIG. 36.

Figure 29:
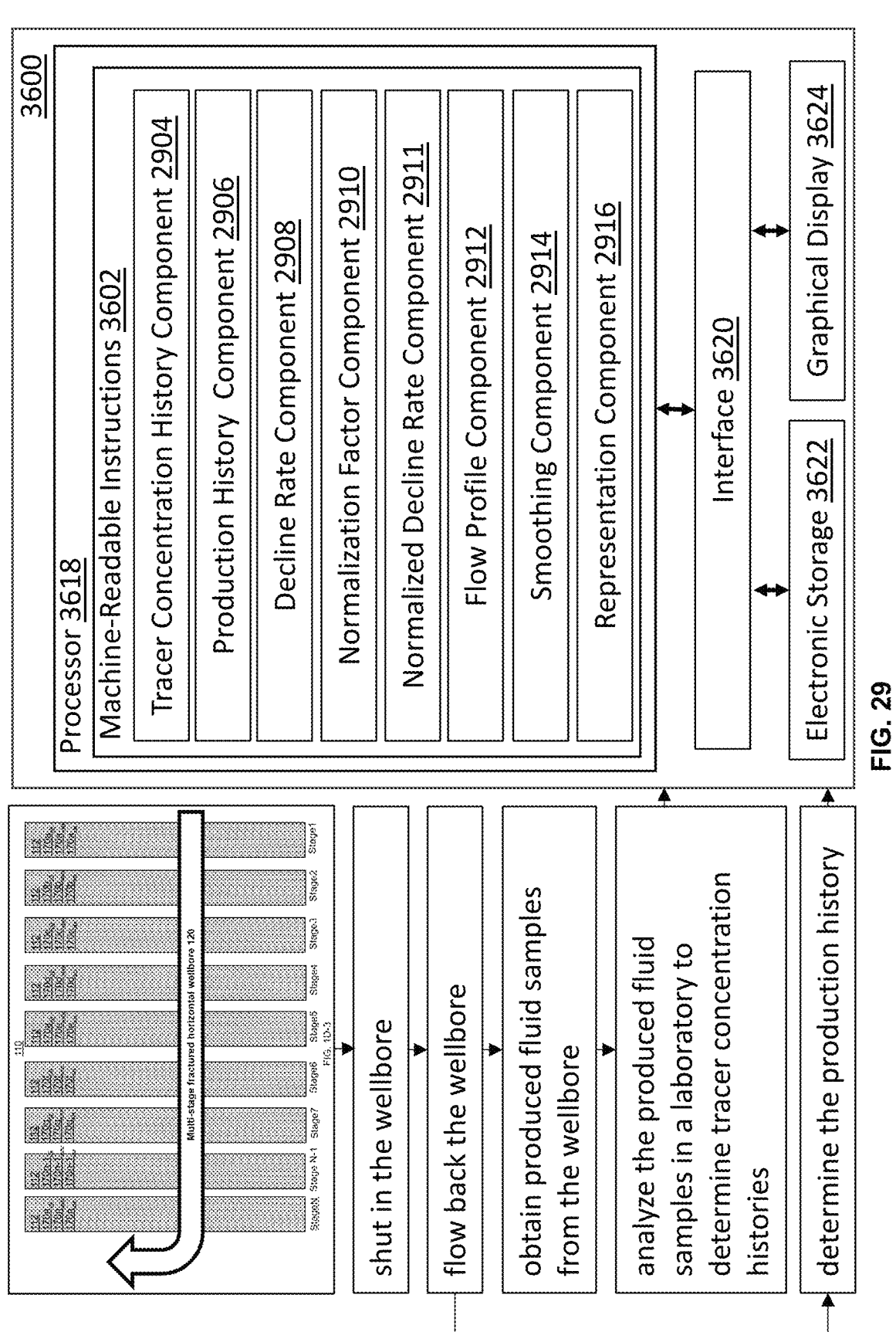
FIG. 29 illustrates an example computer system consistent with the disclosure.

Decline Method:

The methods and systems of the present disclosure may be implemented by a system and/or in a system, such as a system 3600 shown in FIG. 36 and FIG. 29. A method of determining a flow profile for a wellbore using unique particulate tracers may be performed by the processor 3618, including input such as at least one tracer concentration history (e.g., a tracer concentration history for each unique particulate tracer) and/or optionally a production history for a wellbore as well as output such as a flow profile for the wellbore for each phase indicative of flow contribution of each stage, each stage group, or any combination thereof. The electronic storage 3622 may store information relating to the tracer concentration history for each unique particulate tracer, optionally the production history of the wellbore, information about the produced fluid samples, and/or other information. The graphical display 3624 may present information relating to the flow profile for the wellbore for each phase indicative of the flow contribution of each stage, each stage group, or any combination thereof, and/or other information.

The processor 3618 may be configured to execute one or more machine-readable instructions 3602 to facilitate determining the flow profile for the wellbore for each phase using the particulate tracers. The machine-readable instructions 3602 may include one or more computer program components. The machine-readable instructions 3602 may include a tracer concentration history component 2904, optionally a production history component 2906, a decline rate component 2908, a normalization factor component 2910, a normalized decline rate component 2911, a flow profile component 2912, a smoothing component 2914, a representation component 2916, and/or other computer program components.

The tracer concentration history component 2904 may be configured to obtain (e.g., from the non-transitory storage medium such as the electronic storage 3622) a tracer concentration history for each unique particulate tracer in produced fluid samples from a wellbore drilled into a subterranean formation. At least one unique particulate tracer is pumped throughout each stage, each stage group, or any combination thereof during a hydraulic fracturing operation performed in the subterranean formation. Each unique particulate tracer corresponds to an oil phase, a water phase, or a gas phase. The produced fluid samples comprise at least a portion of the unique particulate tracers that are pumped throughout the stages, the stage groups, or any combination thereof.

The optional production history component 2906 may be configured to obtain (e.g., from the non-transitory storage medium such as the electronic storage 3622) a production history for the wellbore.

The decline rate component 2908 may be configured to determine (e.g., with the physical computer processor such as the processor 3618) a decline rate for each unique particulate tracer using the corresponding tracer concentration history.

The normalization factor component 2910 may be configured to determine (e.g., with the physical computer processor such as the processor 3618) a normalization factor for each unique particulate tracer using the corresponding tracer concentration history and optionally the production history.

The normalized decline rate component 2911 may be configured to determine (e.g., with the physical computer processor such as the processor 3618) a normalized decline rate for each unique particulate tracer using the corresponding decline rate and the corresponding normalization factor.

The flow profile component 2912 may be configured to determine (e.g., with the physical computer processor such as the processor 3618) a flow profile for the wellbore for each phase indicative of flow contribution of each stage, each stage group, or any combination thereof by using the corresponding normalized decline rates.

The smoothing component 2914 may be configured to smooth (e.g., with the physical computer processor such as the processor 3618) a tracer concentration history for a specific unique particulate tracer before determining a decline rate and before determining a normalization factor to reduce noise. The smoothed tracer concentration history for the specific unique particulate tracer may be utilized in determining the decline rate and determining the normalization factor.

The representation component 2916 may be configured to generate (e.g., on the graphical user interface such as the graphical display 3624) a representation of the flow profile for the wellbore for each phase indicative of the flow contribution of each stage, each stage group, or any combination thereof. The representation component 2916 may be configured to display (e.g., on the graphical user interface such as the graphical display 3624) the representation.

FIG. 30 illustrates an example method 3000 for determining a flow profile for a wellbore using unique particulate tracers. The method 3000 may be referred to as a decline method herein, however, those of ordinary skill in the art will appreciate that this terminology is not meant to be limiting. The method 3000 may be utilized to determine a flow profile for a wellbore per phase during producing life if high frequency data is not available and/or high oil rate (e.g., a high oil rate may be about 1,000 bbls a day). The method 3000 may be utilized to determine a flow profile for a wellbore per phase if tracer leach rate (diffusion) is not known.

While the various steps in one embodiment of the method 3000 are presented sequentially, one of ordinary skill will appreciate that some or all of the steps may be executed in different orders, may be combined or omitted, and some or all of the steps may be executed in parallel. Further, in one or more of the example embodiments, one or more of the steps shown in this example method may be omitted, repeated, and/or performed in a different order. Furthermore, a person of ordinary skill in the art will appreciate that any equations utilized herein may be modified without changing the meaning, for example, an equation may be modified to use different units such as metric units without changing the meaning. A person of ordinary skill in the art will appreciate that additional steps not shown in FIG. 30 may be included in performing this method. The method shown in FIG. 30 is merely one embodiment that can be performed by using a system, such as described in FIG. 36 and FIG. 29. FIGS. 1D-3, 29, and 36 are utilized in the discussion of FIG. 30 for ease of understanding.

Referring to FIG. 30, the method 3000 includes step 3005 to obtain (e.g., from the non-transitory storage medium such as the electronic storage 3622) a tracer concentration history for each unique particulate tracer in produced fluid samples from a wellbore drilled into a subterranean formation. At least one unique particulate tracer is pumped throughout each stage, each stage group, or any combination thereof during a hydraulic fracturing operation performed in the subterranean formation. Each unique particulate tracer corresponds to an oil phase, a water phase, or a gas phase. For example, if a flow profile for the oil phase is desired, then unique oil particulate tracers that will react to oil should be pumped throughout the stages. If a flow profile for the water phase is desired, then water unique particulate tracers that will react to water should be pumped throughout the stages. If a flow profile for the gas phase is desired, then gas unique particulate tracers that will react to gas should be pumped throughout the stages. The produced fluid samples comprise at least a portion of the unique particulate tracers that are pumped throughout the stages, the stage groups, or any combination thereof.

The tracer concentration history of a specific unique particulate tracer may include a tracer concentration (e.g., in parts per billion (ppb)) as a function of time for the specific stage that it is pumped into during the hydraulic fracturing operation. The tracer concentration history for each unique particulate tracer that is obtained at the step 3005 may be previously generated using laboratory analysis (discussed in FIG. 27). For example, the produced fluid samples obtained from the produced fluid from the wellbore may be analyzed in a laboratory using equipment and/or tests such as, but not limited to: chromatography. ultra-high-performance liquid chromatography (UHPLC) with a fluorescent light scattering detector and a diode array detector (DAD) may be used to obtain the spectral profile of samples, triple quad mass spec liquid chromatography may be used to integrate target ions and precursor ions of the chemical of interest, or other known techniques to generate a tracer concentration history for each unique particulate tracer. This generated tracer concentration history for each unique particulate tracer may be obtained from a non-transitory storage medium at the step 3005. Two example tracer concentration histories in curve form are illustrated in FIG. 1H. The step 3005 may be performed using the tracer concentration history component 2904.

Turning to the running example, the running example based on FIG. 1D-3 assumes that the wellbore 120 produces oil, water, and gas, and therefore, a unique oil particulate tracer, a unique water particulate tracer, and a unique gas particulate tracer are pumped throughout each stage of the figure (i.e., throughout the nine stages). In other words, a total of twenty-seven unique particulate tracers (i.e., nine unique oil particulate tracers, nine unique water particulate tracers, and nine unique gas particulate tracers) are pumped in FIG. 1D-3 For simplicity, this running example assumes that all twenty-seven unique particulate tracers $170a_{oil}$, $170a_{water}$, $170a_{gas}$, $170b_{oil}$, $170b_{water}$, $170b_{gas}$, $170c_{oil}$, $170c_{water}$, $170c_{gas}$, $170d_{oil}$, $170d_{water}$, $170d_{gas}$, $170e_{oil}$, $170e_{water}$, $170e_{gas}$, $170f_{oil}$, $170f_{water}$, $170f_{gas}$, $170g_{oil}$, $170g_{water}$, $170g_{gas}$, $170n\text{-}1_{oil}$, $170n\text{-}1_{water}$, $170n\text{-}1_{gas}$, $170n_{oil}$, $170n_{water}$, and $170n_{gas}$ were detected by laboratory analysis in the produced fluid samples from the wellbore 120. At step 3005, a tracer concentration history is obtained from a non-transitory storage medium for each of the twenty-seven unique particulate tracers (i.e., twenty-seven tracer concentration histories may be obtained from the non-transitory storage medium).

The method 3000 includes optional step 3010 to obtain (e.g., from the non-transitory storage medium such as the electronic storage 3622) a production history for the wellbore. The production history accounts for the phases of the produced fluid of the wellbore, including the oil phase, the water phase, the gas phase, or any combination thereof. The production history that is obtained may include quantity (e.g., barrels (bbls) per day) of oil that is produced from the wellbore, quantity (e.g., barrels (bbls) per day) of water that is produced from the wellbore, quantity (e.g., standard cubic feet (scf) per day) of gas that is produced from the wellbore, or any combination thereof. For example, if the wellbore produces all three phases, then the production history accounts for all three phases. However, if the wellbore does not produce gas, for example, then the production history may reflect water, oil, or both water and oil but not gas.

In one embodiment, the production history may include quantity or rate of oil that is produced from the wellbore, quantity or rate of water that is produced from the wellbore, quantity or rate of gas that is produced from the wellbore, or any combination thereof, for example, as a function of time. In one embodiment, the production history may include additional information, such as, but not limited to, wellbore identification information, well geographic properties (e.g., x coordinate for the heel, y coordinate for the heel, depth, and/or azimuth), geologic properties (e.g., identification information for the subterranean formation), wellbore properties (e.g., tortuosity), completion properties (e.g., perforated length, proppant intensity, and/or fracturing fluid intensity), etc. The production history for the wellbore that is obtained from the non-transitory storage medium at the step 3010 may be previously generated using known techniques (discussed in FIG. 27). The step 3010 may be performed using the production history component 2906.

The running example based on FIG. 1D-3 assumes that the wellbore 120 produces oil, water, and gas. At step 3010, a production history may be obtained for the wellbore 120 that includes the quantity or rate of oil that is produced from the wellbore 120, the quantity or rate of water that is produced from the wellbore 120, and the quantity or rate of gas that is produced from the wellbore 120.

Figures 31A, 31B:
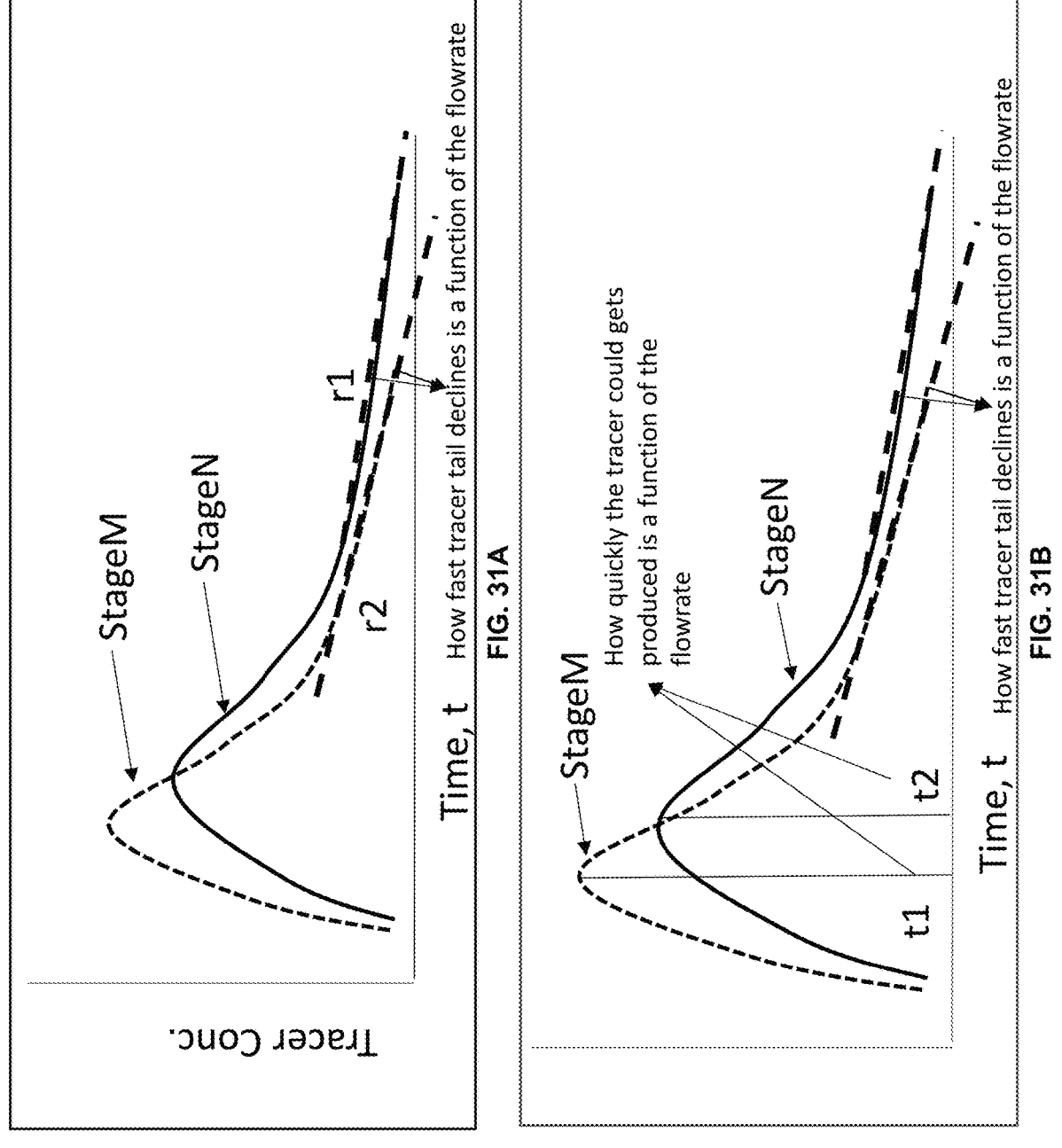
FIG. 31A-31B illustrate two diagrams regarding decline rate.

The method 3000 includes step 3015 to determine (e.g., with a physical computer processor such as the processor 3618) a decline rate for each unique particulate tracer using the corresponding tracer concentration history. For example, flow rate from the stages and/or stage groups is a function of how quickly the tail of a tracer concentration history curve declines from a stage and/or stage group. The faster the decline, the higher the flow rate because the tracer cloud would be produced quicker and vice versa. Two diagrams regarding decline rate are illustrated in FIGS. 31A-31B.

In one embodiment, the decline rate is determined using an equation as follows:

$$r = \frac{dc}{dt}$$

wherein r is decline rate, dC is integration with respect to tracer concentration history, and dt is integration with respect to time. The decline rate is the slope of a tail for a tracer concentration history curve as shown in the plot to the right as r1 and r2 in FIG. 31B. The unit for decline rate may be in parts per billion (ppb) per day. The tail of a specific tracer concentration history is where the slope becomes substantially constant (and stops changing). The decline rate equation hereinabove may be repeated for each unique particulate tracer using the corresponding tracer concentration history that was obtained. The step 3015 may be performed using the mean residence time component 2908.

In the running example based on FIG. 1D-3, at step 3015, a decline rate may be determined using the equation above for each of the twenty-seven unique particulate tracers (i.e., twenty-seven decline rates may be determined).

The method 3000 includes step 3020 to determine (e.g., with the physical computer processor such as the processor 3618) a normalization factor for each unique particulate tracer using the corresponding tracer concentration history and optionally the production history. Each tracer cloud has a different amount of particulate tracer in it so the method 3000 normalizes the concentration so that the decline rates define the flow rate properly. A normalization factor may be utilized for the normalization, and the normalization factor may be determined in two ways. Normalizing with the maximum/peak value of the concentration or the area under the curve are appropriate normalization factors.

In one embodiment, a first normalization factor is represented as:

$$norm_{factor} = c_{mode}$$

wherein norm_factor is normalization factor and $c_{mode}$ is a maximum value of a tracer concentration history (e.g., maximum value of a tracer concentration history curve). The unit for normalization factor may be in parts per billion (ppb). The normalization factor equation hereinabove may be repeated for each unique particulate tracer using the corresponding tracer concentration history that were obtained. The step 3020 may be performed using the normalization factor component 2910.

In one embodiment, a second normalization factor is determined using an equation as follows:

$$norm_{factor} = \int_{t=0}^{t=\infty} q * \rho * c * dt$$

wherein norm_factor is normalization factor, t is time, q is production history, $\rho$ is fluid density (e.g., in pounds per feet), c is tracer concentration history, and dt is integration with respect to time. Additionally, t=0 is time starting from zero and t=∞ goes to infinity, thus, the time t can start at zero and go to a desired value up to infinity. The unit for the normalization factor may be in pounds. The normalization factor equation hereinabove may be repeated for each unique particulate tracer using the corresponding tracer concentration history and the production history that were obtained. The step 3020 may be performed using the normalization factor component 2910.

In the running example based on FIG. 1D-3, at step 3020, a normalization factor may be determined using one of the equations above for each of the twenty-seven unique particulate tracers (i.e., twenty-seven normalization factors may be determined).

The method 3000 includes step 3025 to determine (e.g., with the physical computer processor such as the processor 3618) a normalized decline rate for each unique particulate tracer using the corresponding decline rate and the corresponding normalization factor. In one embodiment, the normalized decline rate is determined using an equation as follows:

$$r\_norm = \frac{r}{norm\_factor}$$

wherein r_norm is normalized decline rate, r is decline rate, and norm_factor is normalization factor. The unit for normalized decline rate may be in 1/pound if the second normalization factor is utilized. The normalized decline rate hereinabove may be repeated for each unique particulate tracer using the corresponding decline rate and the corresponding normalization factor that were obtained. The step 3025 may be performed using the normalized decline rate component 2911.

In the running example based on FIG. 1D-3, at step 3025, a normalized decline rate may be determined using the equation above for each of the twenty-seven unique particulate tracers (i.e., twenty-seven normalized decline rates may be determined).

The method 3000 includes step 3030 to determine (e.g., with the physical computer processor such as the processor 3618) a flow profile for the wellbore for each phase indicative of flow contribution of each stage, each stage group, or any combination thereof by using the corresponding normalized decline rates. The flow contribution for each stage or stage group is determined, and then, the flow contributions corresponding to a specific phase are included in a flow profile for that specific phase (e.g., a flow profile for the oil phase, a separate flow profile for the water phase, and/or a separate flow profile for the gas phase). Each flow profile provides a quantitative evaluation of each stage or stage group's contribution to flow (e.g., per phase) that is not generally available for unique particulate tracers that are placed throughout the entirety of stages and/or stage groups. Each flow profile provides a quantitative evaluation of each stage and/or stage group's contribution to flow that is an improvement over the simple binary information of existing techniques.

In one embodiment, the flow profile is determined using an equation as follows:

$$flow\_contribution_N(\%) = \frac{r_{norm\_N}}{\sum_{i=1}^{i=M} r_{norm\_i}} * 100$$

wherein flow_contribution$_N$ is flow contribution for a specific stage or specific stage group, $r_{norm}$ is normalized decline rate, i is a counter, M is total number of stages or stage groups in which unique particulate tracers are pumped, and N is specific stage or specific stage group for which flow contribution is determined. The flow contribution may be in the form of a percentage. The flow contribution equation hereinabove may be repeated for each stage or stage group using the corresponding normalized decline rates that were determined.

A flow profile for a phase may include all the corresponding flow contribution percentages determined with the equation hereinabove. For example, a flow profile for the oil phase includes all the flow contribution percentages determined with the equation hereinabove corresponding to the unique oil particulate tracers, which should sum up to about 100%. A separate flow profile for the water phase includes all the flow contribution percentages determined with the equation hereinabove corresponding to the unique water particulate tracers, which should sum up to about 100%. A separate flow profile for the gas phase includes all the flow contribution percentages determined with the equation hereinabove corresponding to the unique gas particulate tracers, which should sum up to about 100%. A representation of each flow profile for each phase may be generated and displayed using a bar chart, line graph, curves, etc. using conventional techniques as discussed hereinbelow at step 3030. In one embodiment, a representation of a flow profile in terms of cumulative information (e.g., percentage cum oil along the lateral) may be generated and displayed. The step 3030 may be performed using the flow profile component 2912.

In the running example based on FIG. 1D-3, at step 3030, a flow contribution may be determined using the equation above for each of the twenty-seven unique particulate tracers (i.e., twenty-seven flow contributions may be determined). A flow profile for the oil phase, for example, in the form of a bar chart may be made using the nine flow contribution percentages corresponding to the oil phase. A flow profile for the water phase, for example, in the form of a bar chart may be made using the nine flow contribution percentages corresponding to the water phase. A flow profile for the gas phase, for example, in the form of a bar chart may be made using the nine flow contribution percentages corresponding to the gas phase.

The method 3000 includes step 3035 to generate, on a graphical user interface such as the graphical display 3624, a representation of the flow profile for the wellbore for each phase indicative of the flow contribution of each stage, each stage group, or any combination thereof, and display, via the graphical user interface, the representation. Visual effects may be utilized to illustrate flow contribution per stage and/or stage group in the flow profile. A representation of each flow profile for each phase may be generated and displayed using a bar chart, line graph, curves, etc. The representation of each flow profile for each phase may include confidence levels, flow contribution information determined in another manner (e.g., using logging equipment, sensors, or other equipment) for comparison, etc. In one embodiment, a representation of a flow profile in terms of cumulative information (e.g., percentage cum oil along the lateral) may be generated and displayed. Examples of flow profiles for an oil phase are illustrated in FIGS. 33A-33H.

In the running example based on FIG. 1D-3, at step 3035, three representations of flow profiles may be generated and displayed (e.g., a representation of the flow profile for the oil phase in the form of a bar chart using the nine flow contribution percentages corresponding to the oil phase, a representation of the flow profile for the water phase in the form of a bar chart using the nine flow contribution percentages corresponding to the water phase, and a representation of the flow profile for the gas phase in the form of a bar chart using the nine flow contribution percentages corresponding to the gas phase).

Those of ordinary skill in the art will appreciate that various modifications may be made to the description above. As an example, FIG. 1D-3 illustrates individual stages instead of stage groups for simplicity, however, a person of ordinary skill in the art will appreciate that the steps 3005-3035 are also applicable in the context of one or more stage groups. As another example, the method 3000 may include an optional step 3040 to smooth a tracer concentration history for a specific unique particulate tracer before c) of step 3015 and d) of step 3020 to reduce noise (e.g., reduce points that show large variations ups and/or downs); and utilize the smoothed tracer concentration history for the specific unique particulate tracer in c) of step 3015 and d) of step 3020. For example, the optional step 3040 may smoothen out a tail of the tracer concentration history for a specific unique particulate tracer. This optional step 3040 may be performed by curve fitting to smoothen out the data (e.g., linear regression or other representative curve fit). As another example, a person of ordinary skill in the art will appreciate that a single phase like the oil phase may be of interest so unique oil particulate tracers only may be pumped throughout the stages and/or stage groups (or two phases may be of interest and those corresponding unique particulate tracers may be pumped throughout the stages and/or stage groups). Thus, the method 2500 applies to one phase, two phases, or three phases. As another example, the method 3000 may be used for laterals, vertical wellbores, etc.

Figure 32:
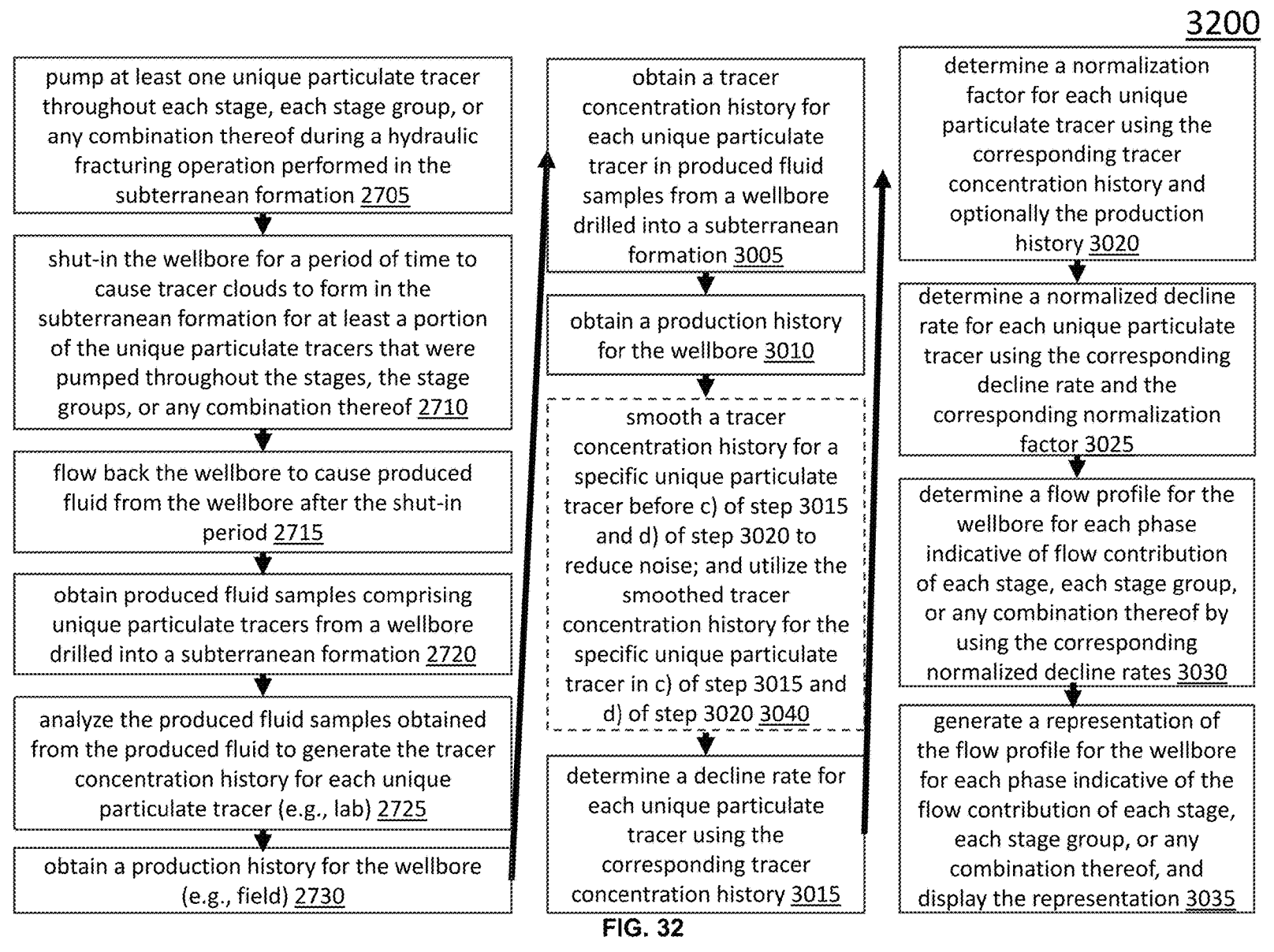

FIG. 32 illustrates an example method 3200 for determining a flow profile for a wellbore using unique particulate tracers. The method 3200 of FIG. 32 may include at least one of the steps of the method 3000 of FIG. 30. The method 3200 of FIG. 32 may include at least one of the steps of the method 2700 of FIG. 27 and FIG. 29. The method 3200 may also be referred to as a decline method herein, however, those of ordinary skill in the art will appreciate that this terminology is not meant to be limiting. The method 3200 may be utilized to determine a flow profile for a wellbore per phase during producing life if high frequency data is not available and/or high oil rate (e.g., a high oil rate may be about 1,000 bbls a day). The method 3200 may be utilized to determine a flow profile for a wellbore per phase if tracer leach rate (diffusion) is not known.

While the various steps in one embodiment of the method 3200 are presented sequentially, one of ordinary skill will appreciate that some or all of the steps may be executed in different orders, may be combined or omitted, and some or all of the steps may be executed in parallel. Further, in one or more of the example embodiments, one or more of the steps shown in this example method may be omitted, repeated, and/or performed in a different order. Furthermore, a person of ordinary skill in the art will appreciate that any equations utilized herein may be modified without changing the meaning, for example, an equation may be modified to use different units such as metric units without changing the meaning. A person of ordinary skill in the art will appreciate that additional steps not shown in FIG. 32 may be included in performing this method. The method shown in FIG. 32 is merely one embodiment that can be performed by using a system, such as described in FIG. 36 and FIG. 29. In one embodiment, one or more of the steps of the method 3200 may be implemented using a computing system such as in FIG. 36.

Figures 33A, 33B:
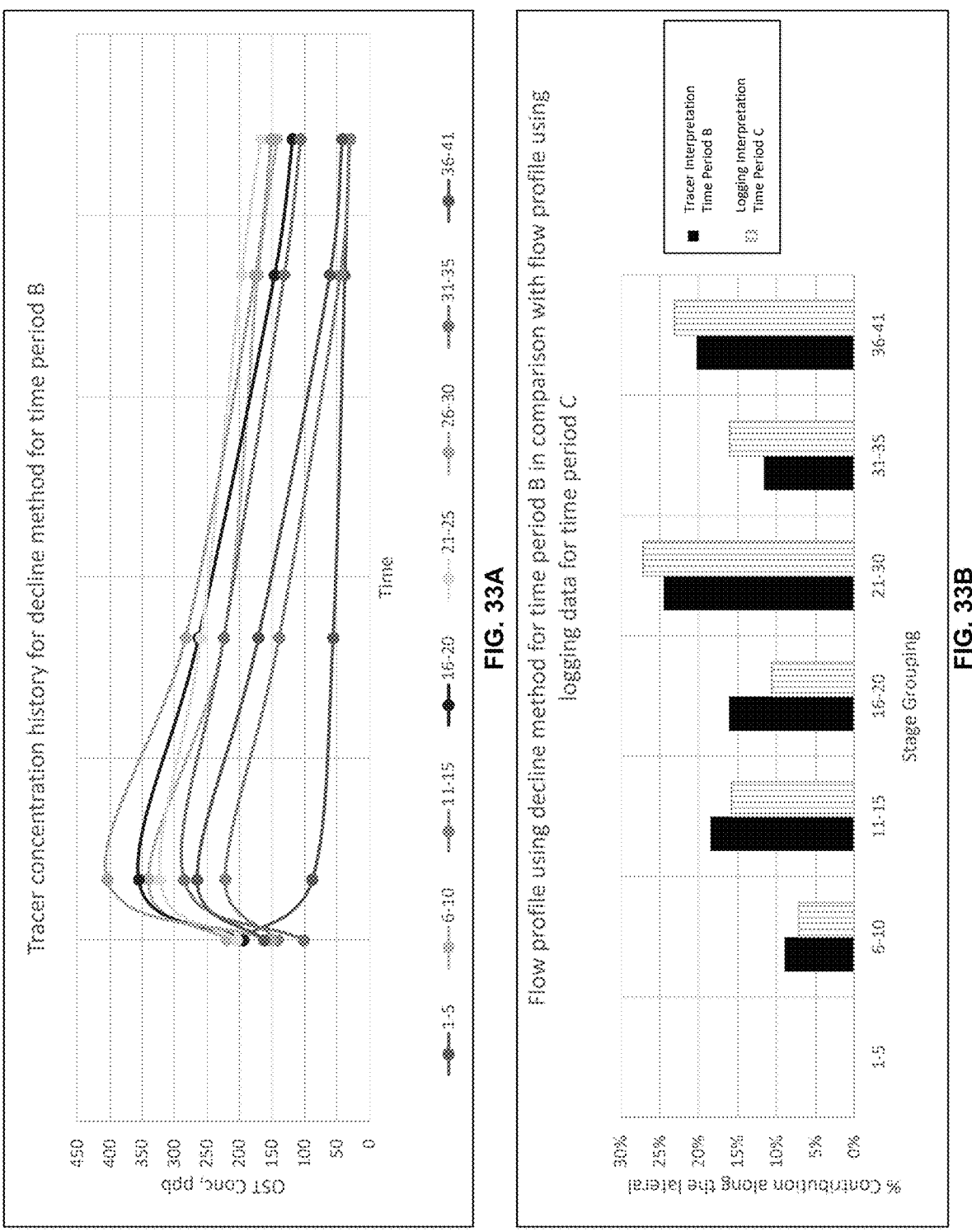
FIG. 33A-33H illustrate various examples of flow profiles for an oil phase only and corresponding tracer concentrations histories for the examples.
Figure 33C:
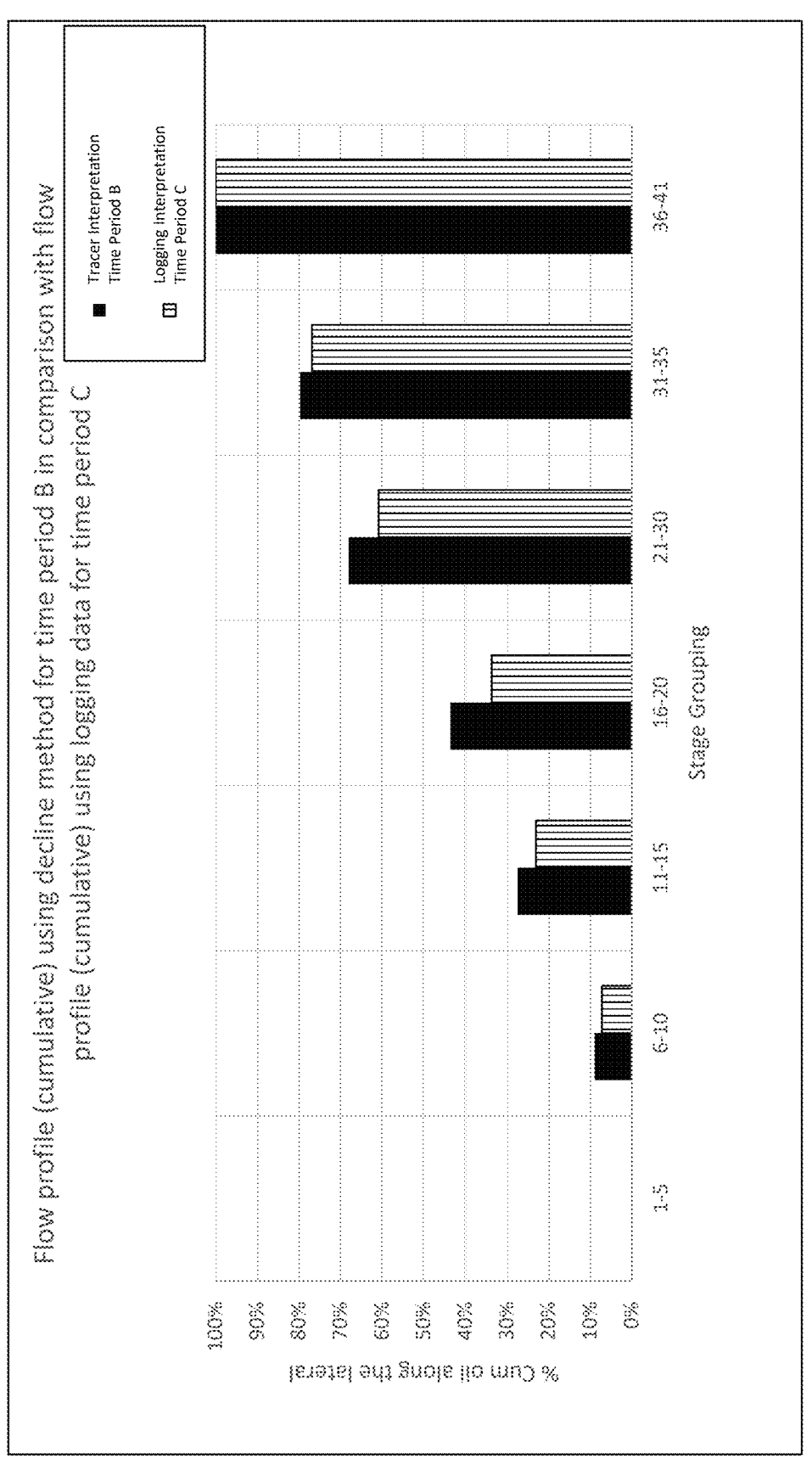
Figure 33D:
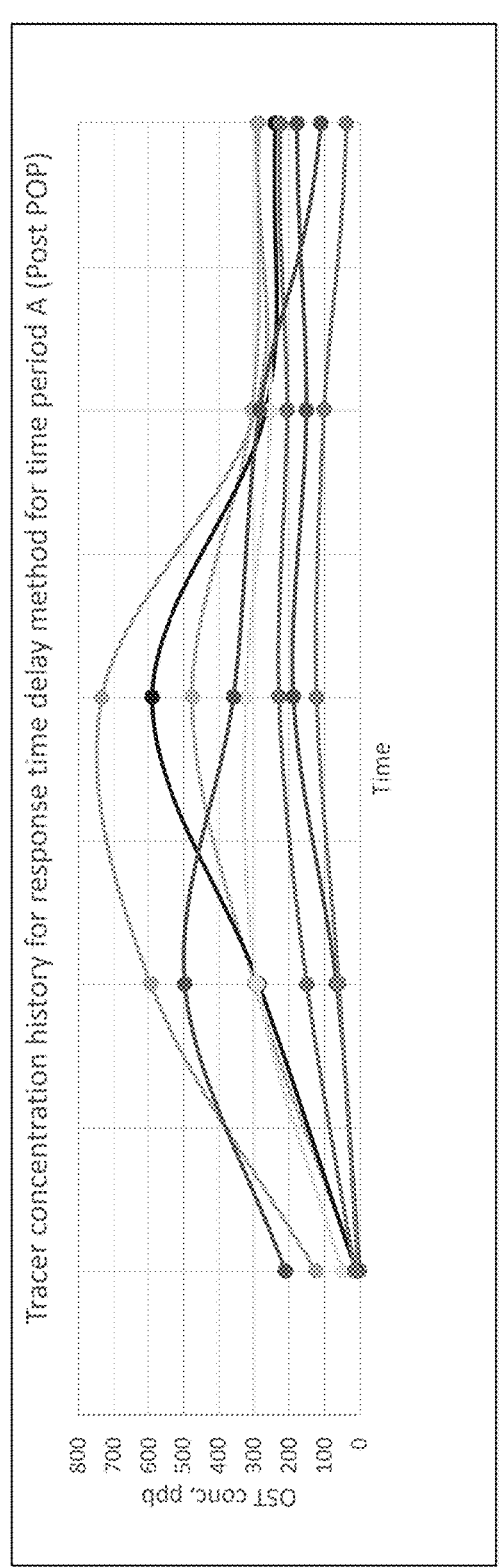
Figure 33E:
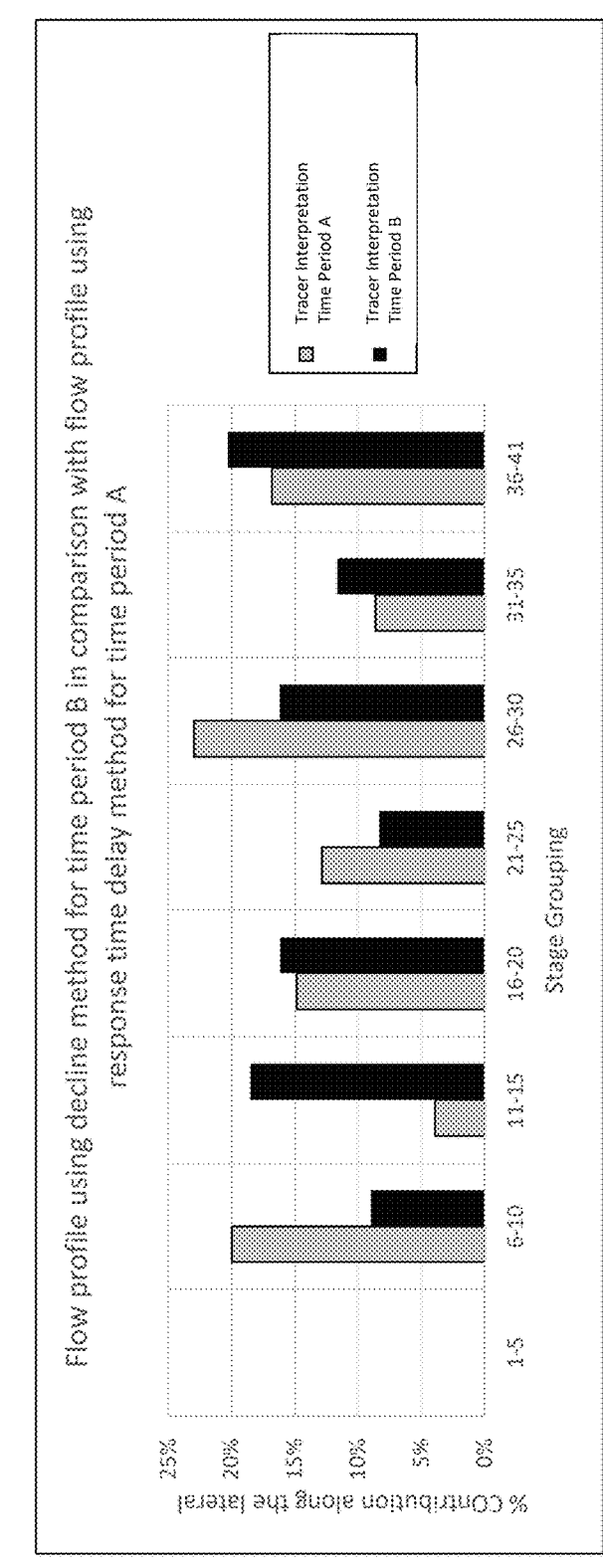
Figure 33F:
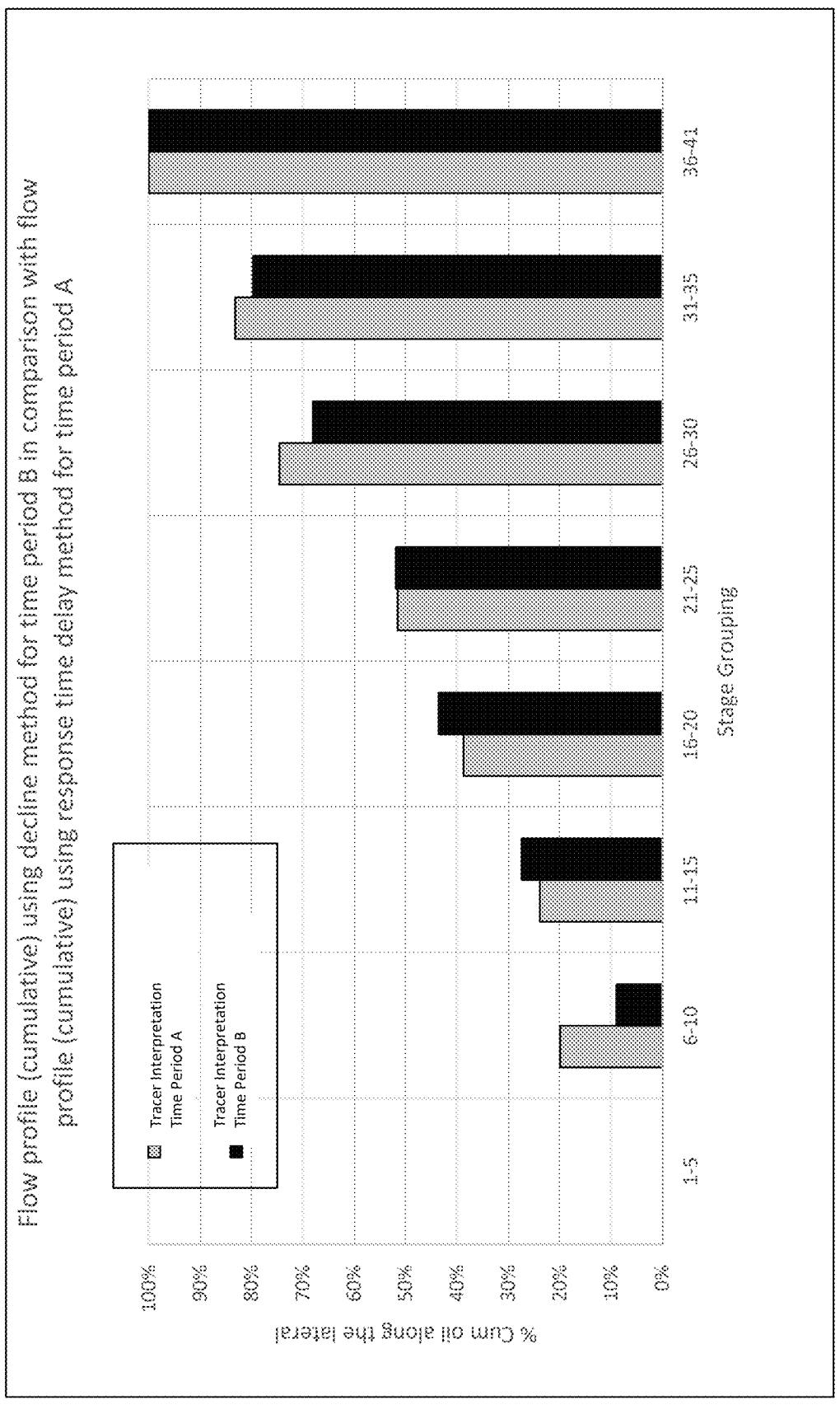
Figures 33G, 33H:
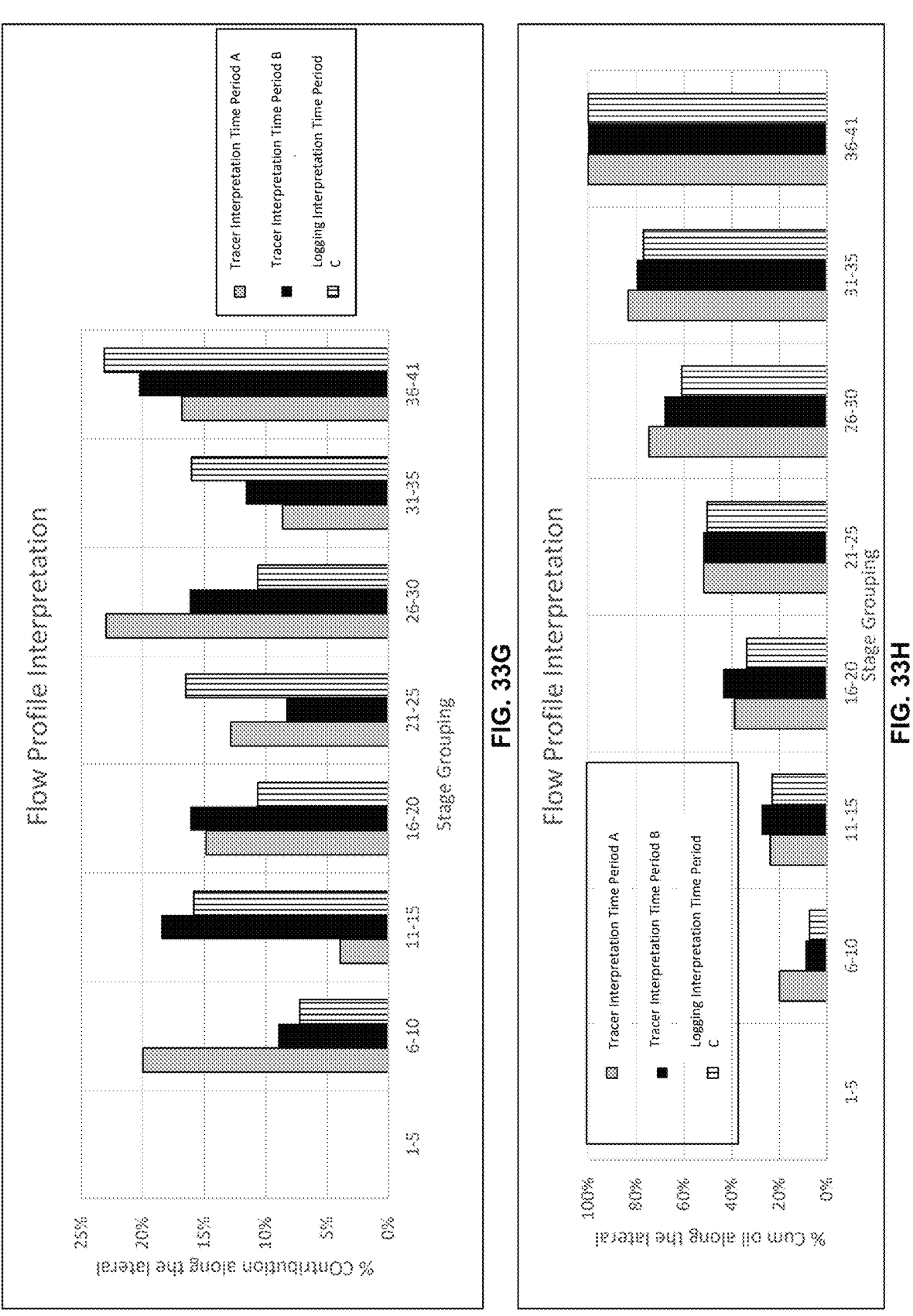
Figures 34A, 34B, 34C:
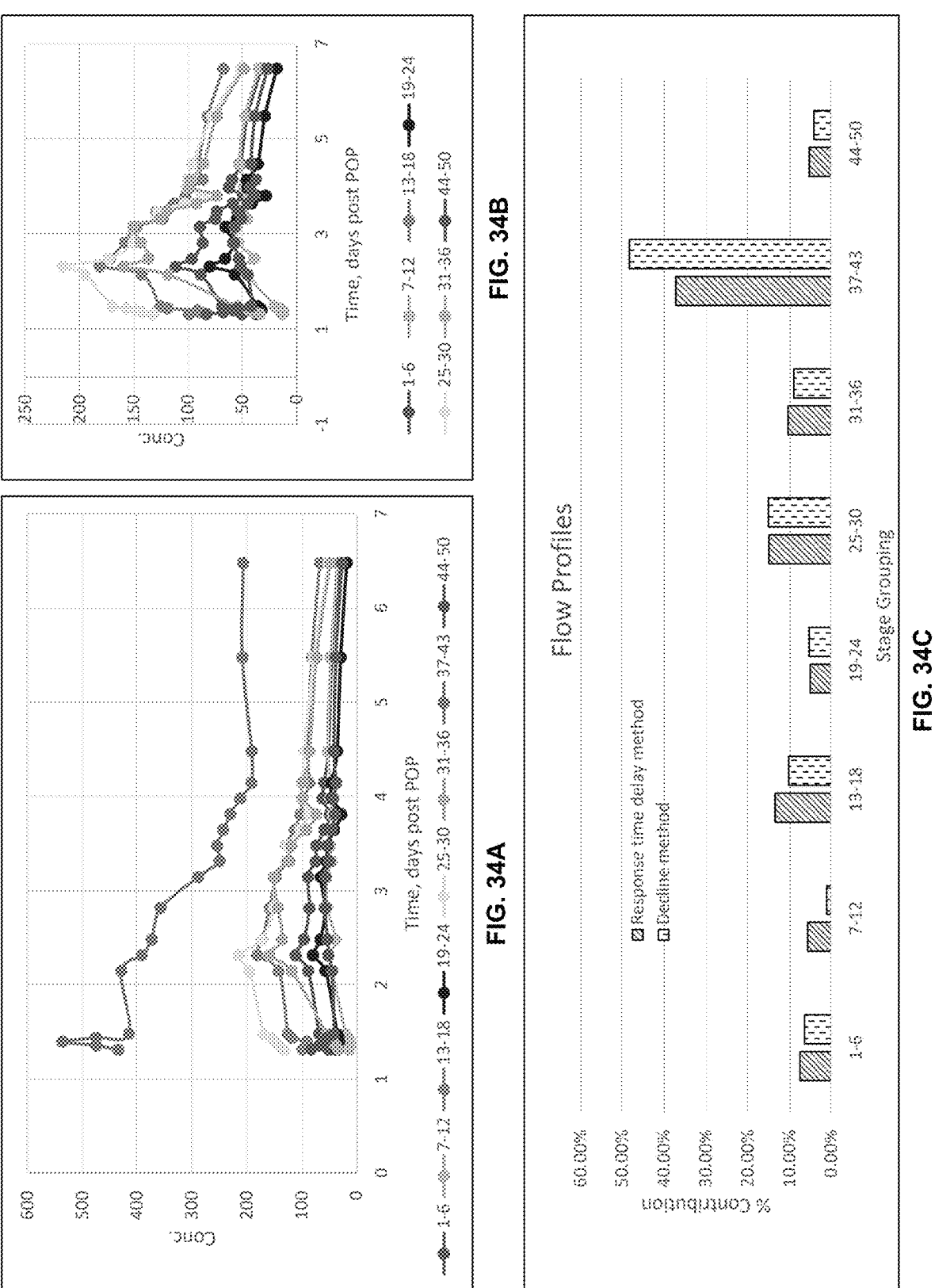
FIGS. 34A-34B and 35A also illustrate tracer concentration histories used with the response time delay method and the decline method as in FIGS. 34C and 35B, respectively.
Figure 35A:
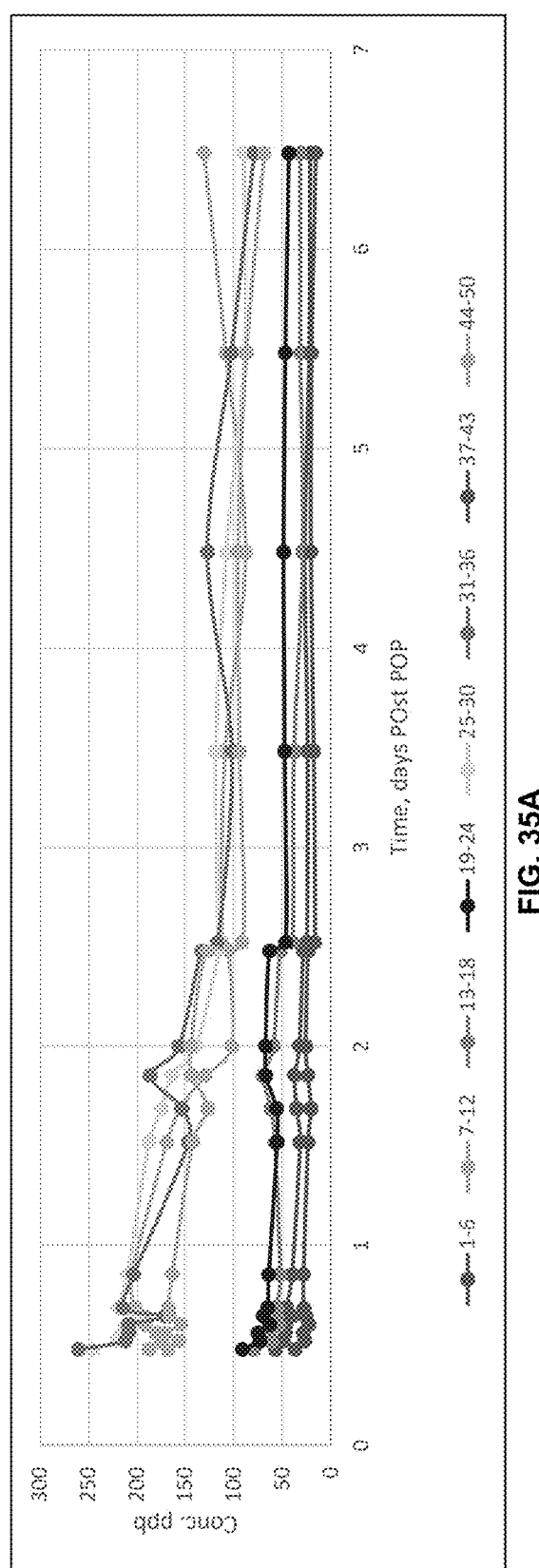
Figure 35B:
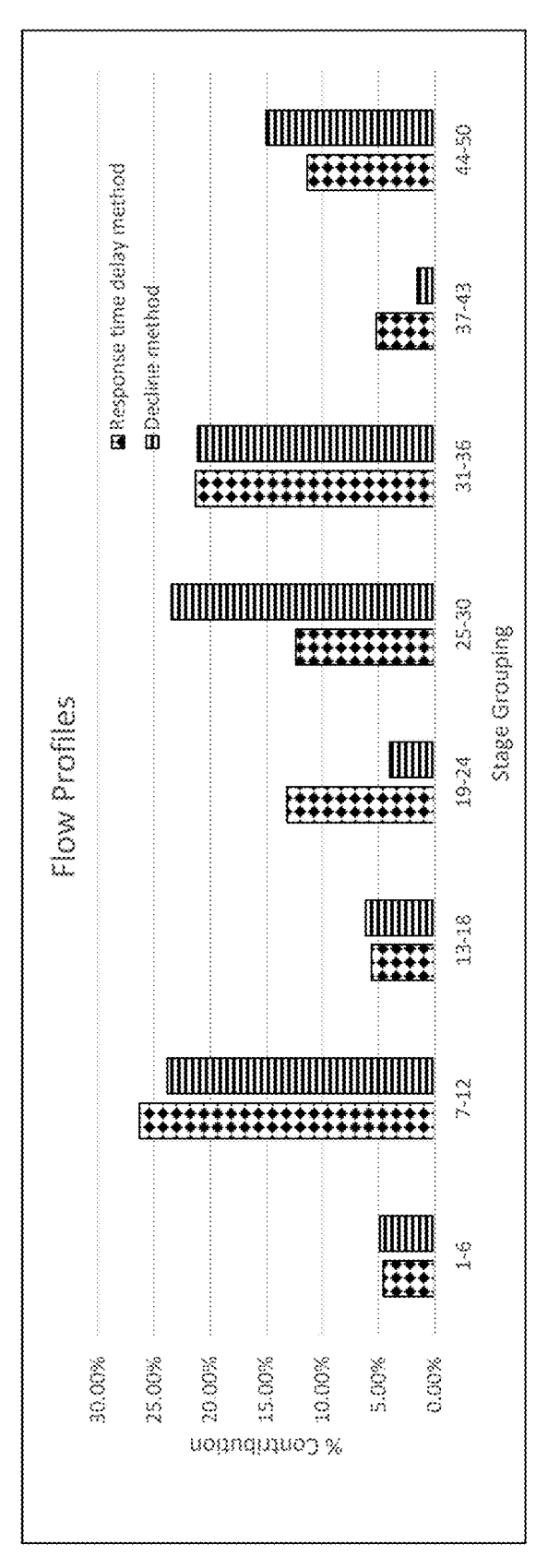

Response Time Delay Method and Decline Method Examples:

FIGS. 33A-33H illustrate various examples of flow profiles for an oil phase only (i.e., unique oil particulate tracers are pumped throughout stage groups) and corresponding tracer concentrations histories for the examples. Tracer concentration histories for time period A (Post POP) in FIG. 33D and for time period B in 33A are illustrated in the figures. Logging information for time period C was also obtained and utilized for comparisons. In FIGS. 33B-33C and 33G-33H, tracer interpretation shows good correspondence with the logging interpretation. In FIGS. 33D-33E, tracer interpretation post POP using the response time delay method for period A and using the delay method for period B also show change in the flow contribution from the toe stages in the 3 month production period, which allows for time-based flow profiling. The response time delay method and the decline method may be utilized on the substantially same data as illustrated in FIGS. 33G-33H. FIGS. 34A-34B and 35A also illustrate tracer concentration histories used with the response time delay method and the decline method as in FIGS. 34C and 35B, respectively.

A person of ordinary skill in the art will appreciate that tracer based flow profiling may accomplish the following: (1) eliminate uncertainty due to well trajectory, (2) uncertainty due to multi-phase flow issues in the wellbore if the reservoir contact volume is larger than the wellbore volume, and/or (3) flow profiling as a function of time with minimal intervention (e.g., shutting in the well for 24 to 48 hours and high frequency sampling post shut-in). Of note, (a) tracer release rate understanding is important for correct interpretation post POP in the flowing life of the wellbore for response time delay method, but the decline method is independent of the release rate as long as enough tracer is detected, (b) flowback sampling frequency post shut-in should be high when the oil flowrates increase for response time delay method to work correctly, (c) lower resolution because of the limitation with the number of tracers available, and/or (d) 24 hour LPO if flow profiling is desired after initial POP but could be synchronized with planned shut-ins/workovers. Of note, some considerations include (I) does not depend on the release rate explicitly but assumes that all the particulate tracers have the same release rate as a function of time and would enable flow profiling over time, (II) tracer baseline can be deduced from the tracer signal itself if the previous statement on tracer design is true, and/or (III) particulate tracers may provide meaningful signal over the early life (at least 1 year) of the well. Advantages include: (i) non-interventional flow profiling which could be used upto 12 months and extended to 18 months and/or (ii) test could be planned when changes in well behavior are observed. Indeed, it is oftentimes difficult, expensive, or not practical to use logging tools and generate logging data (e.g., especially in geographically remote areas) so tracer-based flow profiling may provide adequate flow profiles, even though tracer based flow profiling may produce lower resolution data as compared to logging data. Computer System:

The system 3600 may include one or more of a processor 3618, an interface 3620 (e.g., bus, wireless interface), an electronic storage 3622, a graphical display 3624, and/or other components. The electronic storage 3622 may be configured to include electronic storage medium that electronically stores information (e.g., non-transitory storage media that electronically stores information). The electronic storage 3622 may store software algorithms, information determined by the processor 3618, information received remotely, and/or other information that enables the system 3600 to function properly. The electronic storage media of the electronic storage 3622 may be provided integrally (i.e., substantially non-removable) with one or more components of the system 3600 and/or as removable storage that is connectable to one or more components of the system 3600 via, for example, a port (e.g., a USB port, a Firewire port, etc.) or a drive (e.g., a disk drive, etc.). The electronic storage 3622 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. The electronic storage 3622 may be a separate component within the system 3600, or the electronic storage 3622 may be provided integrally with one or more other components of the system 3600 (e.g., the processor 3618). Although the electronic storage 3622 is shown in FIG. 36 as a single entity, this is for illustrative purposes only. In some implementations, the electronic storage 3622 may comprise a plurality of storage units. These storage units may be physically located within the same device, or the electronic storage 3622 may represent storage functionality of a plurality of devices operating in coordination.

The graphical display 3624 may refer to an electronic device that provides visual presentation of information. The graphical display 3624 may include a color display and/or a non-color display. The graphical display 3624 may be configured to visually present information. The graphical display 3624 may present information using/within one or more graphical user interfaces.

The processor 3618 may be configured to provide information processing capabilities in the system 3600. As such, the processor 3618 may comprise one or more of a digital processor, an analog processor, a digital circuit designed to process information, a central processing unit, a graphics processing unit, a microcontroller, an analog circuit designed to process information, a state machine, and/or other mechanisms for electronically processing information. The processor 3618 may be configured to execute one or more machine-readable instructions 3602. The machine-readable instructions 3602 may include one or more computer program components.

It should be appreciated that although computer program components are illustrated in FIG. 36 as being co-located within a single processing unit, one or more of computer program components may be located remotely from the other computer program components. While computer program components are described as performing or being configured to perform operations, computer program components may comprise instructions which may program processor 3618 and/or system 3600 to perform the operation.

While computer program components are described herein as being implemented via processor 3618 through machine-readable instructions 3602, this is merely for ease of reference and is not meant to be limiting. In some implementations, one or more functions of computer program components described herein may be implemented via hardware (e.g., dedicated chip, field-programmable gate array) rather than software. One or more functions of computer program components described herein may be software-implemented, hardware-implemented, or software and hardware-implemented.

The description of the functionality provided by the different computer program components described herein is for illustrative purposes, and is not intended to be limiting, as any of computer program components may provide more or less functionality than is described. For example, one or more of computer program components may be eliminated, and some or all of its functionality may be provided by other computer program components. As another example, processor 3618 may be configured to execute one or more additional computer program components that may perform some or all of the functionality attributed to one or more of computer program components described herein.

While particular embodiments are described above, it will be understood it is not intended to limit the invention to these particular embodiments. On the contrary, the invention includes alternatives, modifications and equivalents that are within the spirit and scope of the appended claims. Numerous specific details are set forth in order to provide a thorough understanding of the subject matter presented herein. But it will be apparent to one of ordinary skill in the art that the subject matter may be practiced without these specific details. In other instances, well-known methods, procedures, components, and circuits have not been described in detail so as not to unnecessarily obscure aspects of the embodiments.

The terminology used in the description of the invention herein is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, operations, elements, and/or components, but do not preclude the presence or addition of one or more other features, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of ±10 percent of the given numeric value provided such a deviation does not alter the end function or result of the value. Therefore, a value of about 1% can be construed to be a range from 0.9% to 1.1%. Furthermore, a range may be construed to include the start and the end of the range. For example, a range of 10% to 20% (i.e., range of 10%-20%) includes 10% and also includes 20%, and includes percentages in between 10% and 20%, unless explicitly stated otherwise herein. Similarly, a range of between 10% and 20% (i.e., range between 10%-20%) includes 10% and also includes 20%, and includes percentages in between 10% and 20%, unless explicitly stated otherwise herein.

It is understood that when combinations, subsets, groups, etc. of elements are disclosed (e.g., combinations of components in a composition, or combinations of steps in a method), that while specific reference of each of the various individual and collective combinations and permutations of these elements may not be explicitly disclosed, each is specifically contemplated and described herein. By way of example, if an item is described herein as including a component of type A, a component of type B, a component of type C, or any combination thereof, it is understood that this phrase describes all of the various individual and collective combinations and permutations of these components. For example, in some embodiments, the item described by this phrase could include only a component of type A. In some embodiments, the item described by this phrase could include only a component of type B. In some embodiments, the item described by this phrase could include only a component of type C. In some embodiments, the item described by this phrase could include a component of type A and a component of type B. In some embodiments, the item described by this phrase could include a component of type A and a component of type C. In some embodiments, the item described by this phrase could include a component of type B and a component of type C. In some embodiments, the item described by this phrase could include a component of type A, a component of type B, and a component of type C. In some embodiments, the item described by this phrase could include two or more components of type A (e.g., A1 and A2). In some embodiments, the item described by this phrase could include two or more components of type B (e.g., B1 and B2). In some embodiments, the item described by this phrase could include two or more components of type C (e.g., C1 and C2). In some embodiments, the item described by this phrase could include two or more of a first component (e.g., two or more components of type A (A1 and A2)), optionally one or more of a second component (e.g., optionally one or more components of type B), and optionally one or more of a third component (e.g., optionally one or more components of type C). In some embodiments, the item described by this phrase could include two or more of a first component (e.g., two or more components of type B (B1 and B2)), optionally one or more of a second component (e.g., optionally one or more components of type A), and optionally one or more of a third component (e.g., optionally one or more components of type C). In some embodiments, the item described by this phrase could include two or more of a first component (e.g., two or more components of type C (C1 and C2)), optionally one or more of a second component (e.g., optionally one or more components of type A), and optionally one or more of a third component (e.g., optionally one or more components of type B).

This written description uses examples to disclose the invention, including the best mode, and also to enable any person skilled in the art to make and use the invention. The patentable scope is defined by the claims, and may include other examples that occur to those skilled in the art. Such other examples are intended to be within the scope of the claims if they have elements that do not differ from the literal language of the claims, or if they include equivalent elements with insubstantial differences from the literal language of the claims.

Unless defined otherwise, all technical and scientific terms used herein have the same meanings as commonly understood by one of skill in the art to which the disclosed invention belongs. All citations referred herein are expressly incorporated by reference.

T-11543A:

This disclosure includes the following elements:

Element 1. A method of placing unique particulate tracers in a subterranean formation having a wellbore therewithin, the method comprising: placing unique particulate tracers in at least two stages, including a first stage and a second stage, during a hydraulic fracturing operation in a subterranean formation, wherein the unique particulate tracers are pumped only in a fraction of each stage such that a substantial portion of the unique particulate tracers are placed in a near wellbore region of the subterranean formation proximate to the wellbore drilled into the subterranean formation, and wherein at least one unique particulate tracer is pumped in the fraction of each stage, and wherein each unique particulate tracer corresponds to an oil phase, a water phase, or a gas phase.

Element 2. The method of element 1, further comprising determining a minimum wellbore volume between the first stage and the second stage.

Element 3. The method of element 1, further comprising determining a minimum length between the first stage and the second stage.

Element 4. The method of element 1, further comprising determining a quantity of stages without the unique particulate tracers between the first stage and the second stage.

Element 5. The method of element 1, further comprising determining a maximum fluid volume in a stage near the wellbore that is in contact with unique particulate tracer once for each phase.

Element 6. The method of element 1, further comprising determining a proppant pack bulk volume once for each phase.

Element 7. The method of element 1, further comprising determining a proppant mass tagged with a unique particulate tracer once for each phase.

Element 8. The method of element 1, further comprising determining proppant pumped in a stage once, and utilizing the substantially same answer for each phase.

Element 9. The method of element 1, further comprising determining a fraction of a stage in which to pump a unique particulate tracer once for each phase.

Element 10. The method of element 1, wherein a fraction of a stage is determined with an equation as follows:

$$\text{fraction of stage tagged with a unique particulate tracer} = \frac{\text{Tagged proppant mass, lbs}}{M_{p,stage}\text{lbs}}$$

wherein fraction of stage tagged with a unique particulate tracer is percentage of a stage, tagged proppant mass is proppant mass tagged with a unique particulate tracer, and $M_{p,stage}$ is proppant pumped in a stage.

Element 11. The method of element 1, wherein a fraction of a stage in which to pump a unique particulate tracer comprises 0.001% to 50%.

Element 12. The method of element 1, further comprising pumping a proppant mass that is tagged with a unique particulate tracer in a fraction of a stage.

Element 13. The method of element 1, further comprising determining a dilution amplification factor once for each phase.

Element 14. The method of element 1, further comprising determining a unique particulate tracer mass released once for each phase.

Element 15. The method of element 1, further comprising determining design particulate mass once for each phase.

Element 16. The method of element 1, further comprising determining design particulate mass to tagged proppant ratio once for each phase.

Element 17. A system of placing unique particulate tracers in a subterranean formation having a wellbore therewithin, the system comprising: a wellbore drilled into a subterranean formation; and unique particulate tracers, wherein the unique particulate tracers are placed in at least two stages, including a first stage and a second stage, during a hydraulic fracturing operation in the subterranean formation, wherein the unique particulate tracers are pumped only in a fraction of each stage such that a substantial portion of the unique particulate tracers are placed in a near wellbore region of the subterranean formation proximate to the wellbore, and wherein at least one unique particulate tracer is pumped in the fraction of each stage, and wherein each unique particulate tracer corresponds to an oil phase, a water phase, or a gas phase.

Element 18. A method of determining a fraction of a stage in which to place a unique particulate tracer, the method comprising: determining, with a physical computer processor, a fraction of a stage in which to place a unique particulate tracer to facilitate placement of unique particulate tracers in at least two stages, including a first stage and a second stage, during a hydraulic fracturing operation in a subterranean formation, wherein the unique particulate tracers are pumped only in a fraction of each stage such that a substantial portion of the unique particulate tracers are placed in a near wellbore region of the subterranean formation proximate to the wellbore drilled into the subterranean formation, and wherein at least one unique particulate tracer is pumped in the fraction of each stage, and wherein each unique particulate tracer corresponds to an oil phase, a water phase, or a gas phase.

Element 19. The method of element 18, wherein a fraction of a stage is determined with an equation as follows:

$$\text{fraction of stage tagged with a unique particulate tracer} = \frac{\text{Tagged proppant mass, lbs}}{M_{p,stage}\text{lbs}}$$

wherein fraction of stage tagged with a unique particulate tracer is percentage of a stage, tagged proppant mass is proppant mass tagged with a unique particulate tracer, and $M_{p,stage}$ is proppant pumped in a stage.

Element 20. The method of element 1, wherein a fraction of a stage in which to pump a unique particulate tracer comprises 0.001% to 50%.

T-11543B:

This disclosure includes the following elements:

Element 1. A method of determining a flow profile for a wellbore using unique particulate tracers, the method comprising: obtaining produced fluid samples comprising unique particulate tracers from a wellbore drilled into a subterranean formation, wherein the unique particulate tracers are pumped in at least one stage pair during a hydraulic fracturing operation performed in the subterranean formation, and wherein the unique particulate tracers are pumped only in a fraction of each stage such that a substantial portion of the unique particulate tracers are placed in a near wellbore region of the subterranean formation proximate to the wellbore, and wherein at least one unique particulate tracer is pumped in the fraction of each stage, and wherein each unique particulate tracer corresponds to an oil phase, a water phase, or a gas phase; and determining a flow profile for the wellbore for each phase using the produced fluid samples comprising the unique particulate tracers by: i) obtaining a tracer concentration history for each unique particulate tracer; ii) determining a wellbore volume for the stage pair; and (iii) determining a flow profile for the wellbore for each phase indicative of flow contribution for each stage pair and stages within each stage pair using the wellbore volume and the corresponding tracer concentration histories.

Element 2. The method of element 1, wherein the wellbore volume is determined using an equation as follows:

$$V_{wellbore} = L_{wellbore}\text{ft} * \pi r_w^2$$

wherein $V_{wellbore}$ is wellbore volume, $L_{wellbore}$ ft is length for a specific stage pair, and $r_w$ is a flow pipe radius.

Element 3. The method of element 1, wherein the flow contribution is determined using an equation as follows:

$$q_{N,bbls/day} = \frac{V_{wellbore,N}, (bbls) * 24 * 60}{\Delta t, \text{minutes}}$$

wherein $q_{N,bbls/day}$ is flow contribution for a specific stage pair, $V_{wellbore}$ is wellbore volume, $\Delta t$ is arrival time difference, and N is a specific stage.

Element 4. The method of element 1, further comprising: obtaining a production history for the wellbore; summing all flow contributions for each stage pair for each phase; and comparing the sums and the production history to constraint total flow contribution for each phase.

Element 5. The method of element 1, further comprising: smoothing a tracer concentration history for a specific unique particulate tracer before iii) to reduce noise; and utilizing the smoothed tracer concentration history for the specific unique particulate tracer in iii).

Element 6. The method of element 1, further comprising refining the wellbore volume in response to multiple phases in the wellbore.

Element 7. The method of element 1, further comprising: generating, on a graphical user interface, a representation of the flow profile for the wellbore for each phase indicative of the flow contribution for each stage pair and stages within each stage pair; and displaying, via the graphical user interface, the representation.

Element 8. A method of determining a flow profile for a wellbore using unique particulate tracers, the method being implemented in a computer system that includes a physical computer processor and non-transitory storage medium, the method comprising: i) obtaining, the from a non-transitory storage medium, a tracer concentration history for each unique particulate tracer in produced fluid samples from a wellbore drilled into a subterranean formation, wherein the unique particulate tracers are pumped in at least one stage pair during a hydraulic fracturing operation performed in the subterranean formation, and wherein the unique particulate tracers are pumped only in a fraction of each stage such that a substantial portion of the unique particulate tracers are placed in a near wellbore region of the subterranean formation proximate to the wellbore, and wherein at least one unique particulate tracer is pumped in the fraction of each stage, and wherein each unique particulate tracer corresponds to an oil phase, a water phase, or a gas phase; ii) determining, with the physical computer processor, a wellbore volume for the stage pair; and iii) determining, with the physical computer processor, a flow profile for the wellbore for each phase indicative of flow contribution for each stage pair and stages within each stage pair using the wellbore volume and the corresponding tracer concentration histories.

Element 9. The method of element 8, wherein the wellbore volume is determined using an equation as follows:

$$V_{wellbore} = L_{wellbore} \text{ft} * \pi r_w^2$$

wherein $V_{wellbore}$ is wellbore volume, $L_{wellbore}$ ft is length for a specific stage pair, and $r_w$ is a flow pipe radius.

Element 10. The method of element 8, wherein the flow contribution is determined using an equation as follows:

$$q_{N,bbls/day} = \frac{V_{wellbore,N}, (bbls) * 24 * 60}{\Delta t, \text{minutes}}$$

wherein $q_{N,bbls/day}$ is flow contribution for a specific stage pair, $V_{wellbore}$ is wellbore volume, $\Delta t$ is arrival time difference, and N is a specific stage.

Element 11. The method of element 8, further comprising: obtaining a production history for the wellbore; summing all flow contributions for each stage pair for each phase; and comparing the sums and the production history to constraint total flow contribution for each phase.

Element 12. The method of element 8, further comprising: smoothing a tracer concentration history for a specific unique particulate tracer before iii) to reduce noise; and utilizing the smoothed tracer concentration history for the specific unique particulate tracer in iii).

Element 13. The method of element 8, further comprising refining the wellbore volume in response to multiple phases in the wellbore.

Element 14. The method of element 8, further comprising: generating, on a graphical user interface, a representation of the flow profile for the wellbore for each phase indicative of the flow contribution for each stage pair and stages within each stage pair; and displaying, via the graphical user interface, the representation.

Element 15. A computer system, comprising: one or more processors; memory; and one or more programs, wherein the one or more programs are stored in the memory and configured to be executed by the one or more processors, the one or more programs including instructions that when executed by the one or more processors cause the system to a method of determining a flow profile for a wellbore using unique particulate tracers, the method comprising: i) obtaining a tracer concentration history for each unique particulate tracer in produced fluid samples from a wellbore drilled into a subterranean formation, wherein the unique particulate tracers are pumped in at least one stage pair during a hydraulic fracturing operation performed in the subterranean formation, and wherein the unique particulate tracers are pumped only in a fraction of each stage such that a substantial portion of the unique particulate tracers are placed in a near wellbore region of the subterranean formation proximate to the wellbore, and wherein at least one unique particulate tracer is pumped in the fraction of each stage, and wherein each unique particulate tracer corresponds to an oil phase, a water phase, or a gas phase; ii) determining a wellbore volume for the stage pair; and iii) determining a flow profile for the wellbore for each phase indicative of flow contribution for each stage pair and stages within each stage pair using the wellbore volume and the corresponding tracer concentration histories.

Element 16. The system of element 15, wherein the wellbore volume is determined using an equation as follows:

$$V_{wellbore} = L_{wellbore} \text{ft} * \pi r_w^2$$

wherein $V_{wellbore}$ is wellbore volume, $L_{wellbore}$ ft is length for a specific stage pair, and $r_w$ is a flow pipe radius.

Element 17. The system of element 15, wherein the flow contribution is determined using an equation as follows:

$$q_{N,bbls/day} = \frac{V_{wellbore,N}, (bbls) * 24 * 60}{\Delta t, \text{minutes}}$$

wherein $q_{N,bbls/day}$ is flow contribution for a specific stage pair, $V_{wellbore}$ is wellbore volume, $\Delta t$ is arrival time difference, and N is a specific stage.

Element 18. The system of element 15, further comprising: obtaining a production history for the wellbore; summing all flow contributions for each stage pair for each phase; and comparing the sums and the production history to constraint total flow contribution for each phase.

Element 19. The system of element 15, further comprising: smoothing a tracer concentration history for a specific unique particulate tracer before iii) to reduce noise; and utilizing the smoothed tracer concentration history for the specific unique particulate tracer in iii).

Element 20. The system of element 15, further comprising refining the wellbore volume in response to multiple phases in the wellbore.

Element 21. The system of element 15, further comprising a graphical user interface: generating, on the graphical user interface, a representation of the flow profile for the wellbore for each phase indicative of the flow contribution for each stage pair and stages within each stage pair; and displaying, via the graphical user interface, the representation.

T-11543C:

This disclosure includes the following elements:

Element 1. A method of determining a flow profile for a wellbore using unique particulate tracers, the method comprising: obtaining produced fluid samples comprising unique particulate tracers from a wellbore drilled into a subterranean formation, wherein at least one unique particulate tracer is pumped throughout each stage, each stage group, or any combination thereof during a hydraulic fracturing operation performed in the subterranean formation, and wherein each unique particulate tracer corresponds to an oil phase, a water phase, or a gas phase, and wherein the produced fluid samples comprise at least a portion of the unique particulate tracers that were pumped throughout the stages, the stage groups, or any combination thereof; and determining a flow profile for the wellbore for each phase using the produced fluid samples comprising the unique particulate tracers by: a) obtaining a tracer concentration history for each unique particulate tracer; b) obtaining a production history for the wellbore; c) determining a mean residence time for each unique particulate tracer using the corresponding tracer concentration history; d) determining a contact volume proxy for each unique particulate tracer using the production history and the corresponding tracer concentration history; and e) determining the flow profile for the wellbore for each phase indicative of flow contribution of each stage, each stage group, or any combination thereof by using the corresponding mean residence times and the corresponding contact volume proxies.

Element 2. The method of element 1, wherein the mean residence time is determined using an equation as follows:

$$ t_{res} = \frac{\int_{t=0}^{t=\infty} c*t*dt}{\int_{t=0}^{t=\infty} c*dt} $$

wherein $t_{res}$ is mean residence time, c is tracer concentration history, t is time, and dt is integration with respect to time.

Element 3. The method of element 1, wherein the contact volume proxy is determined using an equation as follows:

$$ vol_{proxy} = \int_{t=0}^{t=\infty} q*c*dt $$

wherein $vol_{proxy}$ is contact volume proxy, q is production history, c is tracer concentration history, t is time, and dt is integration with respect to time.

Element 4. The method of element 1, wherein the flow profile is determined using an equation as follows:

$$ flow\_contribution_N(\%) = \frac{\dfrac{vol_{proxy\_N}}{t_{res\_N}}}{\sum_{i=1}^{i=M} \dfrac{vol_{proxy\_i}}{t_{res\_i}}} * 100 $$

wherein $flow\_contribution_N$ is flow contribution for a specific stage or specific stage group, $t_{res}$ is mean residence time, $contact\_vol_{proxy}$ is contact volume proxy, i is a counter, M is total number of stages or stage groups in which unique particulate tracers were pumped, and N is specific stage or specific stage group for which flow contribution is determined.

Element 5. The method of element 1, further comprising: smoothing a tracer concentration history for a specific unique particulate tracer before c) and d) to reduce noise; and utilizing the smoothed tracer concentration history for the specific unique particulate tracer in c) and d).

Element 6. The method of element 1, wherein the computer system further includes a graphical user interface, and the method further comprises: generating, on the graphical user interface, a representation of the flow profile for the wellbore for each phase indicative of the flow contribution of each stage, each stage group, or any combination thereof; and displaying, via the graphical user interface, the representation.

Element 7. The method of element 1, before obtaining the produced fluid samples, further comprising: shutting in the wellbore for a period of time to cause tracer clouds to form in the subterranean formation for at least a portion of the unique particulate tracers that were pumped throughout the stages, the stage groups, or any combination thereof.

Element 8. The method of element 7, after the period of time, further comprising flowing back the wellbore to cause produced fluid from the wellbore and the produced fluid samples are obtained from the produced fluid, and wherein the produced fluid samples comprise at least a portion of the unique particulate tracers that were pumped throughout the stages, the stage groups, or any combination thereof from the tracer clouds.

Element 9. The method of element 7, further comprising analyzing the produced fluid samples obtained from the produced fluid to generate the tracer concentration history for each unique particulate tracer.

Element 10. A method of determining a flow profile for a wellbore using unique particulate tracers, the method being implemented in a computer system that includes a physical computer processor and non-transitory storage medium, the method comprising: a) obtaining, from a non-transitory storage medium, a tracer concentration history for each unique particulate tracer in produced fluid samples from a wellbore drilled into a subterranean formation, wherein at least one unique particulate tracer is pumped throughout each stage, each stage group, or any combination thereof during a hydraulic fracturing operation performed in the subterranean formation, and wherein each unique particulate tracer corresponds to an oil phase, a water phase, or a gas phase, and wherein the produced fluid samples comprise at least a portion of the unique particulate tracers that were pumped throughout the stages, the stage groups, or any combination thereof; b) obtaining, from the non-transitory storage medium, a production history for the wellbore; c) determining, with a physical computer processor, a mean residence time for each unique particulate tracer using the corresponding tracer concentration history; d) determining, with the physical computer processor, a contact volume proxy for each unique particulate tracer using the production history and the corresponding tracer concentration history; and e) determining, with the physical computer processor, a flow profile for the wellbore for each phase indicative of flow contribution of each stage, each stage group, or any combination thereof by using the corresponding mean residence times and the corresponding contact volume proxies.

Element 11. The method of element 10, wherein the mean residence time is determined using an equation as follows:

$$t_{res} = \frac{\int_{t=0}^{t=\infty} c * t * dt}{\int_{t=0}^{t=\infty} c * dt}$$

wherein $t_{res}$ is mean residence time, c is tracer concentration history, t is time, and dt is integration with respect to time.

Element 12. The method of element 10, wherein the contact volume proxy is determined using an equation as follows:

$$vol_{proxy} = \int_{t=0}^{t=\infty} q * c * dt$$

wherein $vol_{proxy}$ is contact volume proxy, q is production history, c is tracer concentration history, t is time, and dt is integration with respect to time.

Element 13. The method of element 10, wherein the flow profile is determined using an equation as follows:

$$flow\_contribution_N(\%) = \frac{\frac{vol_{proxy\_N}}{t_{res\_N}}}{\sum_{i=1}^{i=M} \frac{vol_{proxy\_i}}{t_{res\_i}}} * 100$$

wherein flow_contribution$_N$ is flow contribution for a specific stage or specific stage group, $t_{res}$ is mean residence time, contact_vol$_{proxy}$ is contact volume proxy, i is a counter, M is total number of stages or stage groups in which unique particulate tracers were pumped, and N is specific stage or specific stage group for which flow contribution is determined.

Element 14. The method of element 10, further comprising: smoothing a tracer concentration history for a specific unique particulate tracer before c) and d) to reduce noise; and utilizing the smoothed tracer concentration history for the specific unique particulate tracer in c) and d).

Element 15. The method of element 10, wherein the computer system further includes a graphical user interface, and the method further comprises: generating, on the graphical user interface, a representation of the flow profile for the wellbore for each phase indicative of the flow contribution of each stage, each stage group, or any combination thereof; and displaying, via the graphical user interface, the representation.

Element 16. A method of determining a flow profile for a wellbore using unique particulate tracers, the method comprising: obtaining produced fluid samples comprising unique particulate tracers from a wellbore drilled into a subterranean formation, wherein at least one unique particulate tracer is pumped throughout each stage, each stage group, or any combination thereof during a hydraulic fracturing operation performed in the subterranean formation, and wherein each unique particulate tracer corresponds to an oil phase, a water phase, or a gas phase, and wherein the produced fluid samples comprise at least a portion of the unique particulate tracers that were pumped throughout the stages, the stage groups, or any combination thereof; and determining a flow profile for the wellbore for each phase using the produced fluid samples comprising the unique particulate tracers by: a) obtaining a tracer concentration history for each unique particulate tracer; b) optionally obtaining a production history for the wellbore; c) determining a decline rate for each unique particulate tracer using the corresponding tracer concentration history; d) determining a normalization factor for each unique particulate tracer using the corresponding tracer concentration history and optionally the production history; e) determining a normalized decline rate for each unique particulate tracer using the corresponding decline rate and the corresponding normalization factor; and f) determining a flow profile for the wellbore for each phase indicative of flow contribution of each stage, each stage group, or any combination thereof by using the corresponding normalized decline rates.

Element 17. The method of element 16, wherein the decline rate is determined using an equation as follows:

$$r = \frac{dc}{dt}$$

wherein r is decline rate, dC is integration with respect to tracer concentration history, and dt is integration with respect to time.

Element 18. The method of element 16, wherein the normalization factor is represented as norm$_{factor}$=c$_{mode}$ wherein norm_factor is normalization factor and c_mode is a maximum value of a tracer concentration history.

Element 19. The method of element 16, wherein the normalization factor is determined using an equation as follows:

$$norm_{factor} = \int_{t=0}^{t=\infty} q * \rho * c * dt$$

wherein norm_factor is normalization factor, t is time, q is production history, $\rho$ is fluid density, c is tracer concentration history, and dt is integration with respect to time.

Element 20. The method of element 16, wherein the normalized decline rate is determined using an equation as follows:

$$r\_norm = \frac{r}{norm\_factor}$$

wherein r_norm is normalized decline rate, r is decline rate, and norm_factor is normalization factor.

Element 21. The method of element 16, wherein the flow profile is determined using an equation as follows:

$$\text{flow\_contribution}_N(\%) = \frac{r_{norm\_N}}{\sum_{i=1}^{i=M} r_{norm\_i}} * 100$$

wherein flow_contribution$_N$ is flow contribution for a specific stage or specific stage group, r$_{norm}$ is normalized decline rate, i is a counter, M is total number of stages or stage groups in which unique particulate tracers were pumped, and N is specific stage or specific stage group for which flow contribution is determined.

Element 22. The method of element 16, further comprising: smoothing a tracer concentration history for a specific unique particulate tracer before c) and d) to reduce noise; and utilizing the smoothed tracer concentration history for the specific unique particulate tracer in c) and d).

Element 23. The method of element 16, wherein the computer system further includes a graphical user interface, and the method further comprises: generating, on the graphical user interface, a representation of the flow profile for the wellbore for each phase indicative of the flow contribution of each stage, each stage group, or any combination thereof; and displaying, via the graphical user interface, the representation.

Element 24. A method of determining a flow profile for a wellbore using unique particulate tracers, the method being implemented in a computer system that includes a physical computer processor and non-transitory storage medium, the method comprising: a) obtaining, from a non-transitory storage medium, a tracer concentration history for each unique particulate tracer in produced fluid samples from a wellbore drilled into a subterranean formation, wherein at least one unique particulate tracer is pumped throughout each stage, each stage group, or any combination thereof during a hydraulic fracturing operation performed in the subterranean formation, and wherein each unique particulate tracer corresponds to an oil phase, a water phase, or a gas phase, and wherein the produced fluid samples comprise at least a portion of the unique particulate tracers that were pumped throughout the stages, the stage groups, or any combination thereof; b) optionally obtaining, from the non-transitory storage medium, a production history for the wellbore; c) determining, with a physical computer processor, a decline rate for each unique particulate tracer using the corresponding tracer concentration history; d) determining, with the physical computer processor, a normalization factor for each unique particulate tracer using the corresponding tracer concentration history and optionally the production history; e) determining, with the physical computer processor, a normalized decline rate for each unique particulate tracer using the corresponding decline rate and the corresponding normalization factor; and f) determining, with the physical computer processor, a flow profile for the wellbore for each phase indicative of flow contribution of each stage, each stage group, or any combination thereof by using the corresponding normalized decline rates.

Element 25. The method of element 24, wherein the decline rate is determined using an equation as follows:

$$r = \frac{dc}{dt}$$

wherein r is decline rate, dC is integration with respect to tracer concentration history, and dt is integration with respect to time.

Element 26. The method of element 24, wherein the normalization factor is represented as $$norm_{factor} = c_{mode}$$

wherein norm_factor is normalization factor and c_mode is a maximum value of a tracer concentration history.

Element 27. The method of element 24, wherein the normalization factor is determined using an equation as follows:

$$norm_{factor} = \int_{t=0}^{t=\infty} q * \rho * c * dt$$

wherein norm_factor is normalization factor, t is time, q is production history, ρ is fluid density, c is tracer concentration history, and dt is integration with respect to time.

Element 28. The method of element 24, wherein the normalized decline rate is determined using an equation as follows:

$$\text{r\_norm} = \frac{r}{norm\_factor}$$

wherein r_norm is normalized decline rate, r is decline rate, and norm_factor is normalization factor.

Element 29. The method of element 24, wherein the flow profile is determined using an equation as follows:

$$\text{flow\_contribution}_N(\%) = \frac{r_{norm\_N}}{\sum_{i=1}^{i=M} r_{norm\_i}} * 100$$

wherein flow_contribution$_N$ is flow contribution for a specific stage or specific stage group, r$_{norm}$ is normalized decline rate, i is a counter, M is total number of stages or stage groups in which unique particulate tracers were pumped, and N is specific stage or specific stage group for which flow contribution is determined.

Element 30. The method of element 24, further comprising: smoothing a tracer concentration history for a specific unique particulate tracer before c) and d) to reduce noise; and utilizing the smoothed tracer concentration history for the specific unique particulate tracer in c) and d).

Element 31. The method of element 24, wherein the computer system further includes a graphical user interface, and the method further comprises: generating, on the graphical user interface, a representation of the flow profile for the wellbore for each phase indicative of the flow contribution of each stage, each stage group, or any combination thereof; and displaying, via the graphical user interface, the representation.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A method of determining a flow profile for a wellbore using unique particulate tracers, the method comprising:

pumping, through a wellbore drilled into a subterranean formation, unique particulate tracers throughout each stage, each stage group, or any combination thereof during a hydraulic fracturing operation performed in the subterranean formation, wherein each unique particulate tracer corresponds to an oil phase, a water phase, or a gas phase;

obtaining produced fluid samples from the wellbore, wherein the produced fluid samples comprise at least a portion of the unique particulate tracers that were pumped throughout the stages, the stage groups, or any combination thereof; and determining a flow profile for the wellbore for each phase using the produced fluid samples comprising the unique particulate tracers by:

a) obtaining a tracer concentration history for each unique particulate tracer;

b) obtaining a production history for the wellbore;

c) determining a mean residence time for each unique particulate tracer using the corresponding tracer concentration history;

d) determining a contact volume proxy for each unique particulate tracer using the production history and the corresponding tracer concentration history; and e) determining the flow profile for the wellbore for each phase indicative of flow contribution of each stage, each stage group, or any combination thereof by using the corresponding mean residence times and the corresponding contact volume proxies, wherein:

the contact volume proxy of a specific unique particulate tracer refers to an approximate volume of the subterranean formation that was contacted by the specific unique particulate tracer; and determining the flow profile for the wellbore for each phase comprises, for each phase, determining the flowrate of each stage, each stage group, or any combination thereof based on the contact volume proxy over mean residence time for that stage or stage group or any combination thereof.

2. The method of claim 1, wherein the mean residence time is determined using an equation as follows:

$$t_{res} = \frac{\int_{t=0}^{t=\infty} c * t * dt}{\int_{t=0}^{t=\infty} c * dt}$$

wherein $t_{res}$ is mean residence time, c is tracer concentration history, t is time, and dt is integration with respect to time.

3. The method of claim 1, wherein the contact volume proxy is determined using an equation as follows:

$$vol_{proxy} = \int_{t=0}^{t=\infty} q * c * dt$$

wherein $vol_{proxy}$ is contact volume proxy, q is production history, c is tracer concentration history, t is time, and dt is integration with respect to time.

4. The method of claim 1, wherein the flow profile is determined using an equation as follows:

$$\text{flow\_contribution}_N(\%) = \frac{\frac{vol_{proxy\_N}}{t_{res\_N}}}{\sum_{i=1}^{i=M} \frac{vol_{proxy\_i}}{t_{res\_i}}} * 100$$

wherein flow_contribution$_N$ is flow contribution for a specific stage or specific stage group, $t_{res}$ is mean residence time, contact_vol$_{proxy}$ is contact volume proxy, i is a counter, M is total number of stages or stage groups in which unique particulate tracers were pumped, and N is specific stage or specific stage group for which flow contribution is determined.

5. The method of claim 1, further comprising:

smoothing a tracer concentration history for a specific unique particulate tracer before c) and d) to reduce noise; and utilizing the smoothed tracer concentration history for the specific unique particulate tracer in c) and d).

6. The method of claim 1, further comprising:

generating, on a graphical user interface, a representation of the flow profile for the wellbore for each phase indicative of the flow contribution of each stage, each stage group, or any combination thereof; and displaying, via the graphical user interface, the representation.

7. The method of claim 1, before obtaining the produced fluid samples, further comprising:

shutting in the wellbore for a period of time to cause tracer clouds to form in the subterranean formation for at least a portion of the unique particulate tracers that were pumped throughout the stages, the stage groups, or any combination thereof.

8. The method of claim 7, after the period of time, further comprising flowing back the wellbore to cause produced fluid from the wellbore and the produced fluid samples are obtained from the produced fluid, and wherein the produced fluid samples comprise at least a portion of the unique particulate tracers that were pumped throughout the stages, the stage groups, or any combination thereof from the tracer clouds.

9. The method of claim 7, further comprising analyzing the produced fluid samples obtained from the produced fluid to generate the tracer concentration history for each unique particulate tracer.

10. A method of determining a flow profile for a wellbore using unique particulate tracers, the method comprising:

pumping, through a wellbore drilled into a subterranean formation, unique particulate tracers throughout each stage, each stage group, or any combination thereof during a hydraulic fracturing operation performed in the subterranean formation, wherein each unique particulate tracer corresponds to an oil phase, a water phase, or a gas phase; and in a computer system that includes a physical computer processor and non-transitory storage medium:

a) obtaining, from the non-transitory storage medium, a tracer concentration history for each unique particulate tracer in produced fluid samples from the wellbore, wherein the produced fluid samples comprise at least a portion of the unique particulate tracers that were pumped throughout the stages, the stage groups, or any combination thereof;

b) obtaining, from the non-transitory storage medium, a production history for the wellbore;

c) determining, with the physical computer processor, a mean residence time for each unique particulate tracer using the corresponding tracer concentration history;

d) determining, with the physical computer processor, a contact volume proxy for each unique particulate tracer using the production history and the corresponding tracer concentration history; and e) determining, with the physical computer processor, a flow profile for the wellbore for each phase indicative of flow contribution of each stage, each stage group, or any combination thereof by using the corresponding mean residence times and the corresponding contact volume proxies, wherein:

the contact volume proxy of a specific unique particulate tracer refers to an approximate volume of the subterranean formation that was contacted by the specific unique particulate tracer; and determining the flow profile for the wellbore for each phase comprises, for each phase, determining the flowrate of each stage, each stage group, or any combination thereof based on the contact volume proxy over mean residence time for that stage or stage group or any combination thereof.

11. The method of claim 10, wherein the mean residence time is determined using an equation as follows:

$$t_{res} = \frac{\int_{t=0}^{t=\infty} c * t * dt}{\int_{t=0}^{t=\infty} c * dt}$$

wherein $t_{res}$ is mean residence time, c is tracer concentration history, t is time, and dt is integration with respect to time.

12. The method of claim 10, wherein the contact volume proxy is determined using an equation as follows:

$$vol_{proxy} = \int_{t=0}^{t=\infty} q * c * dt$$

wherein $vol_{proxy}$ is contact volume proxy, q is production history, c is tracer concentration history, t is time, and dt is integration with respect to time.

13. The method of claim 10, wherein the flow profile is determined using an equation as follows:

$$flow\_contribution_N(\%) = \frac{\frac{vol_{proxy\_N}}{t_{res\_N}}}{\sum_{i=1}^{i=M} \frac{vol_{proxy\_i}}{t_{res\_i}}} * 100$$

wherein $flow\_contribution_N$ is flow contribution for a specific stage or specific stage group, $t_{res}$ is mean residence time, $contact\_vol_{proxy}$ is contact volume proxy, i is a counter, M is total number of stages or stage groups in which unique particulate tracers were pumped, and N is specific stage or specific stage group for which flow contribution is determined.

14. The method of claim 10, further comprising:

smoothing a tracer concentration history for a specific unique particulate tracer before c) and d) to reduce noise; and utilizing the smoothed tracer concentration history for the specific unique particulate tracer in c) and d).

15. The method of claim 10, wherein the computer system further includes a graphical user interface, and the method further comprises:

generating, on the graphical user interface, a representation of the flow profile for the wellbore for each phase indicative of the flow contribution of each stage, each stage group, or any combination thereof; and displaying, via the graphical user interface, the representation.

16. A method of determining a flow profile for a wellbore using unique particulate tracers, the method comprising:

pumping, through a wellbore drilled into a subterranean formation, unique particulate tracers throughout each stage, each stage group, or any combination thereof during a hydraulic fracturing operation performed in the subterranean formation, wherein each unique particulate tracer corresponds to an oil phase, a water phase, or a gas phase;

obtaining produced fluid samples from the wellbore, wherein the produced fluid samples comprise at least a portion of the unique particulate tracers that were pumped throughout the stages, the stage groups, or any combination thereof; and determining a flow profile for the wellbore for each phase using the produced fluid samples comprising the unique particulate tracers by:

a) obtaining a tracer concentration history for each unique particulate tracer;

b) optionally obtaining a production history for the wellbore;

c) determining a decline rate for each unique particulate tracer using the corresponding tracer concentration history;

d) determining a normalization factor for each unique particulate tracer using the corresponding tracer concentration history and optionally the production history;

e) determining a normalized decline rate for each unique particulate tracer using the corresponding decline rate and the corresponding normalization factor; and f) determining a flow profile for the wellbore for each phase indicative of flow contribution of each stage, each stage group, or any combination thereof by using the corresponding normalized decline rates, wherein determining the flow profile for the wellbore for each phase comprises, for each phase, determining the flowrate of each stage, each stage group, or any combination thereof based on the normalized decline rate for that stage or stage group or any combination thereof.

17. The method of claim 16, wherein the decline rate is determined using an equation as follows:

$$r = \frac{dc}{dt}$$

59 wherein r is decline rate, dC is integration with respect to tracer concentration history, and dt is integration with respect to time.

18. The method of claim 16, wherein the normalization factor is represented as $$norm_{factor} = c_{mode}$$

wherein norm_factor is normalization factor and c_mode is a maximum value of a tracer concentration history.

19. The method of claim 16, wherein the normalization factor is determined using an equation as follows:

$$norm_{factor} = \int_{t=0}^{t=\infty} q * \rho * c * dt$$

wherein norm_factor is normalization factor, t is time, q is production history, $\rho$ is fluid density, c is tracer concentration history, and dt is integration with respect to time.

20. The method of claim 16, wherein the normalized decline rate is determined using an equation as follows:

$$r\_norm = \frac{r}{norm\_factor}$$

wherein r_norm is normalized decline rate, r is decline rate, and norm_factor is normalization factor.

21. The method of claim 16, wherein the flow profile is determined using an equation as follows:

$$flow\_contribution_N (\%) = \frac{r_{norm\_N}}{\sum_{i=1}^{i=M} r_{norm\_i}} * 100$$

wherein flow_contribution$_N$ is flow contribution for a specific stage or specific stage group, $r_{norm}$ is normalized decline rate, i is a counter, M is total number of stages or stage groups in which unique particulate tracers were pumped, and N is specific stage or specific stage group for which flow contribution is determined.

22. The method of claim 16, further comprising:

smoothing a tracer concentration history for a specific unique particulate tracer before c) and d) to reduce noise; and utilizing the smoothed tracer concentration history for the specific unique particulate tracer in c) and d).

23. The method of claim 16, further comprising:

generating, on a graphical user interface, a representation of the flow profile for the wellbore for each phase indicative of the flow contribution of each stage, each stage group, or any combination thereof; and displaying, via the graphical user interface, the representation.

24. A method of determining a flow profile for a wellbore using unique particulate tracers, the method comprising:

pumping, through a wellbore drilled into a subterranean formation, unique particulate tracers throughout each stage, each stage group, or any combination thereof during a hydraulic fracturing operation performed in the subterranean formation, wherein each unique particulate tracer corresponds to an oil phase, a water phase, or a gas phase; and in a computer system that includes a physical computer processor and non-transitory storage medium:

a) obtaining, from the non-transitory storage medium, a tracer concentration history for each unique particulate tracer in produced fluid samples from the wellbore, wherein the produced fluid samples comprise at least a portion of the unique particulate tracers that were pumped throughout the stages, the stage groups, or any combination thereof;

b) optionally obtaining, from the non-transitory storage medium, a production history for the wellbore;

c) determining, with the physical computer processor, a decline rate for each unique particulate tracer using the corresponding tracer concentration history;

d) determining, with the physical computer processor, a normalization factor for each unique particulate tracer using the corresponding tracer concentration history and optionally the production history;

e) determining, with the physical computer processor, a normalized decline rate for each unique particulate tracer using the corresponding decline rate and the corresponding normalization factor; and f) determining, with the physical computer processor, a flow profile for the wellbore for each phase indicative of flow contribution of each stage, each stage group, or any combination thereof by using the corresponding normalized decline rates, wherein determining the flow profile for the wellbore for each phase comprises, for each phase, determining the flowrate of each stage, each stage group, or any combination thereof based on the normalized decline rate for that stage or stage group or any combination thereof.

25. The method of claim 24, wherein the decline rate is determined using an equation as follows:

$$r = \frac{dc}{dt}$$

wherein r is decline rate, dC is integration with respect to tracer concentration history, and dt is integration with respect to time.

26. The method of claim 24, wherein the normalization factor is represented as $$norm_{factor} = c_{mode}$$

wherein norm_factor is normalization factor and c_mode is a maximum value of a tracer concentration history.

27. The method of claim 24, wherein the normalization factor is determined using an equation as follows:

$$norm_{factor} = \int_{t=0}^{t=\infty} q * \rho * c * dt$$

wherein norm_factor is normalization factor, t is time, q is production history, $\rho$ is fluid density, c is tracer concentration history, and dt is integration with respect to time.

28. The method of claim 24, wherein the normalized decline rate is determined using an equation as follows:

$$r\_norm = \frac{r}{norm\_factor}$$

wherein r_norm is normalized decline rate, r is decline rate, and norm_factor is normalization factor.

29. The method of claim 24, wherein the flow profile is determined using an equation as follows:

$$flow\_contribution_N(\%) = \frac{r_{norm\_N}}{\sum_{i=1}^{i=M} r_{norm\_i}} * 100$$

wherein $flow\_contribution_N$ is flow contribution for a specific stage or specific stage group, $r_{norm}$ is normalized decline rate, i is a counter, M is total number of stages or stage groups in which unique particulate tracers were pumped, and N is specific stage or specific stage group for which flow contribution is determined.

30. The method of claim 24, further comprising:

smoothing a tracer concentration history for a specific unique particulate tracer before c) and d) to reduce noise; and utilizing the smoothed tracer concentration history for the specific unique particulate tracer in c) and d).

31. The method of claim 24, wherein the computer system further includes a graphical user interface, and the method further comprises:

generating, on the graphical user interface, a representation of the flow profile for the wellbore for each phase indicative of the flow contribution of each stage, each stage group, or any combination thereof; and displaying, via the graphical user interface, the representation.

* * * * *